United States Patent
Zandstra et al.

(10) Patent No.: US 12,076,342 B2
(45) Date of Patent: Sep. 3, 2024

(54) METHOD FOR GENERATING PROGENITOR T CELLS FROM STEM AND/OR PROGENITOR CELLS AND USE OF SAME

(71) Applicant: THE GOVERNING COUNCIL OF THE UNIVERSITY OF TORONTO, Toronto (CA)

(72) Inventors: Peter W. Zandstra, Toronto (CA); Shreya Shukla, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 389 days.

(21) Appl. No.: 16/091,266

(22) PCT Filed: Apr. 7, 2017

(86) PCT No.: PCT/CA2017/050428
§ 371 (c)(1),
(2) Date: Oct. 4, 2018

(87) PCT Pub. No.: WO2017/173551
PCT Pub. Date: Oct. 12, 2017

(65) Prior Publication Data
US 2019/0142867 A1 May 16, 2019

Related U.S. Application Data

(60) Provisional application No. 62/320,005, filed on Apr. 8, 2016.

(51) Int. Cl.
| | |
|---|---|
| *A61K 35/17* | (2015.01) |
| *C12N 5/074* | (2010.01) |
| *C12N 5/0783* | (2010.01) |
| *C12N 5/0789* | (2010.01) |
| *A61P 7/00* | (2006.01) |
| *A61P 35/00* | (2006.01) |

(52) U.S. Cl.
CPC ............ *A61K 35/17* (2013.01); *C12N 5/0607* (2013.01); *C12N 5/0636* (2013.01); *C12N 5/0647* (2013.01); *C12N 5/0696* (2013.01); *A61P 7/00* (2018.01); *A61P 35/00* (2018.01); *C12N 2500/38* (2013.01); *C12N 2500/99* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/2307* (2013.01); *C12N 2501/25* (2013.01); *C12N 2501/42* (2013.01); *C12N 2501/58* (2013.01); *C12N 2501/998* (2013.01); *C12N 2502/1171* (2013.01); *C12N 2533/52* (2013.01); *C12N 2533/90* (2013.01)

(58) Field of Classification Search
CPC ..................................................... A61K 35/17
See application file for complete search history.

(56) References Cited

U.S. PATENT DOCUMENTS

2014/0248248 A1\* 9/2014 Zuniga-Pflucker ..... A61P 35/00
424/93.71
2018/0208895 A1 7/2018 Cavazzana-Calvo et al.

FOREIGN PATENT DOCUMENTS

| WO | 2010051634 A1 | 5/2010 |
| WO | 2016055396 A1 | 4/2016 |

OTHER PUBLICATIONS

Mohtashami et al. (cited on IDS) (Year: 2013).\*
Ulkyanova et al. (2005, Blood, vol. 106(1), pp. 86-94) (Year: 2005).\*
Burkly et al. (1991, Eur. J. Immunol., vol. 21, pp. 2871-2875) (Year: 1991).\*
Famili et al. (2017, Future Sci. OA, vol. 3(3), pp. 1-15) (Year: 2017).\*
Solomon et al. (1997, Blood, vol. 89(7), pp. 2461-2471) (Year: 1997).\*
Schmitt et al. (2006, Immunological Rev., vol. 209, pp. 95-102). (Year: 2006).\*
Besseyrias et al. (2007, JEM, vol. 204(2), pp. 331-343). (Year: 2007).\*
Mallon et al. (2006, Int. J. Biochem. Cell Biol., vol. 38(7), pp. 1063-1075) (Year: 2006).\*
Mohtashami et al. (2013, Int. Immunology, vol. 25(10), pp. 601-611) (Year: 2013).\*
Cloutier et al. (Apr. 1, 2016, Methods in Mol. Biol., vol. 1516, pp. 227-241) (Year: 2016).\*
Ikawa et al. (2010, Science, vol. 329, pp. 93-96) + Supplementary Data (Year: 2010).\*
Andrawes, et al., Intrinsic Selectivity of Notch 1 for Delta-like 4 Over Delta-like 1, Journal of Biological Chemistry, 2013, 288(35):25477-25489.
Awong, et al., Characterization In Vitro and Engraftment Potential In Vivo of Human Progenitor T Cells Generated From Hematopoietic Stem Cells, Blood, 2009, 114:972-982.
Awong, et al., Human Pro T-cells Generated In Vitro Facilitate Hematopoietic Stem Cell-Derived T-lymphopoiesis In Vivo and Restore Thymic Architecture, Blood, 2013, 122(26):4210-4219.
Besseyrias, et al., Hierarchy of Notch-Delta Interactions Promoting T Cell Lineage Commitment and Maturation, JEM, 2007, 204(2):331-343.

(Continued)

*Primary Examiner* — Anoop K Singh
*Assistant Examiner* — David A Montanari
(74) *Attorney, Agent, or Firm* — Quarles & Brady LLP

(57) ABSTRACT

The present disclosure provides a method for generating progenitor T cells from stem and/or progenitor cells comprising exposing the stem and/or progenitor cells to Notch ligand Delta-like-4 (DL4) and vascular adhesion molecule 1 (VCAM-1) under conditions suitable to generate progenitor T cells. The method provided is suitable for in vitro and in vivo pro-T cell generation. In vitro, the pro-T cells are generated under serum-free conditions. Cells produced using the method are provided as well as methods of using same.

9 Claims, 37 Drawing Sheets

Specification includes a Sequence Listing.

(56) References Cited

OTHER PUBLICATIONS

Calderon, et al., Synergistic, Context-Dependent, and Hierarchical Functions of Epithelial Components in Thymic Microenvironments, Cell, 2012, 149:159-172.

Csaszar, et al., An Automated System for Delivery of an Unstable Transcription Factor to Hematopoietic Stem Cell Cultures, Biotechnology and Bioengineering, 2009, 103(2):402-412.

Csaszar, et al., Rapid Expansion of Human Hematopoietic Stem Cells by Automated Control of Inhibitory Feedback Signaling, Cell Stem Cell, 2012, 10:218-229.

Csaszar, et al., Blood Stem Cell Fate Regulation by Delta-1-mediated Rewiring of IL-6 Paracrine Signaling, Blood, 2014, 123(5):650-658.

Frasca, et al., IL-11 Synergizes with IL-3 in Promoting the Recovery of the Immune System after Irradiation, International Immunology, 1996, 8(11):1651-1657.

Gehre, et al., A Stromal Cell Free Culture System Generates Mouse pro-T Cells That Can Reconstitute T-cell Compartments In Vivo, European Journal of Immunology, 2015, 45:932-942.

Holmes, et al., The OP9-DL1 System: Generation of T-lymphocytes from Embryonic or Hematopoietic Stem Cells In Vitro, Cold Spring Harbor Protocols, 2009, No. 2, 15 pages.

Hong, et al., Intrathymic IL-7: The Where, When, and Why of IL-7 Signaling During T Cell Development, Seminars in Immunology, 2012, 24:151-158.

Ikawa, et al., An Essential Developmental Checkpoint for Production of the T Cell Lineage, Science, 2010, 329:93-96.

Kirouac, et al., Cell-cell Interaction Networks Regulate Blood Stem and Progenitor Cell Fate, Molecular Systems Biology, 2009, 5:293, 20 pages.

La Motte-Mohs, et al., Induction of T-cell Development from Human Cord Blood Hematopoietic Stem Cells by Delta-like 1 In Vitro, Blood, 2005, 105(4):1431-1439.

Milne, et al., Stromal Cells Attract B-Cell Progtgenitors to Promote B-Cell-B-Cell Contact and Maturation, Scandinavian Journal of Immunology, 2005, 62(Suppl. 1):67-72.

Mohtashami, et al., Direct Comparison of DII1- and DII4-Mediated Notch Activation Levels Shows Differential Lymphomyeloid Lineage Commitment Outcomes, Journal of Immunology, 2010, 185:867-876.

Petrie, et al., Zoned Out: Functional Mapping of Stromal Signaling Microenvironments in the Thymus, Annual Review of Immunology, 2007, 25:649-679.

Prockop, et al., Stromal Cells Provide the Matrix for Migration of Early Lymphoid Progenitors Through the Thymic Cortex, Journal of Immunology, 2002, 169:4354-4361.

Purpura, et al., Systematic Engineering of 3D Pluripotent Stem Cell Niches to Guide Blood Development, Biomaterials, 2012, 33:1271-1280.

Reimann, et al., Human T-Lymphoid Progenitors Generated in a Feeder-Cell-Free Delta-Like-4 Culture System Promote T-Cell Reconstitution in NOD/SCID/γc-/-Mice, Stem Cells, 2012, 30:1771-1780.

Roccio, et al., High-Throughput Clonal Analysis of Neural Stem Cells in Microarrayed Artificial Niches, Integrative Biology, 2012, 4:391-400.

Salomon, et al., Vascular Cell Adhesion Molecule-1 is Expressed by Cortical Thymic Epithelial Cells and Mediates Thymocyte Adhesion. Implications for the Function of a4B1 (VLA4) Integrin in T-Cell Development, Blood, 1997, 89(7):2461-2471.

Shukla, et al., Progenitor T-cell Differentiation from Hematopoietic Stem Cells Using Delta-like-4 and VCAM-1, Nature Methods, 2017, 14(5):531-538.

Smith, et al., In Vitro T-Cell Generation From Adult, Embryonic, and Induced Pluripotent Stem Cells: Many Roads to One Destination, Stem Cells, 2015, 33:3174-3180.

Taqvi, et al., Biomaterial-Based Notch Signaling for the Differentiation of Hematopoietic Stem Cells into T Cells, J Biomed Mater Res, 2006, 79A:689-697.

Varnum-Finney, et al., Immobilization of Notch Ligand, Delta-1, is Required for Induction of Notch Signaling, Journal of Cell Science, 2000, 113:4313-4318.

Lehnert et al., MAdCAM-1 Costimulates T Cell Proliferation Exclusively Through Integrin a4B7, Whereas VCAM-1 and CS-1 Peptide Use α4β1: Evidence for "Remote" Costimulation and Induction of Hyperresponsiveness to B7 Molecules, European Journal of Immunology, 1998, 28(11):3605-3615.

European Patent Office, Supplementary European Search Report, Application No. 17778524.3, datd Oct. 7, 2019, 5 pages.

Lee et al., From stem cell to immune effector: how adhesion, migration, and polarity shape T-cell and natural killer cell lymphocyte development in vitro and in vivo, MBoc Perspective, Molecular Biology of the Cell, 2020, vol. 31, pp. 981-991.

Singh et al., Producing proT cells to promote immunotherapies, International Immunology, 2018, vol. 30, No. 12, pp. 541-550.

Brauer et al., T Cell Genesis: In Vitro Veritas Est?, Trends in Immunology, 2016, vol. 37, No. 12, pp. 889-901.

Wattanapanitch, Recent Updates on Induced Pluripotent Stem Cells in Hematological Disorders, Hindawi Stem Cells International, vol. 2019, pp. 1-15.

\* cited by examiner a b c d

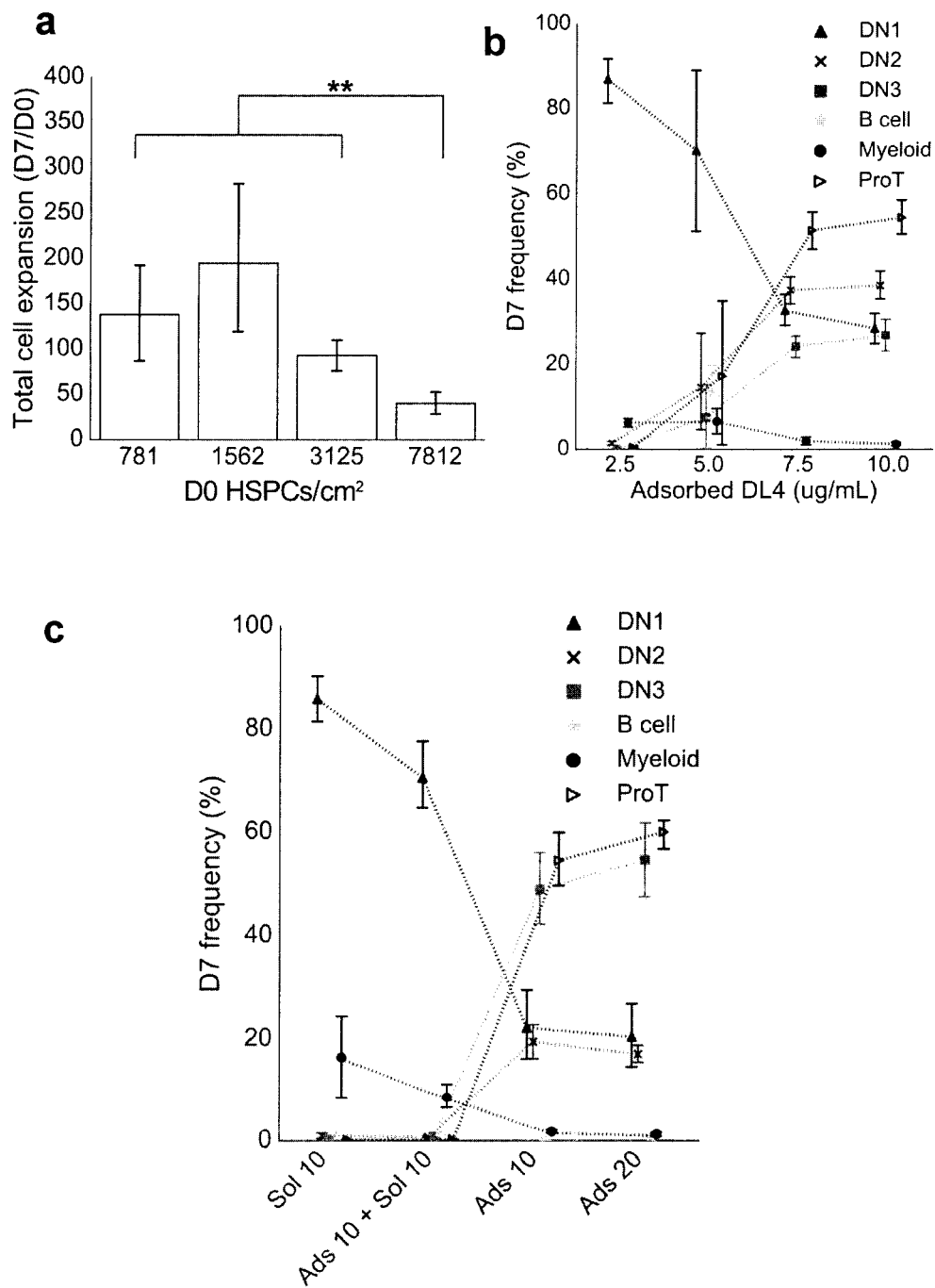
FIGS. 4a-c

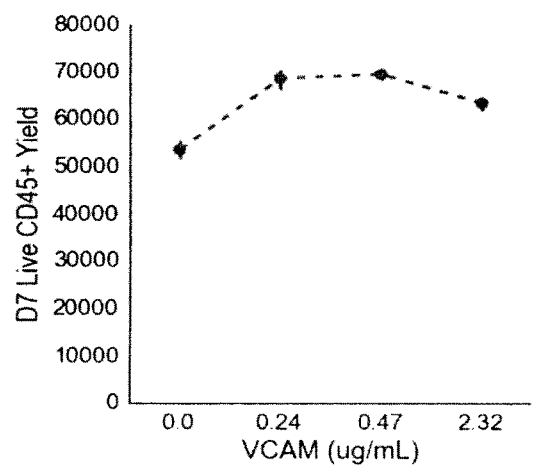
FIG. 7
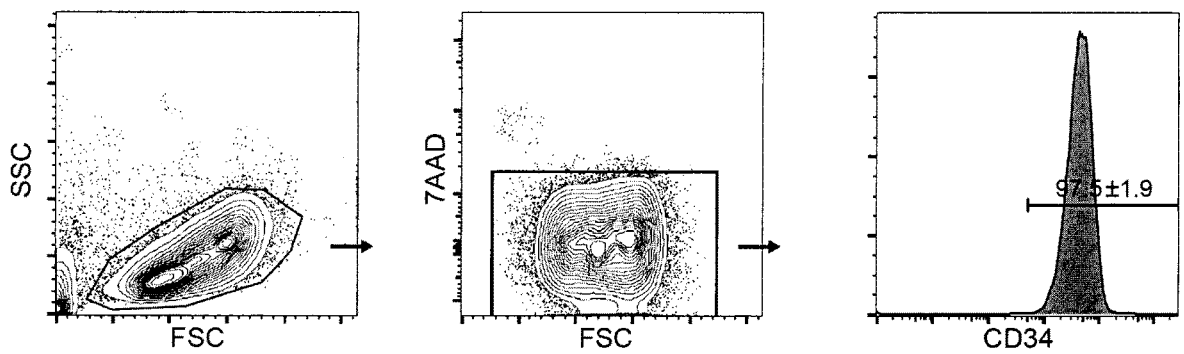
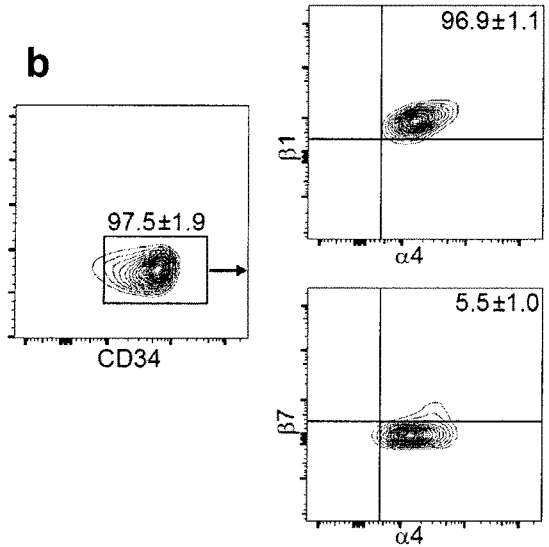
FIGS. 8a-8b

FIG. 12a
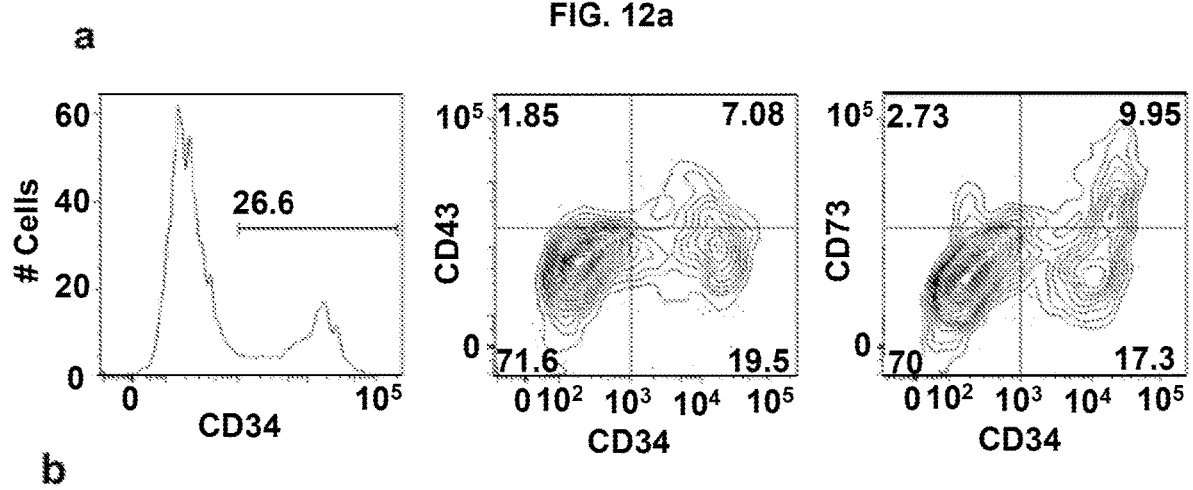
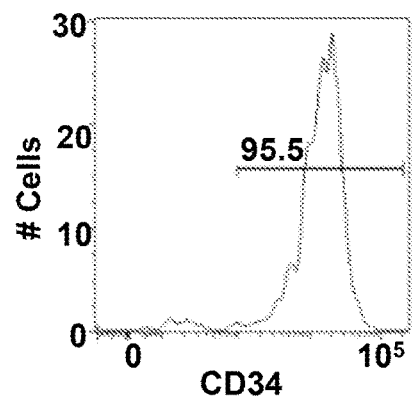
FIG. 12b

METHOD FOR GENERATING PROGENITOR T CELLS FROM STEM AND/OR PROGENITOR CELLS AND USE OF SAME

CROSS-REFERENCE TO RELATED APPLICATIONS

This application represents the national stage entry of PCT International Application No. PCT/CA2017/050428 filed Apr. 7, 2017, which claims priority under the Paris Convention to U.S. Provisional Patent Application Ser. No. 62/320,005, filed Apr. 8, 2016, both of which are incorporated herein by reference as if set forth in their entirety for all purposes.

FIELD OF THE DISCLOSURE

The present description relates generally to in vitro methods for generating progenitor T cells. More particularly, the description relates to methods for generating human progenitor T cells in vitro from stem and/or progenitor cells and use of same.

BACKGROUND OF THE DISCLOSURE

T cells are a type of lymphocyte that play a central role in cell-mediated immunity. For example, T cells are involved with regulating immune responses and maintaining an immunological memory of recurring pathogens in the body. T cell deficiency can be lethal, particularly in post-chemotherapy patients, who are at increased risk for opportunistic infections.

Conventional in vitro T cell development from hematopoietic stem and progenitor cells (HSPCs) is carried out in serum-containing medium and on murine OP9 feeders engineered to express Notch-activating DL4 protein[1,2]. The undefined and xenogeneic nature of this system makes it difficult to study the role of endogenously secreted factors or matrix components, and limits clinical translation. It has been reported that use of an OP9 feeder layer can be avoided by non-specific adsorption of Notch ligands to tissue culture plates[3]. However, this OP9-free system required use of high amounts of animal sera in the medium. Immobilization of DL4 to magnetic microbeads has also been reported as an artificial Notch signaling system. However, this approach suffered from skewing to non-T (B lineage) cells[4]. In one study, Notch ligand Jagged1-Fc was robotically spotted on microfabricated pillars, stamped on thin thiolated PEG hydrogel films and tethered via maleimide-modified Protein A to study its effects on self-renewal of single neural stem cells[5]. However, there is no evidence to suggest that this small scale, single cell approach would be suitable for translation to T cell development for clinical applications. Currently there are no reports of a defined system for T cell development.

SUMMARY OF THE DISCLOSURE

In an aspect, a method of generating progenitor T cells from stem and/or progenitor cells is provided. The method comprises culturing stem and/or progenitor cells in the presence of at least a portion of Notch ligand Delta-like-4 (DL4) and at least a portion of vascular adhesion molecule 1 (VCAM-1) under serum-free conditions to generate progenitor T cells.

In an embodiment, the culturing step further comprises generating derivatives of the generated progenitor T cells.

In an embodiment, the portion of DL4 comprises the extracellular domain of DL4. In an embodiment, the DL4 is adsorbed or immobilized to a substrate.

In an embodiment, the portion of VCAM-1 comprises the Phe25-Glu698 of SEQ ID NO: 4 fused with the Fc region of human IgG1.

In an embodiment, the portion of DL4 is provided in a concentration in the range of 7.5 to 20 µg/mL. In an embodiment, the portion of DL4 is provided in a concentration of about 15-20 µg/mL.

In an embodiment, the portion of VCAM-1 is provided in a concentration in the range of 0.15 to 5.3 µg/mL. In an embodiment, the portion of VCAM-1 is provided in a concentration of about 2.5-5.3 µg/mL.

In an embodiment, the culturing of the stem and/or progenitor cells comprises exposing the stem and/or progenitor cells to a hematopoietic differentiation medium comprising SCF, FLT3L and IL-7.

In an embodiment, the stem and/or progenitor cells are human cells. In an embodiment, the stem and/or progenitor cells are pluripotent stem cells or hematopoietic stem and progenitor cells.

In an aspect, an isolated population of progenitor T cells generated by the method disclosed herein is provided.

In an embodiment, the isolated population comprises derivatives of the progenitor T cells.

In an embodiment, the population comprises at least 20% CD7+ progenitor T cells. In an embodiment, the population comprises at least 60% CD7+ progenitor T cells.

In an embodiment, the progenitor T cells are human cells that express CD7. In an embodiment, the human progenitor T cells express one or more of CD34, CD45RA, and CD5.

In an aspect, a method for increasing the number of T cells in a subject in need thereof is provided. The method comprises administering to the subject an effective number of progenitor T cells as provided herein.

In an embodiment, the subject is a human.

In an embodiment, the administered progenitor T cell are autologous.

In an embodiment, the administered progenitor T cells are allogeneic.

In an embodiment, the subject in need of the increased number of T cells has a medical condition causing or resulting in lymphopenia. In an embodiment, the medical condition is cancer, HIV infection, partial thymectomy, autoimmune disease, and/or organ transplant.

DESCRIPTION OF THE DRAWINGS

These and other features of the disclosure will become more apparent in the following detailed description in which reference is made to the appended drawings wherein:

FIG. 1a: Immunoblot depicting 10 µg lysates of non-transfected HEK293T (control) and transfected cells (DL4-Fc) that were immunoblotted for human IgG (anti-hIgG) to determine the expression of DL4-Fc.

FIG. 1b: Coomassie blue staining depicting supernatant from cultured HEK293T cells stably expressing DL4-Fc that were passed through affinity-purification protein G column and assessed.

FIG. 1c: Depiction of DL4-Fc ligand binding double negative (DN; CD4− CD8−) and not double positive (DP, CD4+CD8+) thymocytes.

FIG. 2a: Schematic for 2D coated DL4 assay, in which sorted E13.5 sca1+ckit+ fetal-liver HSPCs are seeded on coated DL4 ligand in standard 96-well flat bottom plates at 1000 cells/well density in 200 μl test media containing cytokines 25 ng/mL SCF, 5 ng/mL Flt3L and 1 ng/mL IL7; cells are re-fed on day 4 with fresh media containing cytokines; on day 7, cells are assayed for surface marker expression using flow cytometry.

FIG. 2o: Graph depicting quantification of yield of CD25+ CD90+ proT cells at day 7 vs. frequency of DN3 (CD25+ CD44−CD45+) cells in different serum-free media compositions compared to OP9 serum medium control (shaded areas in FIGS. 2m-o were plotted using a bivariate kernel density estimate function; all data points are depicted for n=3 biological replicates).

FIG. 3a: Graph depicting CD19+ B cell fold expansion on day 7 over day 0 input HSPCs in the presence or absence of 2D coated DL4; αMEM+BIT serum-free media produced the best myeloid and B cell yields comparable to serum media control.

FIG. 3b: Graph depicting CD19+ B cell expansion on day 7 over input sorted HSPCs on day 0 in the different media compositions in the presence or absence of DL4 (n=3); data represent mean±95% Cl for n=3 biological replicates (*P<0.05; P<0.01; *P<0.001).

FIG. 3c: Graph depicting CD11 b+ myeloid fold expansion on day 7 over day 0 input HSPCs in the presence or absence of 2D coated DL4.

FIG. 3d: Graph depicting CD19+ B cell expansion on day 7 over input sorted HSPCs on day 0 in the different media compositions in the presence or absence of DL4 (n=3); data represent mean±95% Cl for n=3 biological replicates (*P<0.05; P<0.01; *P<0.001).

FIGS. 4a-g depict optimization of key assay design criteria to engineer the thymic niche.

FIG. 4a: Graph depicting quantification of total CD45+ 7AAD− live cell expansion at day 7 normalized to increasing input day 0 sorted HSPC seeding densities per cm$^2$ (n=3) (data represent mean±95% Cl for n=3 biological replicates; *P<0.05; P<0.01; *P<0.001); while total cell expansion was significantly lower in cultures with seeding densities above $3.1\times10^3$ HSPCs/cm$^2$, higher variability in the total cell expansion was observed in cultures with seeding densities below $3.1\times10^3$ HSPCs/cm$^2$.

FIG. 4b: Graph depicting sorted HSPCs that were seeded on increasing amounts of adsorbed DL4 in serum-free IMDM+BIT medium and analyzed on day 7 for frequencies of various proT, B and myeloid cell populations (n=3); 7.5 μg/mL of DL4 was the minimum concentration that supported DN3 pro-T cell generation in IMDM+BIT serum-free medium at levels equivalent to the OP9 serum medium control after 7 days of culture.

FIG. 4c: Graph depicting sorted HSPCs that were seeded in soluble 10 μg/mL DL4 ligand, on adsorbed 10 or 20 μg/mL DL4 ligand or a mixture of adsorbed and soluble ligand in serum-free IMDM+BIT medium and cell frequencies were quantified on day 7 (n=3); HSPCs differentiated in soluble DL4 produced significantly less DN3 cells and retained a DN1 phenotype, whereas DN3 cells were the primary output population on adsorbed DL4; in conditions combining adsorbed and soluble DL4, the presence of soluble DL4 hindered the inductive effect of the adsorbed DL4 on DN3 cell production.

FIG. 4d: Schematic for elimination of day 4 media exchange while reducing media consumption; baseline "re-feed" differentiation strategy involved seeding cells in 200 μl media/well with 50% media exchange at day 4 with double the cytokine concentration at day 0 to maintain the same concentration; the optimized "no-feed" differentiation strategy involved seeding cells in 50 μl media/well with higher cytokine concentrations and no media exchange at day 4.

FIG. 4e: Results of Design of Experiment (DOE) surface response approach that was implemented to optimize the concentrations of SCF, FLT3L and IL7 for the "no-feed" differentiation strategy; The design cube depicts the optimal concentration prediction from the DOE model of the concentrations of cytokines to use.

FIGS. 4f and g: Graph depicting DN2 (k) or DN3 (l) frequency at day 7 with the positive control (25-5-1 re-feed condition) vs. the optimized no-feed process using serum-free IMDM+BIT medium; by simply increasing the IL-7 concentration from 2 to 10 ng/mL (50-10-10 no-feed condition), the cells produced a significantly higher yield of DN2 and higher frequency and yield of T lineage-committed DN3 cells than the control (shaded areas were plotted using a bivariate kernel density estimate function; all data points are depicted for n=3 biological replicates).

FIG. 5a: Graph depicting quantification of DN1, DN2, DN3, CD19+ B cell, CD11 b+ myeloid and CD25+CD90+ proT cell subset frequencies on day 7 with increasing input day 0 sorted HSPC seeding densities per cm$^2$ (n=3); data represent mean±95% Cl for n=3 biological replicates. *P<0.05; P<0.01; *P<0.001.

FIG. 5b: Graph depicting quantification of DN1, DN2, DN3, CD19+ B cell, CD11 b+ myeloid and CD25+CD90+ proT cell subset frequencies on day 7 obtained on increasing coating concentrations of DL1 ligand (n=3) (data represent mean±95% Cl for n=3 biological replicates. *P<0.05; P<0.01; *P<0.001); consistent with previous observations[6], the Notch ligand DL1 was found to be less efficient for T-cell induction than DL4 due to weaker Notch pathway activation.

FIG. 5c: Graph depicting quantification of DN1, DN2, DN3, CD19+ B cell, CD11 b+ myeloid and CD25+CD90+ proT cell subset frequencies at day 7 in U-bottom (U bot) vs. flat-bottom plates (flat bot) with no coating (−DL4) or 10 μg/ml DL4 (+ DL4) on day 0 (n=3) (data represent mean±95% Cl for n=3 biological replicates. *P<0.05; P<0.01; *P<0.001); while well shape (U-bottom vs. flat) significantly influenced myeloid and B cell fate as reported previously[7], it did not impact T-cell commitment.

FIG. 5d: Graph depicting notch pathway CBF-1 Firefly activation normalized to constitutively active *Renilla* plasmid after 24 hours on 0 μg/mL DL4-Fc (no ligand; negative control) and 10 μg/mL DL4-Fc (positive control) to test activity of DL1-Fc at 10 and 20 μg/mL (n=3); adsorbed DL1 ligand was unable to sustain progenitor T cell production or activate the Notch pathway at similar coating concentrations as DL4 ligand (data represent mean±95% Cl for n=3 biological replicates. *P<0.05; P<0.01; *P<0.001).

FIG. 5e: Graph depicting Notch signaling pathway activation that was measured using intranuclear CBF1-Firefly activation normalized to constitutively active *Renilla* plasmid in no ligand, soluble DL4, adsorbed DL4, or a mixture of soluble and adsorbed DL4 (n=3).

FIG. 5f: Design of Experiment (DOE) 3D surface response curve depicting desirability of simultaneously varying SCF and FLT3L test concentrations at the optimal constant IL7 concentration to maximize committed DN3 T cell progenitor frequency.

FIG. 5g: DOE 2D surface response curve depicting desirability of varying SCF and IL7 test concentrations at the optimal constant FLT3L concentration to maximize committed DN3 T cell progenitor frequency.

FIG. 6a: Flow cytometry analysis of the expression of $\alpha_4\beta_1$, $\alpha_4\beta_7$ and $\alpha_5\beta_1$ integrins in fetal liver HSPCs. Sca-1$^+$ c-kit$^+$ 7AAD$^-$ cells (HSPC compartment) were selected from an unsorted Ter119$^-$ cell population; HSPCs express $\alpha_4\beta_1$ and $\alpha_5\beta_1$ with a few expressing $\alpha_4\beta_7$ integrin.

FIG. 6*n*: Graphs depicting qRT-PCR gene expression of downstream Notch pathway genes (Hes1, Deltex, Notch1, Bcl11b, Gata3, Tcf7), a HSPC gene (E2a) and a myeloid lineage gene (PU.1) on no coating, 2.32 µg/mL VCAM-1, 10 µg/mL DL4, or DL4+VCAM-1 after 24 and 48 hours of culture with sorted HSPCs (n=3); data represent mean±95% CI for n≥3 biological replicates except for qRT-PCR data which represents mean±standard error for n=3 biological replicates (*P<0.05; P<0.01; *P<0.001).

FIG. 7 depicts live cell expansion on DL4 in combination with extracellular matrix cues; On day 7 of differentiation, live cells were quantified via CD45+7AAD− gating using flow cytometry; cells were differentiated on either DL4 alone or with increasing doses of VCAM-1.

FIGS. 8*a-h* illustrate that human CD34+ HSPCs can generate progenitor T cells in the engineered thymic niche.

FIG. 8*a*: The purity of the input umbilical cord blood-derived HSPCs was verified to be greater than 95% CD34+ prior to initiation of each culture; CD34+ frequency was assessed on 7AAD− live cell population (n=3).

FIG. 8*b*: Day 0 umbilical cord blood-derived CD34+ cells (HSPC compartment) were analyzed for the expression of α4β1 and α4β7 integrins (n=3).

FIGS. 8*c* and *d*: Graphs depicting human cord blood-derived CD34+ cells that were cultured on adsorbed 10 µg/mL DL4 alone or DL4 with fibronectin (FN), retronectin (RN) or VCAM-1 for (FIG. 8*c*) 9 days or (FIG. 8*d*) 14 days and analyzed by flow cytometry for expression of CD7, CD34, CD45RA and CD5. By day 9, DL4+VCAM-1 cultures generated CD7+CD34−, CD7+CD45RA+ and CD7+CD5+ progenitor T-cell phenotypes (n=3).

FIG. 8*e*: Representative FACS plots of human CD34+ HSPCs grown for 9 or 14 days on engineered thymic niche. Generation of CD7+ cells that co-express CD5 and CD45RA is seen as early as day 9 of culture.

FIG. 8*f*: Graph depicting CD7+CD34− cell fold expansion on day 14 normalized to input day 0 CD34+ HSPCs on adsorbed 10 µg/mL DL4 alone or DL4 with fibronectin (FN), retronectin (RN) or VCAM-1 (n=3).

FIG. 8*g*: Representative flow cytometry plots of human CD34+ HSPCs grown for 14 days on DL4 alone or DL4+VCAM-1 (n=3).

FIG. 8*h*: Graphs depicting qRT-PCR gene expression of downstream Notch pathway genes (Hes1, Deltex, Notch1, Bcl11b, Gata3, Tcf7), a HSPC gene (E2a) and a myeloid lineage gene (PU.1) on no coating, 2.32 µg/mL VCAM-1, 10 µg/mL DL4, or DL4+VCAM-1 after 24 hours of culture with human CD34+ HSPCs (n=5); data represent mean±standard error for n=5 biological replicates (*P<0.05; P<0.01; *P<0.001).

FIG. 9*a*: Graph depicting total cell expansion on day 14 normalized to input day 0 CD34+ HSPCs on the DL4+VCAM-1 engineered thymic niche or control OP9-DL4 co-culture (n=6).

FIG. 9*b*: Graph depicting CD7+ expression on day 14 on the DL4+VCAM-1 engineered thymic niche or control OP9-DL4 co-culture (n=6); no significant difference was found between OP9-DL4 and the engineered thymic niche.

FIG. 9*c*: Graph depicting quantification of CD7+CD34+, CD7+CD34− and CD7+CD5+ populations after 14 days of OP9-DL4 co-culture or on the engineered thymic niche; data represent mean±95% CI for n=6 biological replicates except for flow plots that represent mean±standard deviation for n=3 mice/group (*P<0.05; P<0.01; *P<0.001; n.s. indicates no significance).

FIG. 10*a*: Schematic of in vivo study performed using sorted CD7+ cells derived from either the engineered thymic niche or control OP9-DL4 system; the cells were injected intra-hepatically in SRG neonate mice and transfused with human IL-7 and IL-7 antibody (M25) every 4 days; cells were harvested from the thymus after 4 weeks and from peripheral blood and spleen after 10-12 weeks; cells were electronically gated on human CD45+ expression to analyze the expression of mature T-cell surface markers.

FIG. 10*b*: Graph depicting sorted CD7+ cells derived from either the engineered thymic niche or control OP9DL4 system homed to and engrafted the thymi in vivo in SRG neonate mice after 4 weeks as assessed by human CD45+ expression quantified in the murine thymi.

FIG. 10*c*: Representative flow plots of cells derived from in vivo SRG thymi that were gated on human CD45+ expression and developed into double positive T cells co-expressing CD3, CD4 and CD8.

FIG. 10*d*: Representative flow plots of CD7, CD5, CD1a, CD4 and CD8 co-expression on maturing T-cells harvested from SRG thymi 4 weeks after infusion of CD7+ cells from either OP9-DL4 co-culture or from the engineered thymic niche (n=3 mice/group).

FIG. 10*e*: Representative flow plots of CD8 and CD3 expression on circulating mature cytotoxic T-cells harvested from peripheral blood 10-12 weeks after infusion of CD7+ cells from either OP9-DL4 co-culture or from the engineered thymic niche (n=3 mice/group).

FIG. 10*f*: representative flow plots of intracellular IL-2, IFN-γ and TNF-α cytokine secretion from mature CD3+ T-cells post in vitro stimulation for 6 hours with PMA and ionomycin (n=3 mice/group) (cells were harvested from the spleen 10-12 weeks after infusion of CD7+ cells from either OP9-DL4 co-culture or from the engineered thymic niche); (for FIGS. 10*d-f*, flow plots that represent mean±standard deviation for n=3 mice/group. *P<0.05; P<0.01; *P<0.001; n.s. indicates no significance; no significant difference was found between OP9-DL4 and the engineered thymic niche).

FIG. 10*g*: Schematic of proposed mechanism.

FIG. 11*a*: Schematic of expansion of day 0 CD34+ HSPCs derived from cord blood via fed-batch and fed-batch+UM729 small molecule bioreactor technologies; cells were harvested from both culture methods at day 12 and sorted for CD34+ and CD34-populations; sorted CD34+ and CD34− cells from both culture methods were seeded along with thawed unexpanded day 0 CD34+ HSPCs at 4000 cells/96-well coated overnight with 20 µg/mL DL4 and 2.3 µg/mL VCAM-1 in serum-free IMDM+BIT medium containing 100 ng/mL SCF, Tpo, Flt3L and IL-7; cultures fed once 7 days later and harvested 14 days later for FACS analysis of lymphoid and myeloid lineage cell surface markers.

FIG. 11o: Graph depicting yield of myeloid cells from total number of CD34+ cells obtained from day 0 cord blood, day 12 FB and day 12 FB+UM cultures; Day 12 FB+UM tended to have the highest yield of myeloid cells from total number of CD34+ cells obtained from each culture method (n=2).

FIGS. 12a-d depict generation of progenitor T (CD7+CD56−) cells from human pluripotent stem cell (hPSC)-derived hemogenic endothelium (HE) cells.

FIG. 12a: Phenotype of hPSC-derived HE cells produced at day 6 of culture; representative flow plots depticting cells express CD34+ that co-expressed CD43 and CD73.

FIG. 12b: Magnetic enrichment of day 6 hPSC-derived CD34+HE cells and assessment of CD34+ expression post-enrichment.

FIG. 12c: Representative flow plots of day 6 enriched CD34+ cells were seeded either on OP9DL4 or DL4+VCAM-1 serum-free culture and assayed via flow cytometry two weeks later for progenitor T cell markers; generation of CD7+CD34− cells that express low levels of CD5 was seen from PSC-derived CD34+ cells seeded on DL4+VCAM-1 plates.

FIG. 12d: Representative flow plots of positive control cultures were seeded in parallel on DL4+VCAM-1 plates using day 0 CD34+ HSPCs derived from umbilical cord blood; the CD34− fraction from day 6 PSC-derived HE was also seeded on DL4+VCAM-1 and assayed from progenitor T cell production.

FIG. 13a: Graph depicting total cell expansion of UCB-derived CD34+ cells differentiated for 14 days in parallel on OP9-DL4 stromal co-culture (n=6) or in serum-free conditions on 96-well plates (n=6), 6-well plates (n=3), or adherent culture bioreactor bags (n=1), coated with DL4+VCAM-1.

FIG. 13b: Graph depicting frequencies of CD7+, CD7+CD34+, CD7+CD34−, and CD7+CD5+ progenitor T cells.

FIG. 13c: Representative flow plots demonstrate day 14 CD7+, CD7+CD34+, CD7+CD34−, and CD7+CD5+ progenitor T cells produced on OP9DL4, DL4+VCAM-1 coated 6-well plates and DL4+VCAM-1 coated adherent culture bioreactor bags.

DETAILED DESCRIPTION OF THE DISCLOSURE

Figures 1A, 1B, 1C:
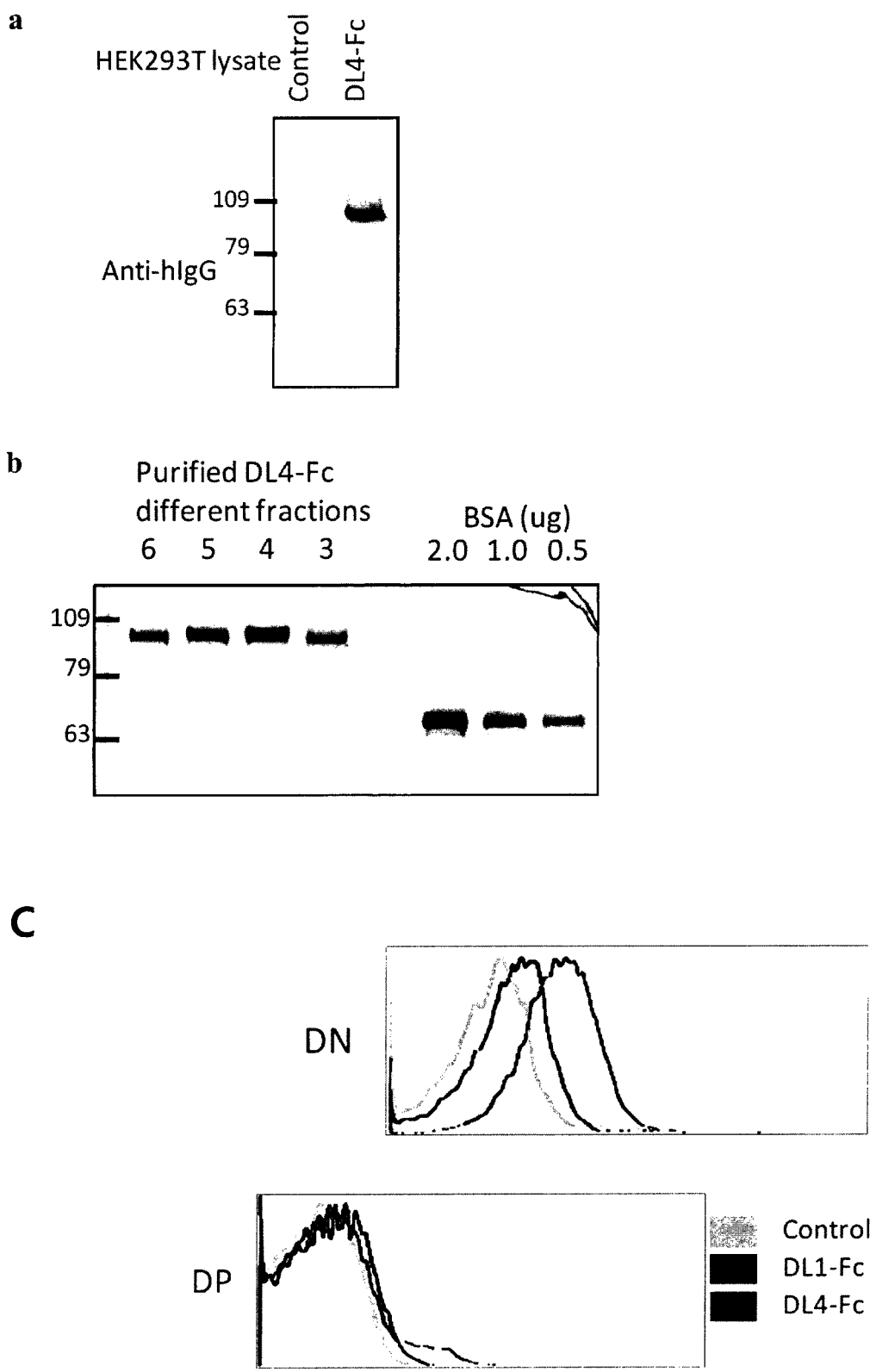
FIGS. 1a-c illustrate that DL4-Fc ligand can be produced in HEK293T cells and its binding capability can be verified using double negative (DN) T cells.

Unless defined otherwise, all technical and scientific terms used herein have the same meaning as commonly understood by one of ordinary skill in the art to which this disclosure belongs.

Definitions

As used herein, the term "stem cell" refers to a cell that can differentiate into more specialized cells and has the capacity for self-renewal. Stem cells include pluripotent stem cells (PSCs), such as embryonic stem cells (ESCs) and induced pluripotent stem cells (iPSCs), and multipotent stem cells, such as cord blood stem cells, and adult stem cells, which are found in various tissues.

As used herein, the term "progenitor cell" refers to a cell that can differentiate into one or more types of cells, but does not typically have the capacity for self-renewal. Progenitor cells are derivatives of stem cells and have more limited potency relative to their corresponding source stem cells. For example, hematopoietic stem cells (HSCs), found in adult bone marrow, peripheral blood (in smaller numbers) and in umbilical cord blood, have the capacity to give rise to all other blood cells. Hematopoietic progenitor cells are multipotent or lineage-committed cells derived from HSCs that have the capacity to give rise to a more limited or specific type of blood cell. Hematopoietic stem and progenitor cells (HSPCs) typically exist as a heterogeneous population in vivo and have use as a heterogeneous population as described herein.

As used herein, the terms "progenitor T cell" and "pro-T cell" refer to a cell that is derived from a pluriportent stem cell or a CD34+ hematopoietic stem and/or progenitor cell and expresses CD7+(human system) or CD25+CD90+ (mouse system), and has the capacity to differentiate into one or more types of mature T cells. A mature T cell includes cells that express a combination of CD4, CD8 and CD3 cell surface markers.

As used herein, a "defined culture medium" refers to a chemically-defined formulation comprised solely of chemically-defined constituents. A defined medium may include constituents having known chemical compositions. Medium constitutents may be synthetic and/or derived from known non-synthetic sources. For example, a defined medium may include one or more growth factors secreted from known tissues or cells. However, the defined medium will not include the conditioned medium from a culture of such cells. A defined medium may include specific, known serum components isolated from an animal, including human serum components, but the defined medium will not include serum. Any serum components provided in the defined medium such as, for example, bovine serum albumin (BSA), are preferably substantially homogeneous.

As used herein, "serum-free medium" refers to a cell culture medium that lacks animal serum. Serum-free medium may include specific, known serum components isolated from an animal (including human animals), such as, for example, BSA.

As used herein, "Delta-like-4", "DL4" and "Notch ligand DL4" refer to a protein that in humans is encoded by the DLL4 gene. DL4 is a member of the Notch signaling pathway and is also referred to in the art as "Delta like ligand 4" and "DLL4". Herein, reference to DL4 is not limited to the entire DL4 protein, but includes at least the signaling peptide portion of DL4. For example, a commercially available product (Sino Biologicals) comprising the extracellular domain (Met 1-Pro 524) of human DLL4 (full-length DLL4 accession number NP_061947.1; SEQ ID NO: 1) fused to the Fc region of human IgG1 at the C-terminus is a DL4 protein suitable for use herein.

As used herein, "Vascular cell adhesion molecule 1" and "VCAM-1" refer to a protein that in humans is encoded by the VCAM1 gene. VCAM-1 is a cell surface sialoglycoprotein, a type I membrane protein that is a member of the Ig superfamily. VCAM-1 is also referred to in the art as "vascular cell adhesion protein 1 and cluster of differentiation 106 (CD106). Herein, reference to VCAM-1 is not limited to the entire VCAM-1 protein, but includes at least the signaling peptide portion of VCAM-1 (QIDSPL (SEQ ID NO: 2) or TQIDSPLN (SEQ ID NO: 3)). For example, a commercially available mouse VCAM-1 Fc chimeric protein (R&D) that comprises (Phe25-Glu698) region of mouse VCAM-1 (full-length murine VCAM-1 accession number CAA47989; SEQ ID NO: 4) fused with the Fc region of human IgG1 is a VCAM-1 protein suitable for use herein. Use of at least a portion of human VCAM-1 (full-length human VCAM-1 accession number P19320, NP001069, EAW72950; SEQ ID NO: 5) may also be suitable for use in the method provided herein.

GENERAL DESCRIPTION OF THE DISCLOSURE

As described herein, the inventors have determined an in vitro method for generating progenitor T cells (pro-T cells) in a serum-free system. The method involves culturing stem and/or progenitor cells in the presence of the Notch ligand Delta-like-4 (DL4) and VCAM-1 in serum-free medium to generate pro-T cells. In an embodiment, the inventors found that DL4 and VCAM-1 synergistically enhance Notch signaling and promote pro-T cell differentiation and migration.

Pro-T cells generated using the method provided herein are provided. The cells provided herein may be used, for example, to treat a subject in need of pro-T cells and/or more mature T cells, as described further below. For example, a host in need of additional pro-T cells and/or mature T cells may be subjected to a cell transplant that comprises an effective amount of the pro-T cells provided herein or an effective amount of the pro-T cells provided herein in combination with stem cells (e.g., HSPCs).

Method of Generating Progenitor T Cells In Vitro

Generally, the in vitro method of generating pro-T cells involves culturing stem and/or progenitor cells in the presence of DL4 and VCAM-1 in serum-free medium under conditions and for a time suitable for differentiation into pro-T cells. To confirm generation of pro-T cells, the cells may be analyzed for one or more features indicative of pro-T cells, such as, for example, one or more cell surface markers.

In an embodiment, the stem and/or progenitor cells are pluripotent stem cells, such as ESCs or iPSCs. In an embodiment, the stem and/or progenitor cells are HSPCs. For example, the HSPCs may be obtained from cord blood, peripheral blood or bone marrow or they may be derived in vitro from ESCs, iPSCs or other intermediate stem cells. In a preferred embodiment, the stem and/or progenitor cells are human cells.

In an embodiment, the method is performed in a two dimensional (2D) culture system. For example, one or more wells of a standard tissue culture plate are coated with DL4 and VCAM-1. In an embodiment, the DL4 and VCAM-1 are provided as adsorbed proteins. Stem cells and/or progenitor cells are then seeded into the 2D DL4– and VCAM-1-coated wells in serum-free hematopoietic differentiation medium and cultured for a time and under conditions suitable for generating pro-T cells. Media generally suitable for hematopoietic differentiation are known to those of skill in the art and are commercially available. In an embodiment, a preferred medium for hematopoietic differentiation suitable for use in the method provided herein is described herein.

In an embodiment, wells of a standard 96-well tissue culture plate are coated overnight with about 50 μL/well of DL4-Fc at a concentration in the range of 7.5-20 μg/mL (preferably about 15-20 μg/mL) and VCAM-1-Fc at a concentration in the range of 0.15-5.3 μg/mL (preferably about 2.3-5.3 μg/mL). Coated wells are then washed to remove unbound ligand and seeded with stem cells in serum-free hematopoietic differentiation medium at a density of, for example, about 1000-4000 cells/well in a 96 well plate. In a preferred embodiment, the serum-free hematopoietic differentiation medium is a defined medium, such as, for example, Iscove's Modified Dulbecco's Medium with 20% bovine serum albumin, insulin, and transferrin serum substitute (IMDM+BIT). In a preferred embodiment, the seeded cells are cultured in the presence of growth factors that facilitate pro-T cell differentiation, such as, for example, Stem Cell Factor (SCF), FMS-like Tyrosine Kinase 3 Ligand (Flt3L), thrombopoietin (TPO) and Interleukin 7 (IL7). The seeded cells are cultured at an appropriate temperature, e.g., 37° C., and for a time sufficient to generate pro-T cells, such as, for example, 9-21 days (human) or 7-14 days (mouse). To confirm generation of pro-T cells, the cells cultured in the 2D system may be analyzed for one or more features indicative of pro-T cells, such as, for example, specific molecular markers.

In general, pro-T cell development in the thymus is characterized by four sequential stages commonly referred to as DN1, DN2, DN3 and DP (DN=double negative and DP=double positive for CD4 and CD8 expression). Murine pro-T cells can be tracked via expression of CD25 and CD44 on the cell surface progressing via successive double-negative (DN; CD4−CD8−) stages: DN1 (CD25−CD44+CD90−), DN2 (CD25+CD44+CD90+), DN3 (CD25+CD44−CD90+/−) and finally maturing to double-positive (DP; CD4+CD8+) and single-positive (SP; CD4+CD3+ or CD8+CD3+) T cells. Human pro-T cells can be tracked via expression of CD4 and CD8 on the cell surface progressing via successive double-negative (DN; CD4−CD8−) stages: CD7+CD34+ primitive progenitor T cells followed by CD7+ and/or CD34− and/or CD5+ and/or CD45RA+ pro-T cells and finally maturing to double-positive (DP; CD4+CD8+) and single-positive (SP; CD4+CD3+ or CD8+CD3+) T cells. In an embodiment, the method provided herein may be used to generate CD25+CD90+ murine pro-T cells. In an embodiment, the method provided herein may be used to generate CD7+ human pro-T cells.

Progenitor T Cells Generated Using the In Vitro Method Provided Herein

Pro-T cells generated using the method provided herein are provided. Preferably, the pro-T cells are human. In an embodiment, the human pro-T cells may be characterized phenotypically via expression of CD4 and CD8 on the cell surface progressing via successive double-negative (DN; CD4−CD8−) stages: CD7+CD34+ primitive progenitor T cells followed by CD7+ and/or CD34− and/or CD5+ and/or CD45RA+ pro-T cells and finally maturing to double-positive (DP; CD4+CD8+) and single-positive (SP; CD4+CD3+ or CD8+CD3+) T cells. In an embodiment, the human pro-T cells provided herein may be characterized by CD7 expression. In general, lymphoid cells may be identified by their small and round morphology and by blue colour in a Giemsa stain. In an embodiment, the pro-T cells provided herein may be functionally characterized. For example, CD7+ pro-T cell transplantation in vivo should result in the transplanted cells homing to the thymus, engrafting in the thymus, and then rapidly dividing to generate DP and SP T cells.

In an embodiment, the stem and/or progenitor cells are pluripotent stem cells, such as ESCs or iPSCs. In an embodiment, the stem and/or progenitor cells are HSPCs. For example, the HSPCs may be obtained from cord blood, peripheral blood or bone marrow or they may be derived in vitro from ESCs, iPSCs or other intermediate stem cells. In a preferred embodiment, the stem and/or progenitor cells are human cells.

In an embodiment, the pro-T cells generated using the method provided herein are autologous.

In an embodiment, the pro-T cells generated using the method provided herein are allogeneic.

It is contemplated that the allogeneic pro-T cells provided herein could be transferred to an irradiated subject in need of pro-T cells irrespective of major histocompatibility complex (MHC) disparities. Without being bound by theory, it is thought that pro-T cells, unlike mature T cells, do not cause graft versus host disease (GVHD), at least because pro-T cell precursors complete their differentiation in the thymus, where they become restricted to host MHC and yield T lymphocytes that are host tolerant. Thus, strict histocompatibility would not be required in therapeutic use of the pro-T cells provided herein.

The cells provided herein may be used, for example, to treat a subject in need of pro-T cells and/or more mature T cells. By "treat" we mean administering to the subject and effective amount of cells, as provided herein, under conditions suitable for increasing the number of T cells in the subject, which may result in prevention, inhibition and/or therapeutic treatment of a medical condition associated with insufficient T cells. By "effective amount" we mean a therapeutically effective amount such as, for example, the amount of cells that, upon administration to a subject, is sufficient to achieve the intended purpose (e.g., treatment). The amount may vary from one subject to another and may depend upon one or more factors, such as, for example, subject gender, age, body weight, subject's health history, and/or the underlying cause of the condition to be prevented, inhibited and/or treated.

For example, subjects afflicted with a medical condition causing or resulting in lymphopenia may benefit from administration of a pro-T transplant as described herein. For example, subjects who are post-chemotherapy and/or post-irradiation, such as those receiving treatment for cancer, subjects having HIV infection, partial thymectomy, autoimmune diseases, such as lupus or rheumatoid arthritis, or diabetes may benefit from administration of the pro-T cells provided herein. In an embodiment, the administered cells may be autologous. In an embodiment, the administered cells may be allogeneic. In an embodiment, the cells provided herein may be used to induce host tolerance upon organ transplant.

Kits for Generating Progenitor T Cells

The present disclosure contemplates kits for carrying out the methods provided herein. Such kits typically comprise two or more components required for generation of pro-T cells. Components of the kit include, but are not limited to, one or more of compounds, reagents, containers, equipment and instructions for using the kit. Accordingly, the methods described herein may be performed by utilizing pre-packaged kits provided herein.

In an embodiment, a kit for use to generate pro-T cells from PSCs or HSPCs in vitro is provided. The kit comprises DL4 and VCAM-1. In an embodiment, the DL4 is adsorbed or immobilized to a substrate. In an embodiment, the VCAM-1 is adsorbed or immobilized to a substrate. In an embodiment, the kit further comprises a hematopoietic differentiation medium, preferably comprising growth factors, such as SCF, Flt3L, IL7 and/or TPO, in hematopoietic amounts. For example, amounts the growth factors may be as follows: 10-50 ng/mL (mouse cultures) and about 100 ng/mL (human cultures). In some embodiments, instructions for use of the kit to generate pro-T cells from stem and/or progenitor cells, such as PSCs or HSPCs, in vitro are provided. The instructions may comprise one or more protocols for: preparing DL4 and, optionally, preparing VCAM-1 components; providing DL4 and/or VCAM-1 components to a culture system; culture conditions, such as time, temperature, and/or gas incubation concentrations; harvesting protocols; and protocols for identifying pro-T cells and, optionally, more mature T cells.

The kit may further include materials useful for conducting the present method such as, for example, culture plates, welled plates, petri dishes and the like.

Non-limiting embodiments are described by reference to the following examples which are not to be construed as limiting.

Example 1: Methods

In Example 1, the methods used in the subsequent Examples are described.

Fetal-Liver Isolation and HSPC Sorting.

Untimed pregnant (E13-14) female CD-1 mice were purchased from Charles River Laboratories (Wilmington, MA). Animal use and experimental protocols were approved by the University of Toronto Animal Care Committee in accordance with the Guidelines of the Canadian Council on Animal Care. Fetal livers were isolated from the decapitated mouse embryos (E14-15) using surgical forceps. The fetal livers were placed in Hank's Balanced Salt Solution (HBSS; Invitrogen, Carlsbad, CA) containing 2% fetal bovine serum (FBS; Invitrogen) (or HF) and disrupted by using a 16-gauge blunt-end needle (Stemcell Technologies). To obtain single cell suspension, cells were gently passed through a 21-gauge needle three times. Cells were spun down at 1500 rpm for 5 min at 4° C. and washed twice with HF. Subsequently, cells were subjected to two rounds of Ter119 depletion by EasySep™ magnetic sorting (Stemcell Technologies, Vancouver, BC, Canada) according to the manufacturer's instructions. Ter119− fetal liver cells were stained for HSPC sorting in ice cold HF at $1 \times 10^7$ cells/mL. Cells were blocked against non-specific binding with 1% anti-Fc receptor antibody (Fc-block, BD Biosciences, San Jose, CA) and stained with anti-Sca-1-PE and anti-cKit-APC (BD Biosciences, San Jose, CA) for 20 minutes on ice. Dead cells were excluded from live cell sorting using 7-aminoactinomycin D (7-AAD; Invitrogen). Cells were sorted at $1 \times 10^6$ cells/mL using either FACSAria™ II (Becton Dickinson), MoFlo® Astrios™ (Beckman Coulter) or MoFlo™ XDP flow cytometers (Beckman Coulter). Isotype controls and singly stained compensation controls were used to set threshold gates for sorting such that the negative controls contained 99.5% negative cells.

DL4-Fc Production and Coated DL4-Fc Plate Preparation.

Commercially available DL4-Fc was purchased and used for experiments from Sino Biologicals (Cedarlane Labs, Burlington, Ontario, Canada) or manufactured in-house as described below. DL4-Fc was diluted in chilled phosphate-buffered saline (PBS) at 10 μg/mL or 20 μL/well and 50 μL/well was coated in standard tissue-culture 96-well plates overnight at 4° C. Wells were washed once with PBS prior to seeding cells to remove any unbound ligand from the wells. For certain experiments, wells were also coated overnight with 50 μL/well PBS containing DL4-Fc and VCAM-1-Fc (R&D) or fibronectin (Sigma) at concentrations described herein.

Genetically engineered DL4-Fc was generated by fusing the coding sequence of the extracellular domain of murine Dll4 (amino acid residues 1-529 of SEQ ID NO: 1) to the Fc portion of human IgG1 (including the hinge region) and inserting it into pIRESpuro2 mammalian expression plasmid (Clontech, Mountainview, CA). HEK-293T cells were transfected using standard $CaPO_4$ transfection methods and cells were selected with stably integrated plasmid based on their resistance to 2 μg/mL of puromycin added to the medium, DMEM [supplemented with 10% (v/v) FBS, 2 mM Glutamax, Penicillin (100 U/ml)/Streptomycin (100 mg/ml) (all products of Thermo Fisher Scientific, Rockford, IL), 2 mM 2-mercaptoethanol (Sigma-Aldrich, St. Louis, MI)]. Cells were expanded and transferred to grow in FreeStyle™ 293 expression media (Thermo Fisher Scientific). DL4-Fc fusion protein secreted into the media was purified using HiTrap™ Protein G affinity column (GE Healthcare Life Sciences, Marlborough, MA) attached to the AKTAprime Plus™ (GE Health) automated chromatography system. For certain experiments, DL1-Fc was produced as previously described[8].

Sorted HSPC Seeding and In Vitro Culture.

Sorted sca1+ckit+ HSPCs were cultured at 1000 cells/well (corresponding to $3.1 \times 10^3$ cells/cm$^2$) in DL4-coated 96-well plates in serum-free Iscove modified Dulbecco medium (Gibco, Rockville, MD) with 20% bovine serum albumin, insulin, and transferrin serum substitute (BIT; Stemcell Technologies), 1% GlutaMAX™ (Gibco) and 1 μg/mL low-density lipoproteins (Calbiochem, La Jolla, CA) [IMDM+BIT]. For positive control cultures, OP9 serum medium was used, composed of αMEM medium (Gibco) and 16% FBS (Hyclone™, GE Health). Serum-free αMEM+BIT medium was prepared exactly as IMDM+BIT medium except using αMEM (Gibco) as the base medium. OP9 serum medium, αMEM+BIT or IMDM+BIT serum free medium was added at 200 μL/well supplemented with 25 ng/mL Stem Cell Factor (SCF; R&D Systems, Minneapolis, MN), 5 ng/mL FMS-like Tyrosine Kinase 3 Ligand (Flt3L; R&D Systems) and 1 ng/mL Interleukin-7 (IL-7; R&D Systems) with a 50% medium exchange step at day 4 containing 2-fold concentrated cytokines as described previously[9]. Design of Experiment (DOE) in silico modeling was performed using Design-Expert® (v10) using response surface method to investigate the combinatorial desirability of different concentrations of SCF, Flt3L and IL-7 for maximizing DN3 T-cell yield and minimizing the volume of IMDM+BIT medium. After DOE optimization, IMDM+BIT serum-free medium was added at 50 μL/well supplemented with 50 ng/mL SCF (R&D Systems), 10 ng/mL Flt3L (R&D Systems) and 10 ng/mL IL-7 (R&D Systems) unless described otherwise in the text with no medium exchange for the length of the assay. For the candidate factor screening in serum-free IMDM+BIT medium, the following proteins or small molecules were used at the concentrations listed: JAK inhibitor I (50 nM; EMD Millipore), IL-11 (10, 50, and 100 ng/mL; R&D Systems), IL-6 (10, 50, and 100 ng/mL; R&D Systems), IL-6R (100 ng/mL; R&D Systems), Ccl25 (1.5 μg/mL; R&D Systems), IL-7 (50, 100, and 200 ng/mL; R&D Systems), SDF1α (Cxcl12; 200 ng/mL; R&D Systems), and Leukemia Inhibitory Factor (LIF; 0.1, 1, and 10 ng/mL; EMD Millipore).

For human HSPC culture, umbilical cord blood samples were collected from consenting donors according to ethically approved procedures at Mount Sinai Hospital. CD34+ cells were isolated from the red blood cell (RBC)-lysed cord blood fraction using the EasySep™ Human CD34 Positive Selection Kit (Stemcell Technologies) according to the manufacturer's instructions. Flow cytometry was performed after every enrichment to ensure CD34 frequencies were greater than 95%. CD34+ HSPCs were cultured for 14 days on DL4 and VCAM-1 coated 96-well plates at higher seeding densities of 12,500 HSPCs/cm$^2$ (corresponding to 4000 cells/well). One complete medium exchange was performed at day 7 of culture and cells were returned to the same DL4 and VCAM-1 coated plates. For certain experiments, DL4-Fc was coated alone or with RetroNectin® (Takara Shuzo) or fibronectin (Sigma Aldrich) as described in the text. CD34+ cells were cultured in serum-free Iscove modified Dulbecco medium (Gibco) with 20% bovine serum albumin, insulin, and transferrin serum substitute (BIT; Stemcell Technologies), 1% GlutaMAX™ (Gibco) and 1 µg/mL low-density lipoproteins (Calbiochem). The medium was added at 50 µL/well supplemented with 100 ng/mL SCF (R&D Systems, Minneapolis, MN), 100 ng/mL Flt3L (R&D Systems), 100 ng/mL Tpo (R&D Systems) and 100 ng/mL IL-7 (R&D Systems).

Flow Cytometry.

Surface marker staining was performed with conjugated rat anti-mouse antibodies (BD Biosciences, San Jose, CA, Table 1). All samples were analyzed on a FACSCanto™ or FACS LSRFortessa™ flow cytometer (BD Biosciences). At day 7 of culture, cells were lifted off the plate with multiple HF rinses, stained at 1:400 dilution with antibodies against CD45, CD25, CD44, CD90, CD11b and CD19 for 20 minutes on ice. Human progenitor T-cells were stained at 1:100 dilution with antibodies against CD34, CD7, CD5 and CD45RA. Integrin expression was analyzed using antibodies against α4, β1, and β7 integrin subunits on Sca-1+cKit+ mouse HSPCs and CD34+ human umbilical blood cells. For intracellular cytokine staining, splenocytes were harvested, washed, and stained with fluorochrome-conjugated anti-human antibodies to CD45 and CD3 and subsequently fixed and permeabilized using the Cytofix/Cytoperm™ kit (BD Biosciences) with IL-2, IFN-γ and TNF-α-specific antibodies. All mouse anti-human antibodies were purchased as described in Table 1. Cells were washed twice with HF and dead cells were excluded using 7-AAD (Life Technologies) at 1:1000 dilution. Flow data was analyzed and batch processed using FlowJo® software and further analyzed in Python (version 2.7.10).

NIH3T3 Luciferase Assay for Measuring Notch Activation.

NIH3T3 cells were seeded at 125,000 cells/well in a 6-well plate on the previous day and transiently transfected overnight with Notch1, CBF1-Firefly and constitutively active *Renilla* plasmids using FuGENE® HD transfection reagent (Promega Corporation, Madison WI USA) as per the manufacturer's instructions. Transfected NIH3T3 cells were either seeded on DL4-coated plates or in DL4-conjugated MC for 24 hours prior to measuring Firefly activation normalized to *Renilla* expression using the dual-luciferase reporter assay system (Promega Corporation, Madison WI USA) according to the manufacturer's instructions.

Live Imaging

Sorted Sca-1+cKit+ HSPCs were seeded at low density (200 cells/well) into triplicate wells of 96-well plates coated with different substrates. After 6 days of culture, cells were stained with conjugated antibodies for CD25-APC and CD44-PE (1:500 dilution) at 37° C. for 1 hour. Live cell imaging was then performed without washing on the AxioObserver Z1 (Zeiss) platform in 5% CO2 and 37° C. controlled conditions. Brightfield images were captured at 5-minute (or 10-minute) intervals over 24 hours using a 10×0.3 NA air objective. To minimize phototoxicity and photobleaching, images in the fluorescent APC and PE channels were acquired at longer 30-minute (or 60-minute) intervals. Image acquisition and processing was performed using ZEN 2012 blue edition software (Zeiss). Manual tracking was performed using Image-J software. Cells were tracked within 3 unique DL4 only wells and 3 unique DL4+VCAM-1 wells. Manual tracking was performed on 43 cells in the DL4 only condition (15, 10 and 18 cells per well) and 69 cells in DL4+VCAM-1 condition (30, 14 and 25 cells per well).

Quantitative Real-Time PCR

TABLE 1

| Antibodies | | | | |
|---|---|---|---|---|
| Antibody | Reactivity | Fluorophore | Company | Catalog Number |
| CD25 | Mouse | APC | BD Biosciences | 557192 |
| CD44 | Mouse | PE | BD Biosciences | 553134 |
| CD45 | Mouse | APCCy7 | BD Biosciences | 557659 |
| CD90.2 | Mouse | V450 | BD Biosciences | 561643 |
| CD19 | Mouse | PECy7 | BD Biosciences | 552854 |
| CD11b | Mouse | FITC | BD Biosciences | 557396 |
| Sca-1 | Mouse | PE | BD Biosciences | 553108 |
| cKit | Mouse | APC | BD Biosciences | 553356 |
| CD49d (α4) | Mouse | PE | BioLegend | 103607 |
| CD29 (β1) | Mouse | APC | BioLegend | 102215 |
| β7 | Mouse | APC | BioLegend | 321207 |
| 7-AAD | Mouse/Human | PerCP-Cy5-5 | Life Technologies | A1310 |
| CD45 | Human | APCCy7 | BD Biosciences | 557833 |
| CD7 | Human | APC | BD Biosciences | 561604 |
| CD5 | Human | PECy7 | eBioscience | 25-0059-42 |
| CD34 | Human | PE | BD Biosciences | 555822 |
| CD34 | Human | PECy7 | BD Biosciences | 560710 |
| CD45RA | Human | FITC | BioLegend | 304106 |
| CD8 | Human | PE | BD Biosciences | 555367 |
| CD3 | Human | FITC | BD Biosciences | 555332 |
| CD1a | Human | APC | BD Biosciences | 559775 |
| CD4 | Human | PECy7 | BD Biosciences | 557852 |
| CD7 | Human | Alexa Fluor 700 | BD Biosciences | 561603 |
| CD49d (α4) | Human | APC | BD Biosciences | 561892 |
| CD29 (β1) | Human | PE | BD Biosciences | 561795 |
| β7 | Human | PE | BD Bioscience | 555945 |
| IFN-α | Human | PE | BD Biosciences | 554552 |
| TNF-α | Human | PECy7 | BD Biosciences | 557647 |
| IL-2 | Human | APC | BD Biosciences | 561054 |

Sorted Sca-1+cKit+ murine HSPCs were seeded on no coating, 10 μg/mL DL4, 2.32 μg/mL VCAM-1, and DL4+VCAM-1 at 20,000 cells/well in 96-well plates and were collected at 24 and 48 hours of culture using multiple PBS rinses. CD34+ human umbilical blood cells were seeded in the same conditions and were collected after 24, 48, and 96 hours of culture. Cells were lysed and RNA was isolated using the PureLink™ RNA Micro Kit (Invitrogen) according to the manufacturer's protocol. RNA was converted to cDNA using SuperScript™ III Reverse Transcriptase (Invitrogen) according to the manufacturer's protocol, and amplified together with respective primers in FastStart SYBR Green Master Mix (Roche). Thermocycling and quantification was performed using the QuantStudio™ 6 Flex (Applied Biosystems). Relative expression of individual genes was calculated by the delta cycle threshold (Δ-Ct) method with the expression of β-actin as an internal reference. PCR primer sequences are available in Table 2.

TABLE 2 qRT-PCR Primer Sequences

| Target | Species | Forward Primer | Reverse Primer |
|---|---|---|---|
| β-actin | Mouse | GAAATCGTGCGTGACATCAAAG (SEQ ID NO: 6) | TGTAGTTTCATGGATGCCACAG (SEQ ID NO: 7) |
| Bcl11b | Mouse | GGGCGATGCCAGAATAGAT (SEQ ID NO: 8) | GGTAGCCTCCACATGGTCAG (SEQ ID NO: 9) |
| Deltex | Mouse | GAGGATGTGGTTCGGAGGTA (SEQ ID NO: 10) | CCCTCATAGCCAGATGCTGT (SEQ ID NO: 11) |
| E2a | Mouse | TTTGACCCTAGCCGGACATAC (SEQ ID NO: 12) | GCATAGGCATTCCGCTCAC (SEQ ID NO: 13) |
| Gata3 | Mouse | CTCGGCCATTCGTACATGGAA (SEQ ID NO: 14) | GGATACCTCTGCACCGTAGC (SEQ ID NO: 15) |
| Hes1 | Mouse | TCAACACGACACCGGACAAAC (SEQ ID NO: 16) | ATGCCGGGAGCTATCTTTCTT (SEQ ID NO: 17) |
| Notch1 | Mouse | CCCTTGCTCTGCCTAACGC (SEQ ID NO: 18) | GGAGTCCTGGCATCGTTGG (SEQ ID NO: 19) |
| Pu.1 | Mouse | ATGTTACAGGCGTGCAAAATG (SEQ ID NO: 20) | TGATCGCTATGGCTTTCTCCA (SEQ ID NO: 21) |
| Tcf7 | Mouse | AGCTTTCTCCACTCTACGAACA (SEQ ID NO: 22) | AATCAGAGAGATCGGGGGTC (SEQ ID NO: 23) |
| β-actin | Human | CATGTACGTTGCTATCCAGGC (SEQ ID NO: 24) | CTCCTTAATGTCACGCACGAT (SEQ ID NO: 25) |
| Bcl11b | Human | TCCAGCTACATTTGCACAACA (SEQ ID NO: 26) | GCTCCAGGTAGATGCGGAAG (SEQ ID NO: 27) |
| Deltex | Human | ATCGGAGAAGGCTCTACAGG (SEQ ID NO: 28) | CGTCTGGCCTCCTTTCTAACT (SEQ ID NO: 29) |
| E2a | Human | CCGACTCCTACAGTGGGCTA (SEQ ID NO: 30) | CGCTGACGTGTTCTCCTCG (SEQ ID NO: 31) |
| Gata3 | Human | GTTGGCCTAAGGTGGTTGTG (SEQ ID NO: 32) | ACAGGCTGCAGGAATAGGGA (SEQ ID NO: 33) |
| Hes1 | Human | CCTGTCATCCCCGTCTACAC (SEQ ID NO: 34) | CACATGGAGTCCGCCGTAA (SEQ ID NO: 35) |
| Notch1 | Human | GAGGCGTGGCAGACTATGC (SEQ ID NO: 36) | CTTGTACTCCGTCAGCGTGA (SEQ ID NO: 37) |
| Pu.1 | Human | TGCAATGTCAAGGGAGGGGG (SEQ ID NO: 38) | AAACCCTTCCATTTTGCACGC (SEQ ID NO: 39) |
| Tcf7 | Human | TGCACATGCAGCTATACCCAG (SEQ ID NO: 40) | TGGTGGATTCTTGGTGCTTTTC (SEQ ID NO: 41) |

Mice.

hSIRPα$^{tg}$ RAG2$^{-/-}$ γc$^{-/-}$ (SRG) mice were purchased from The Jackson Laboratory (Bar Harbor, ME) and housed and bred in a pathogen-free facility. All animal procedures were approved by the Sunnybrook Health Sciences Centre Animal Care Committee.

Fed-Batch Bioreactor Expansion Culture of Human CD34+ HSPCs

Umbilical cord blood samples were collected from consenting donors according to ethically approved procedures at Mt. Sinai Hospital (Toronto, ON, Canada). Cells were red blood cell (RBC) depleted as previously described[10], using HetaSep (StemCell Technologies). CD34+ progenitor cells were selected with the EasySep system using a human CD34+ enrichment kit (StemCell Technologies), according to the manufacturer's protocol. Freshly isolated CD34+ cells were seeded at a density of 1×10⁵ total cells/mL. Cells were seeded in StemSpan-ACF medium (StemCell Technologies), supplemented with 100 ng/mL Stem Cell Factor (SCF, R&D Systems or CellGenix), 100 ng/mL FMS-like Trysine Kinase 3 Ligand (Flt3L, R&D Systems or CellGenix), 50 ng/mL Thrombopoietin (TPO, R&D Systems or CellGenix), 2 mM GlutaMAX (GIBCO) and/or 500 nM UM729 small molecule. Cells were cultured for 12 days with minimal manual manipulation during the culture period, as previously described[11].

Cells were harvested from either fed-batch or fed-batch+ UM729 at day 12 and sorted for CD34+ and CD34− populations. Sorted CD34+ and CD34− cells from both culture methods were seeded along with thawed unexpanded day 0 CD34+ HSPCs at 4000 cells/96-well coated overnight with 20 μg/mL DL4 and 2.3 μg/mL VCAM-1 in serum-free IMDM+BIT medium containing 100 ng/mL SCF, Tpo, Flt3L and IL-7. Cultures were fed once 7 days later and harvested 14 days later for FACS analysis of lymphoid and myeloid lineage cell surface markers.

Engraftment of Human Progenitor T-Cells into Immunodeficient Mice.

Human CD34⁺ HSPCs were cultured for 14 days in an engineered thymic niche. CD7⁺ progenitor T-cells were sorted, resuspended in a mixture of PBS containing recombinant human interleukin 7 (rhIL-7; 0.5 μg) with an IL-7 antibody M25 (2.5 μg), and injected intrahepatically into 2-5 day old SRG neonatal mice. Each mouse received 4×10⁵ CD7⁺ progenitor T-cells in a 30 μl total volume. As controls, mice were injected with CD7⁺ cells from a day 14 HSPC/OP9DL4 co-culture, as previously described[2]. Mice were boosted intraperitoneally with an IL-7/M25 mixture every 4 days. Thymus, spleen, and peripheral blood were harvested at 4-12 weeks after intrahepatic transplant and cells were analyzed with CD3, CD1a, CD7, CD5, CD4, CD8 and CD45 anti-human antibodies. For intracellular cytokine staining, splenocytes were harvested from SRG mice 10-12 weeks after intrahepatic injection of OP9-DL4 or DL4-VCAM-derived CD7+ cells. Cells were seeded at a density of 1×10⁵ cells/well in OP9-media, and were incubated for 6 hours with 50 ng/mL phorbol 12-myristate 13-acetate (PMA; Sigma Aldrich), 500 ng/mL ionomycin (Sigma Aldrich) and 3 μg/mL Brefeldin A (eBioscience). Cells were washed with PBS post-stimulation and stained for intracellular cytokine staining as described above.

Generation of Human Pluripotent Stem Cell (hPSC)-Derived Hemogenic Endothelium.

Aggrewells™ (24 well, StemCell Technologies) were manufactured in-house using 400 μm polydimethylsiloxane inserts cast from a silicone master mold and sterilized as previously described (Ungrin et al., 2008). For hemogenic endothelium differentiation, hPSCs on MEFs were dissociated with 5 minute TrypLE™ Express treatment and plated onto Geltrex® (diluted 1:50) or Matrigel® (diluted 1:30) coated 6-well plates at a split ratio of 1:3 for 48 hours of MEF depletion. The MEF-depleted hPSCs were treated with TrypLE™ Express followed by scraping and mechanical dissociation. Single cell suspensions were transferred to Aggrewell™ plates in hemogenic endothelium inducing medium supplemented with ROCK inhibitor Y-27632 (RI) (1:1000, Sigma Aldrich), and the plates were then centrifuged at 1500 rpm for 5 minutes to form cell aggregates in individual microwells. Hemogenic endothelium-inducing media comprised of BMP4 (40 ng/ml, R&D), VEGF (50 ng/ml, R&D), SCF (40 ng/ml, R&D), and bFGF (5 ng/ml, Peprotech). Base media comprised of StemPro®-34 (Invitrogen), ascorbic acid (50 μg/ml; Sigma), L-glutamine (1% v/v, Invitrogen), penicillin/streptomycin (1% v/v), 1-monothioglycerol (4×10⁻⁴ M; Sigma), and transferrin (150 μg/ml; Roche).

At day 6 of culture, cells were harvested and dissociated using TrypLE™ Express. CD34+ cells were enriched using an EasySep™ Human CD34 Positive Selection Kit (Stem Cell Technologies). Cells were characterized for CD34+ expression post-selection and seeded on DL4-Fc and VCAM-Fc coated plates for two weeks in serum-free IMDM base medium (Gibco, Rockville, MD) containing BIT 9500 Serum Substitute (20% v/v, Stem Cell Technologies), penicillin/streptomycin (1% v/v), GlutaMAX™ (1% v/v, Gibco), low-density lipoproteins (1 μg/mL, Calbiochem, La Jolla, CA) and 100 ng/mL each of SCF, Flt3L, Tpo and IL-7 (R&D). Cells were re-fed once at day 7 of culture and harvested for analysis via flow cytometry at the end of 14 days for progenitor T cell surface markers.

Scaled Progenitor T Cell Differentiation

Umbilical-cord blood derived CD34+ cells were differentiated in OP9DL4 stromal co-cultures and compared with defined serum-free differentiation cultures in 96-well plates or 6-well plates coated with DL4+VCAM-1. Half of a 96-well plate (15.4 cm²) was compared with two wells in a 6-well plate (19.0 cm²) or 12 cm×2 cm clipped surface area in an adherent culture bioreactor bag (24 cm²). Frequencies of CD7+, CD7+CD34+, CD7+CD34− and CD7+CD5+ progenitor T-cells were analyzed after 14 days.

Figure 2A:
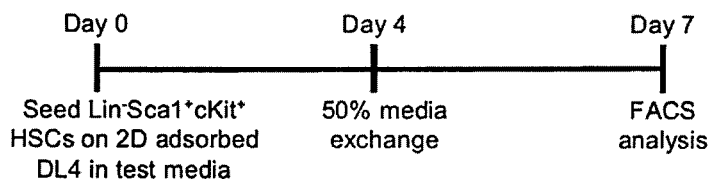
FIGS. 2a-o depict identification of a defined, serum-free medium for efficient T-cell differentiation.
Figure 2B:
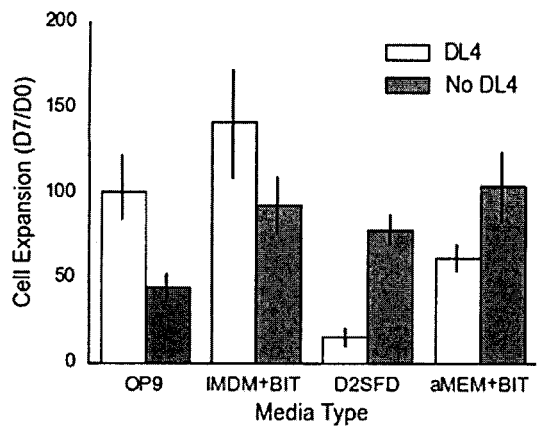
FIG. 2b: Graph depicting total fold expansion on day 7 of CD45+7AAD− live cells over input sorted HSPCs on day 0 in the presence or absence of 2D coated DL4.
Figure 2C:
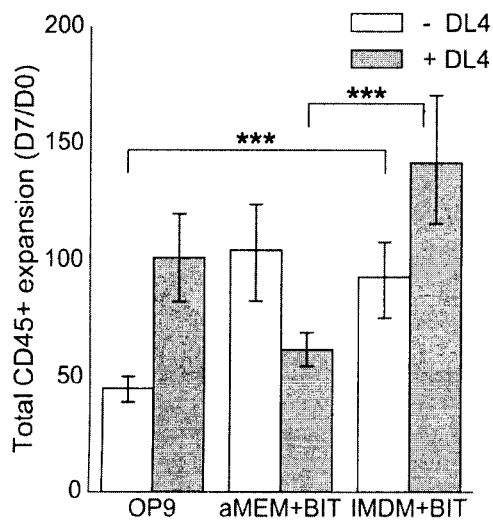
FIG. 2c: Graph depicting total fold expansion on day 7 of CD45+7AAD− live cells over input sorted HSPCs on day 0 in the presence or absence of 10 μg/mL adsorbed DL4 in OP9 serum medium (αMEM+16% FBS) vs. serum-free media compositions (αMEM+BIT and IMDM+BIT) (n=3); all media compositions contained the same amount of cytokines (25 ng/mL SCF, 5 ng/mL Flt3L and 1 ng/mL IL-7 in 200 μL medium/well) with a 50% medium exchange step at day 4.
Figure 2D:
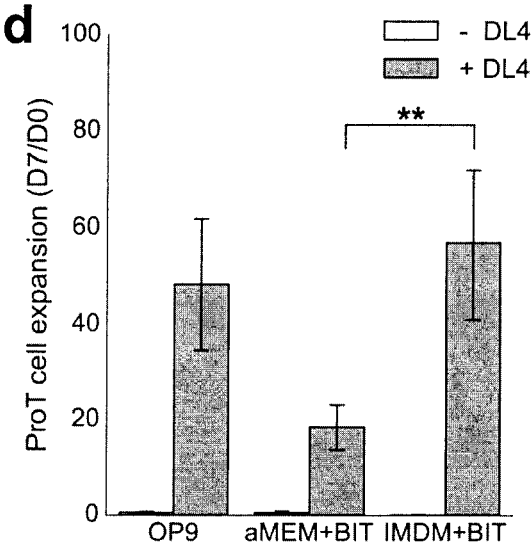
FIG. 2d: Graph depicting CD25+CD90+ progenitor T (proT) cell expansion on day 7 over input sorted HSPCs on day 0 in the different media compositions in the presence or absence of DL4 (n=3) (data in FIGS. 2c and 2d represent mean±95% Cl for n=3 biological replicates. *P<0.05; P<0.01; *P<0.001).
Figure 2E:
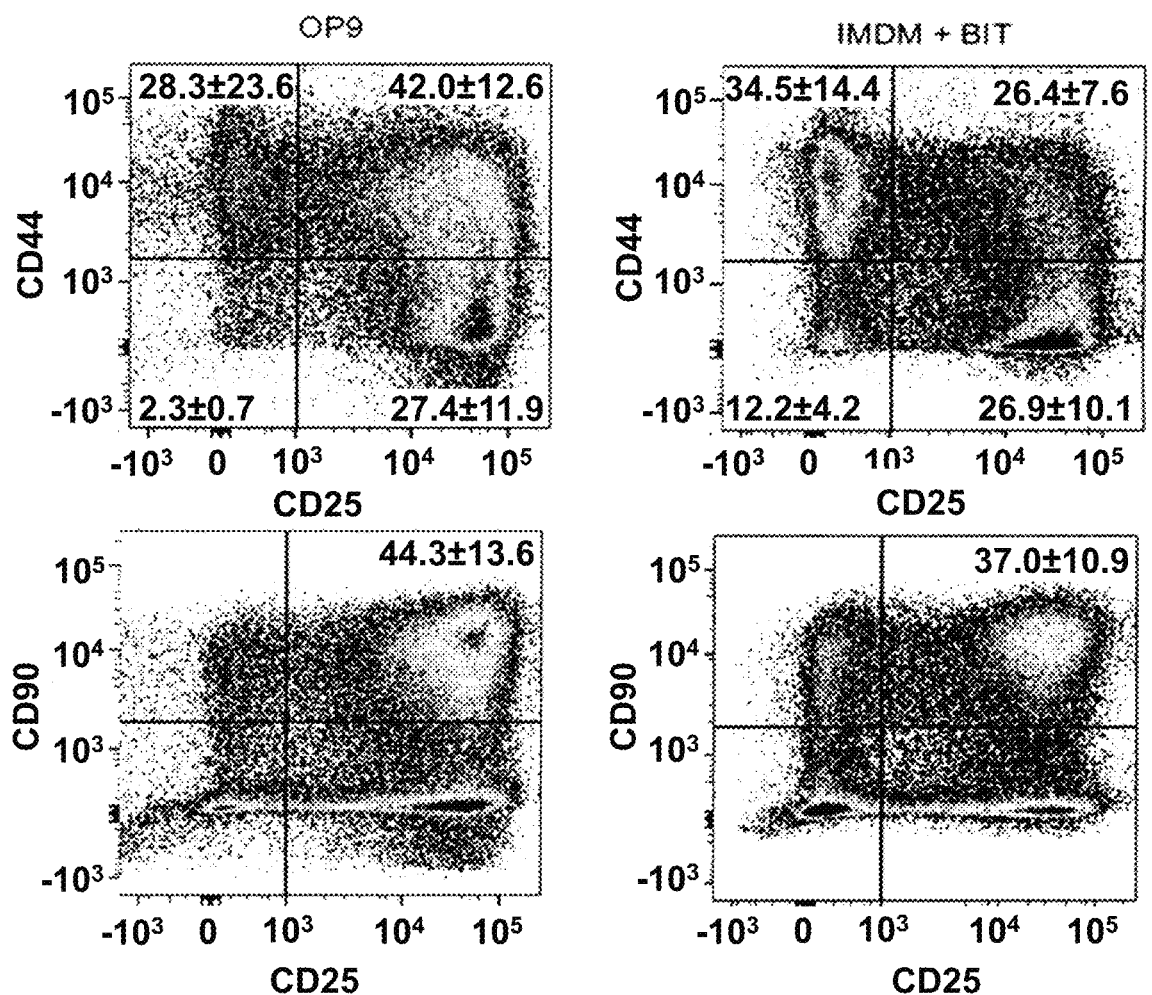
FIG. 2e: Representative flow plots for serum (OP9 medium; αMEM+16% FBS) medium vs. serum-free (IMDM+BIT) medium gated on CD45+7AAD− expression; top row shows CD25 vs. CD44 expression while bottom row shows CD25 vs. CD90 surface marker expression; error bars, s.d. (n=3).
Figures 2F, 2G:
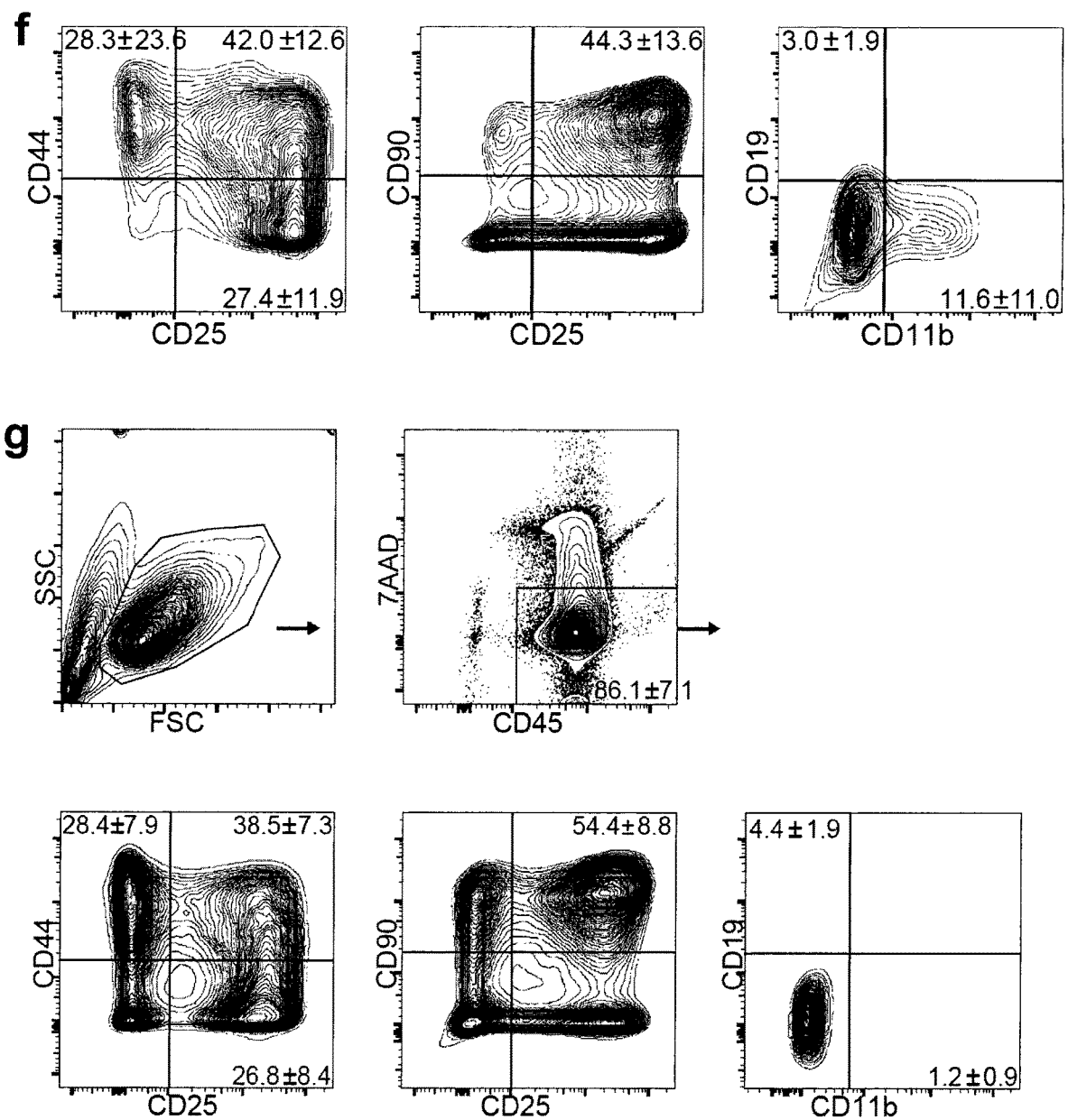
FIG. 2f: Representative flow cytometry plots of baseline positive control differentiation was quantified in OP9 serum medium (n=3).
FIG. 2g: Representative flow cytometry plots on day 7 of differentiation was quantified on 10 μg/mL adsorbed DL4 ligand in IMDM+BIT serum-free medium; data represent mean±standard deviation for n=3 biological replicates.
Figure 2H:
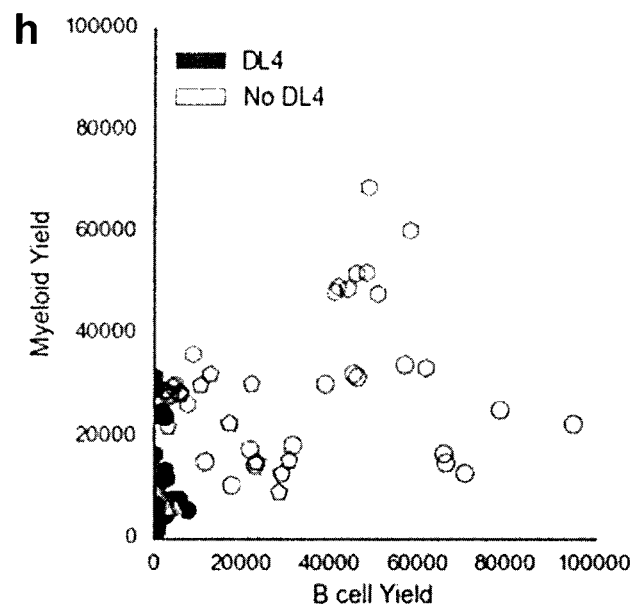
FIG. 2h: Graph depicting CD11 b+ myeloid cell yield vs. CD19+ progenitor B cell yield in different serum-free media compositions (marker shape corresponds to media condition from subpanel (i)) compared to serum media control; filled markers are indicative of 2D coated DL4 conditions and empty markers indicate no DL4 conditions. αMEM+BIT serum-free media produced the best myeloid and B cell yields comparable to serum media control.
Figures 3A, 3B, 3C, 3D:
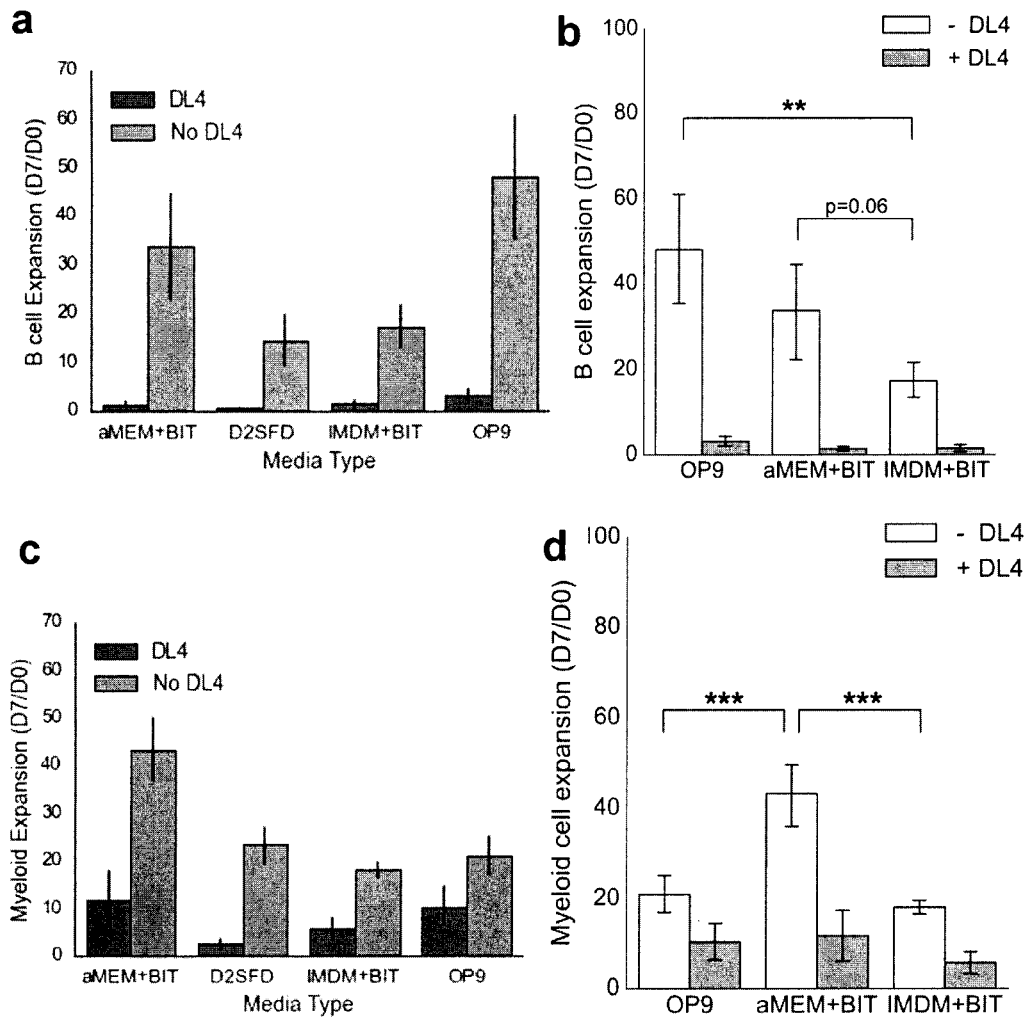
FIGS. 3a-d depict quantification of myeloid and B cell expansion in different serum-free media compositions compared to serum OP9 media control.

Example 2: Identification of a Defined, Serum-Free Medium for Efficient T-Cell Differentiation Progenitor T cell development in the thymus is characterized by four sequential stages commonly referred to as DN1, DN2, DN3 and DP (DN=double negative and DP=double positive for CD4 and CD8 expression). An ideal defined progenitor T cell differentiation assay should aim to support the expansion of DN3 T cells that are exclusively committed to the T lymphoid lineage. Additionally, CD90 must be upregulated on DN2 and DN3 T cells and co-expressed with CD25 to confirm their progenitor T cell identity. Conventional in vitro T cell differentiation is carried out on an OP9 stromal feeder layer in serum-containing medium. The obvious first step in developing a defined assay for T cell differentiation is to establish conditions that eliminate the requirements for both serum and feeders. To replace the OP9 feeder layer, DL4-Fc protein was generated and the purity and functionality of the ligand to bind DN T cells and not DP T cells was verified, as these cell types differentially express the Notch-1 receptor (FIGS. 1a-c). Next, three different serum-free medium compositions were tested for T cell differentiation capacity using E13.5 mouse fetal-liver derived sorted sca1+ckit+ HSPCs seeded on adsorbed DL4-Fc ligand. Assay development was performed with murine HSPCs with the aim to subsequently translate the system to clinically-relevant human progenitor T cell generation. The IMDM+BIT and D2SFD medium types were chosen based on previous experience with scalable human umbilical cord blood-derived HSPC expansion and serum-free pluripotent stem cell-derived mesoderm differentiation[12,13]. Cultures were re-fed after four days and analyzed for progenitor T cell surface markers after seven days (FIG. 2a). Parallel cultures were carried out on untreated surfaces (negative control) and OP9-DL4 stromal co-culture (positive control based on which SCF, Flt3L and IL-7 supplementation concentrations were determined[9]. In the absence of Notch ligand DL4-Fc, all three serum-free media gave rise to equivalent live blood cell (CD45+ 7AAD−) expansion levels that, unexpectedly, were significantly higher than the serum-containing medium positive control (OP9 stromal medium; αMEM+16% FBS) (FIGS. 2b,c). On DL4-Fc treated surfaces, IMDM+BIT serum-free cultures generated equivalent levels of CD45+ blood cells as the OP9 medium positive control cultures, and significantly higher levels of CD45+ cells than the other serum-free media tested (FIGS. 2b,c). Looking closely at the DN progenitor T cell subsets that differentiate sequentially in the thymus, IMDM+BIT medium gave rise to DN1, DN2 and DN3 T cell subsets as well as significantly higher CD25+ CD90+co-expression, indicative of progenitor T cells (FIGS. 2d-g). The level of lineage skewing to non-T cell fates was also quantified in the absence of Notch ligand in order to assess the default cell differentiation supported by all medium types. In the absence of DL4, αMEM+BIT serum-free media generated the maximum yield of CD11b+ myeloid cells and CD19+ B cells which was significantly higher (FIG. 2h; FIGS. 3a,b). D2SFD and IMDM+BIT media showed minimal amounts of both myeloid and B lineage skewing in the absence of DL4 ligand making them better progenitor T cell media candidates moving forward. Even in the presence of DL4 ligand, αMEM+BIT showed myeloid cell expansion comparable to OP9 medium (FIGS. 3c,d).

Figure 2I:
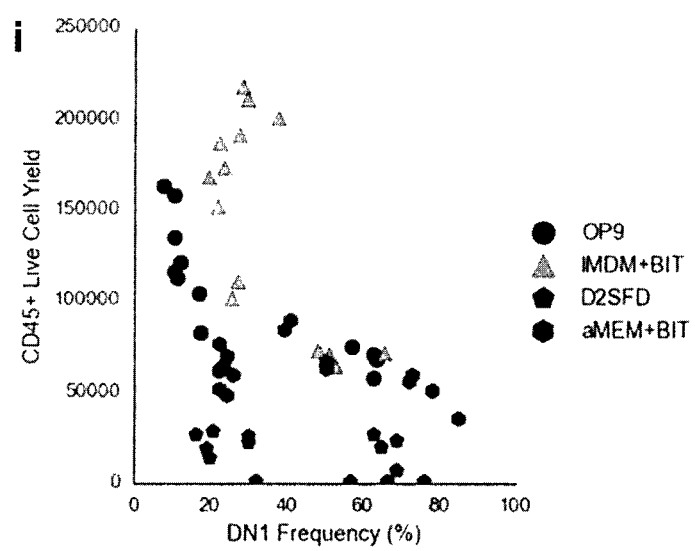
FIG. 2i: Graph depicting quantification of total CD45+ 7AAD− live cell yield at day 7 vs. frequency of DN1 (CD25−CD44+CD45+) progenitor T cells in different serum-free media compositions compared to serum media control.
Figures 2J, 2K, 2L, 2M, 2N, 2O:
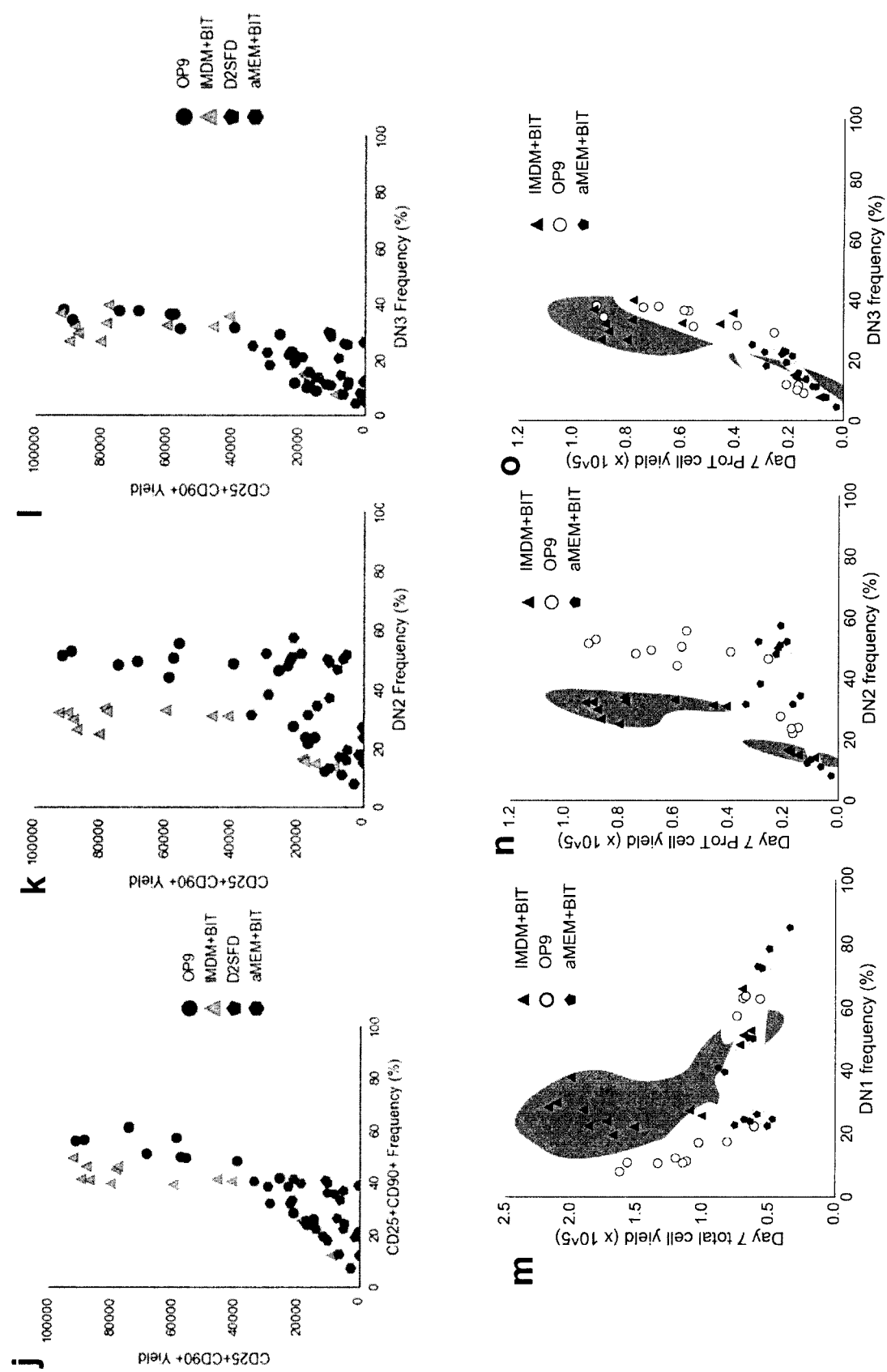
FIG. 2j: Graph depicting quantification of yield of CD25+ CD90+ vs. frequency of CD25+CD90+ progenitor T cells at day 7 of differentiation in different serum-free media compositions; IMDM+BIT showed comparable yield vs. frequency to the serum OP9 media control.
FIG. 2k: Graph depicting quantification of yield of CD25+ CD90+ progenitor T cells at day 7 vs. frequency of DN2 (CD25+CD44+CD45+) progenitor T cells.
FIG. 2l: frequency of DN3 (CD25+CD44−CD45+) committed progenitor T cells in different serum-free media compositions compared to serum media control.
FIG. 2m: Graph depicting quantification of total CD45+ 7AAD− live cell yield at day 7 vs. frequency of DN1 (CD25−CD44+CD45+) progenitor T cells in OP9 serum medium (αMEM+16% FBS) vs. serum-free media compositions (αMEM+BIT and IMDM+BIT).
FIG. 2n: Graph depicting quantification of yield of CD25+CD90+ proT cells at day 7 vs. frequency of DN2 (CD25+CD44+CD45+) cells in different serum-free media compositions compared to OP9 serum medium control.

Next, each medium was evaluated for progenitor T cell differentiation potential by quantifying the frequency of each DN subset and its contribution to the live cell yield. Of the serum-free medium candidates, IMDM+BIT medium retained the lowest frequencies of DN1 cells after 7 days of differentiation, comparable to the OP9 stromal medium control (FIG. 2i). In addition, IMDM+BIT also produced CD25+CD90+ cells at similar frequencies and yields to OP9 stromal medium control and significantly higher than other serum-free medium types (FIG. 2j). The individual contribution of DN2 and DN3 cells to the CD25+CD90+ compartment was then further examined. IMDM+BIT medium had lower DN2 contribution by frequency to the CD25+ CD90+ compartment than the OP9 stromal medium control although contribution to overall CD25+CD90+ yield was comparable to OP9 and significantly higher than other medium types (FIG. 2k). The T lineage-committed DN3 frequency and yield was comparable between IMDM+BIT and OP9 stromal medium and significantly higher than all other serum-free medium types (FIG. 2l). Higher variability in committed DN3 cells that co-expressed CD90 was also observed for DL4-treated surfaces with OP9 serum medium in comparison with IMDM+BIT serum-free medium (FIG. 2m-o). This suggests that IMDM+BIT medium promotes the proliferation of the primitive DN1 T cell compartment and reduces the frequency of cells in the DN2 stage to promote the expansion of DN3 T cells at levels similar to OP9 medium. Therefore, subsequent optimization of key assay design criteria was performed with IMDM+BIT serum-free medium.

Example 3: Optimization of Key Assay Design Criteria to Engineer the Thymic Niche The next step in assay development was to evaluate the effects of varying key culture parameters on in vitro T cell development. Seeding density, DL4 ligand concentration and presentation, and medium utilization were optimized in order to build a strategy to increase the robustness, reproducibility and yield of T cell production in the system.

First, the cell seeding density of sorted sca1+ckit+ HSPCs was modulated on 10 μg/mL adsorbed DL4 ligand in serum-free IMDM+BIT medium. At cell densities below 1000 cells/well (3125 cells/cm$^2$), high variability in the total cell expansion was observed (FIG. 4a). Total cell expansion was also significantly lower at cell densities above $3.1 \times 10^3$ cells/cm$^2$ (FIG. 4a). This may be due to the inherent variability in the HSPC compartment and further purifying the input cell source may eliminate this variability. However, at seeding densities of 1000 cells/well and higher, the variability of the total fold expansion was minimized. No significant differences in the DN subset frequencies were observed between the input cell densities tested (FIG. 5a). Alternate myeloid and B cell fate skewing was also minimal with 1000 cells/well (3125 cells/cm$^2$) input density (FIG. 5a). It was also observed that increasing seeding densities above 1000 cells/wells resulted in decreasing cell expansion. Therefore, for subsequent assay optimization 1000 HSPCs per well (or 3125 cells per cm$^2$) was selected as the input cell seeding density.

Next, the concentration of adsorbed DL4 ligand in the assay was varied to determine the minimum concentration of Notch ligand needed for robust T cell differentiation. 7.5 μg/mL DL4 was the minimum concentration that supported the generation of T lineage-committed DN3 cells at levels equivalent to the standard 10 μg/mL DL4 condition after 7 days of culture (FIG. 4b). Additionally, the frequency of DN1 cells decreased while DN2, DN3 and CD25+CD90+ co-expression increased with higher concentrations of adsorbed DL4 ligand further validating the role of Notch activation in promoting T cell development. Based on these results, a concentration of 10 μg/mL adsorbed DL4 was set for subsequent experiments. The use of Delta-like-1 (DL1) as an alternate Notch-1 ligand, as has been used in the OP9 stromal co-culture system[6], was also investigated. DL1 ligand in the same range of coating concentrations was incapable of generating DN2 or DN3 progenitor T cells and the cells retained a DN1 phenotype (FIG. 5b). Interestingly, the Notch ligand DL1 was found to be less efficient for T-cell induction than DL4 due to weaker Notch pathway activation (FIG. 5d). These results are corroborated by previously published results which have shown that DL4 is a higher-affinity ligand than DL1 for Notch-1 receptor interactions[14,15]. Furthermore, previous studies have shown that shape of the well can dictate B lymphoid lineage development due to increased homotypic progenitor B cell interactions[7]. While a trend towards increased CD19+ B cell development in the U-bottom well shape in the absence of DL4 was observed, the shape of the coated DL4 well did not mediate an effect on T cell development (FIG. 5c).

It has been previously shown that the soluble form of DL1 is inhibitory to Notch function in C2C12 myoblasts[8]. Therefore, the possible inhibitory effect of soluble DL4 on T cell development was investigated. Accordingly, the frequency of each DN subset, as well as myeloid and B lymphoid cells, was measured after 7 days of culture on adsorbed DL4, in soluble DL4 or in a mixture of adsorbed and soluble DL4. Not only was soluble DL4 ligand insufficient to support T cell development to the DN2 and DN3 subsets, but in fact the presence of soluble DL4 ligand completely inhibited the inductive effects of adsorbed DL4 ligand (FIG. 4c). When HSPCs were differentiated in 10 μg/mL soluble DL4 ligand, no DN3 cells were generated as compared to 10 μg/mL adsorbed DL4 ligand, and cells retained a DN1 phenotype (FIG. 4c). Thus, DL4 ligand needs to be immobilized to a surface in order to sustain Notch signaling for T cell development. When the effect of combining adsorbed and soluble DL4 ligand was assessed, the presence of soluble DL4 was found to completely hinder the inductive effect of the adsorbed DL4 on DN3 cell production. However, in the same total concentration of immobilized DL4 ligand (20 µg/mL), in the absence of soluble ligand, HSPCs generated DN3 cells at equivalent frequencies as in the 10 µg/mL coated DL4 control (FIG. 4c). This confirms that the inhibition of DN3 development observed in cultures containing both soluble and immobilized DL4 is due to the presence of soluble DL4 and not related to an increase in the DL4 concentration. To determine the mechanism for the inhibitory action of soluble DL4 on T cell differentiation, a surrogate NIH3T3 cell-line assay was engineered to quantify Notch pathway activation via intranuclear CBF1-luciferase expression. This assay revealed that the addition of soluble DL4 actively inhibits translocation of the intracellular domain of Notch1 receptor even when cells are on immobilized DL4 (FIG. 5e). From these results it was concluded that the absence of soluble unbound DL4 must be ensured in our engineered thymic niche as even trace levels may inhibit T cell production.

Figures 4D, 4E:
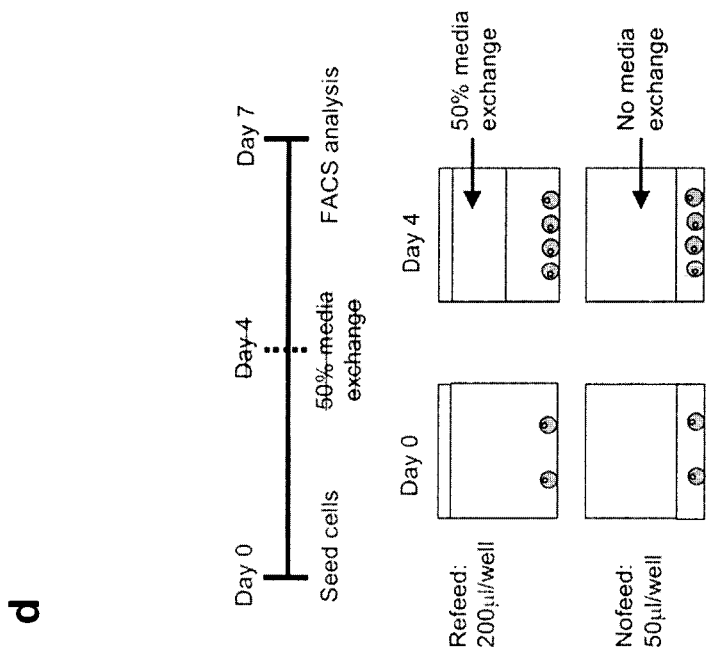
Figures 4F, 4G:
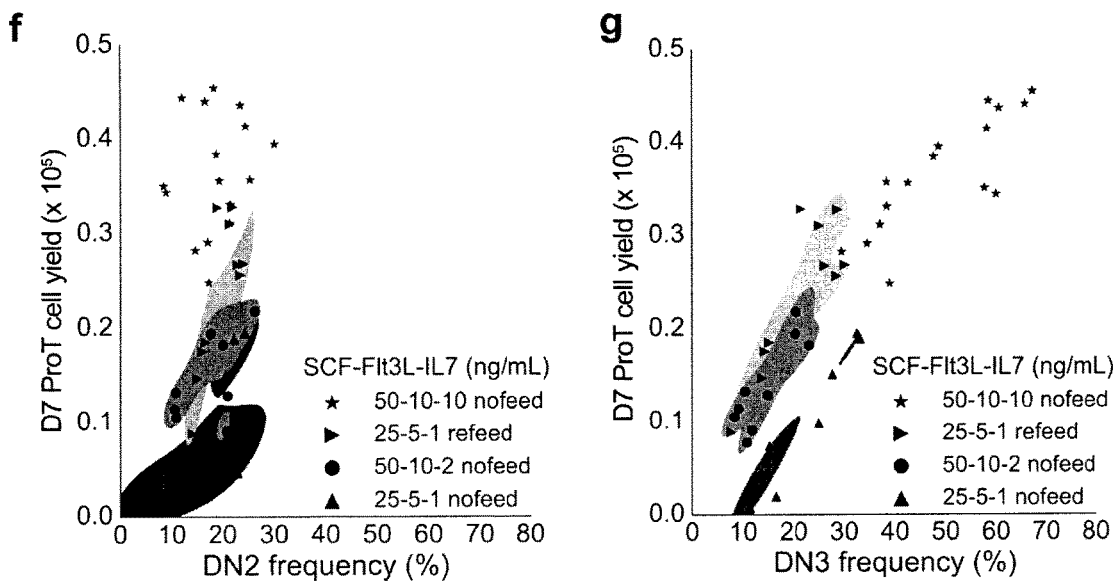
Figures 5A, 5B:
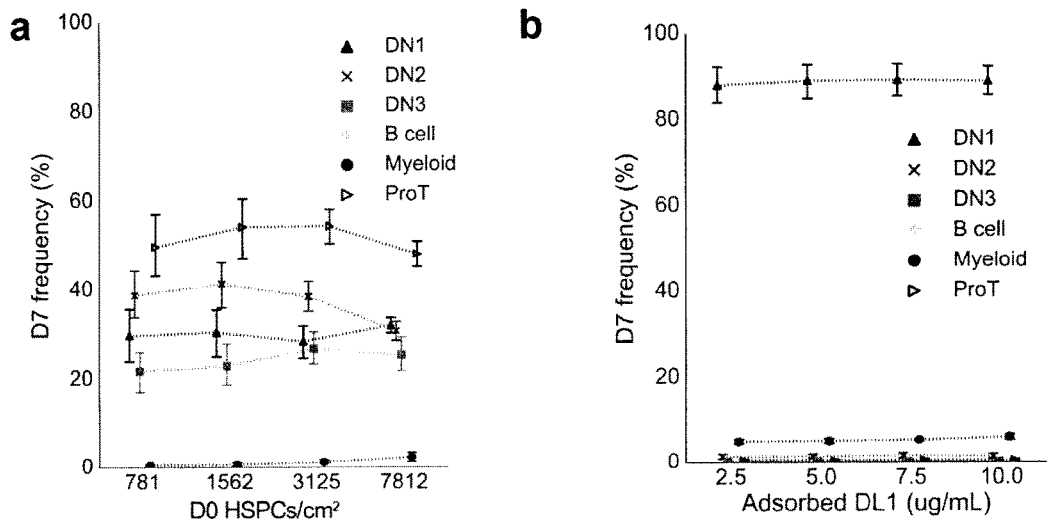
FIGS. 5a-g depict optimization of design parameters of HSPC seeding density, ligand choice and well shape.
Figures 5C, 5D, 5E:
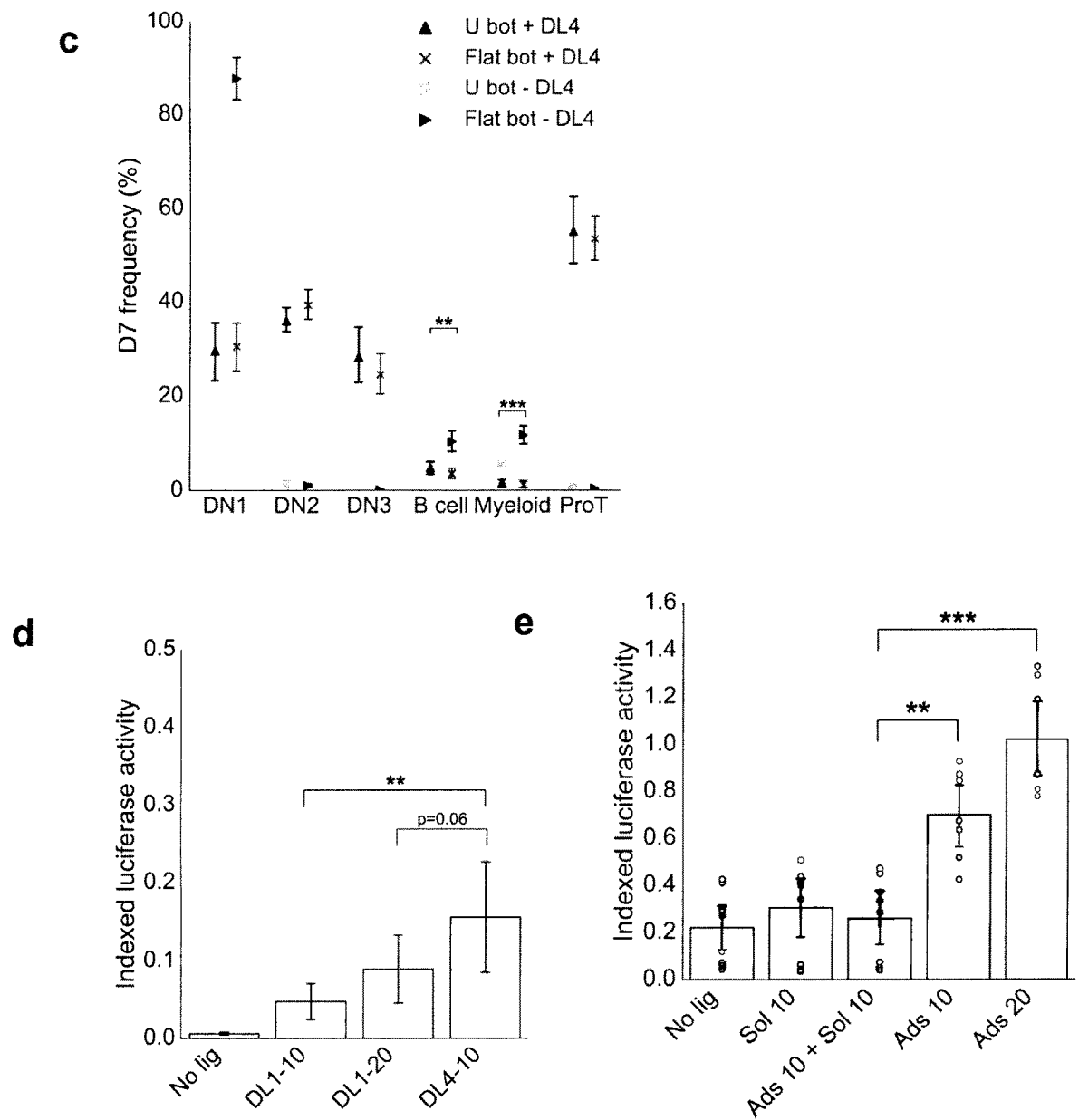
Figure 5F:
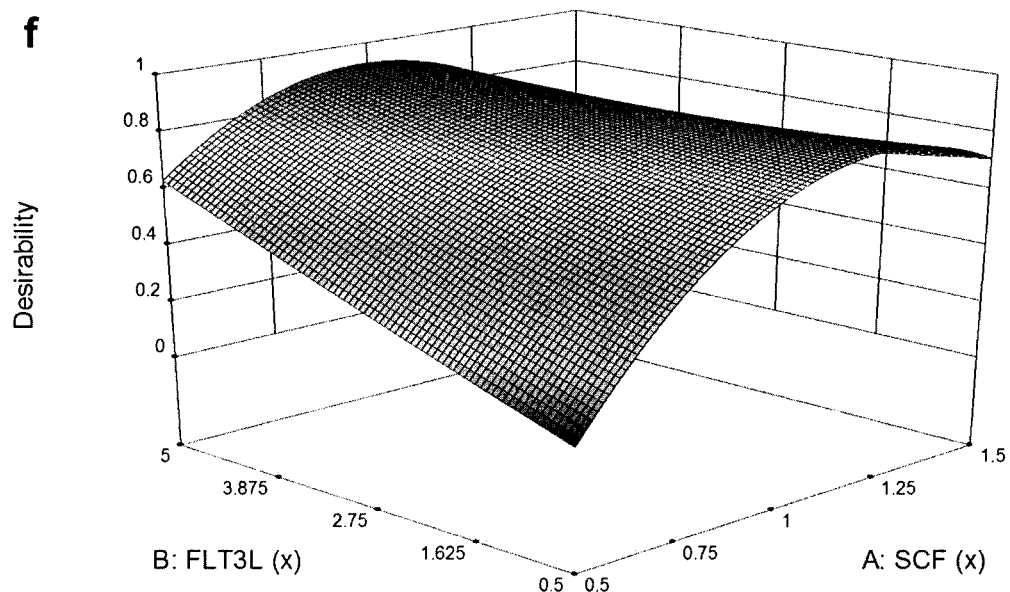
Figure 5G:
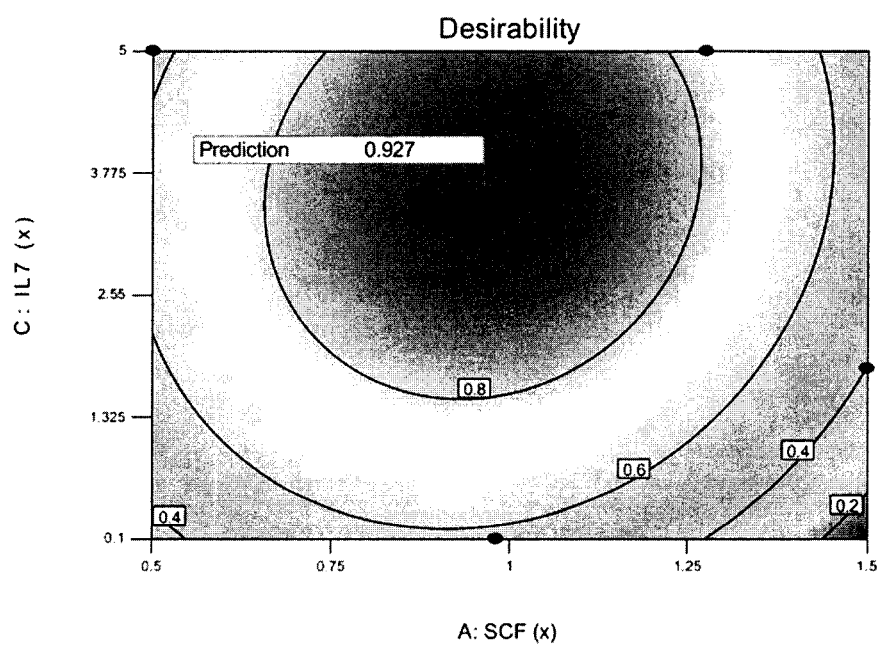

Next, the possibility of eliminating the day 4 medium exchange was studied in order to improve reproducibility by reducing user manipulation and medium costs while maintaining or enhancing progenitor T cell yield (FIG. 4d). Using a Design of Experiment (DOE) modeling approach (FIG. 4e), the ability to reduce medium consumption was examined by varying the concentrations of exogenous cytokines added to the system. The baseline control used 25 ng/mL SCF, 5 ng/mL Flt3L and 1 ng/mL IL-7 in 200 µL medium/well (25-5-1 re-feed condition; FIG. 4f-g) based on previously published OP9 stromal co-culture systems[9]. When the medium volume was reduced to the minimum amount possible (50 µL/96-well) while keeping the cytokine concentrations constant, the total cell fold expansion decreased by nearly a third compared to the baseline control (25-5-1 no-feed condition; FIG. 4f-g). However, when the cytokine concentrations were doubled to 50 ng/mL SCF, 10 ng/mL Flt3L and 2 ng/mL IL-7, cell proliferation capacity was regained, comparable to control, but the cells did not differentiate significantly to DN2 or DN3 T cells (50-10-2 no-feed condition; FIG. 4f-g). By simply increasing the IL-7 concentration from 2 to 10 ng/mL (50-10-10 no-feed condition; FIG. 4f-g), the cells produced significantly higher yields of T lineage-committed DN3 cells than the control. Using DOE enabled the optimization of the desirability index of producing DN3 cells at high frequency and yield by modeling and testing non-linear combinations of SCF, Flt3L and IL-7 (FIG. 5f, 5g). Thus, by adjusting the exogenous cytokine concentrations while decreasing medium consumption, the efficiency of T cell differentiation was increased while reducing the total amount of cytokines that need to be added to the system and the need for user manipulation during the course of the assay was eliminated.

Figures 6A, 6B:
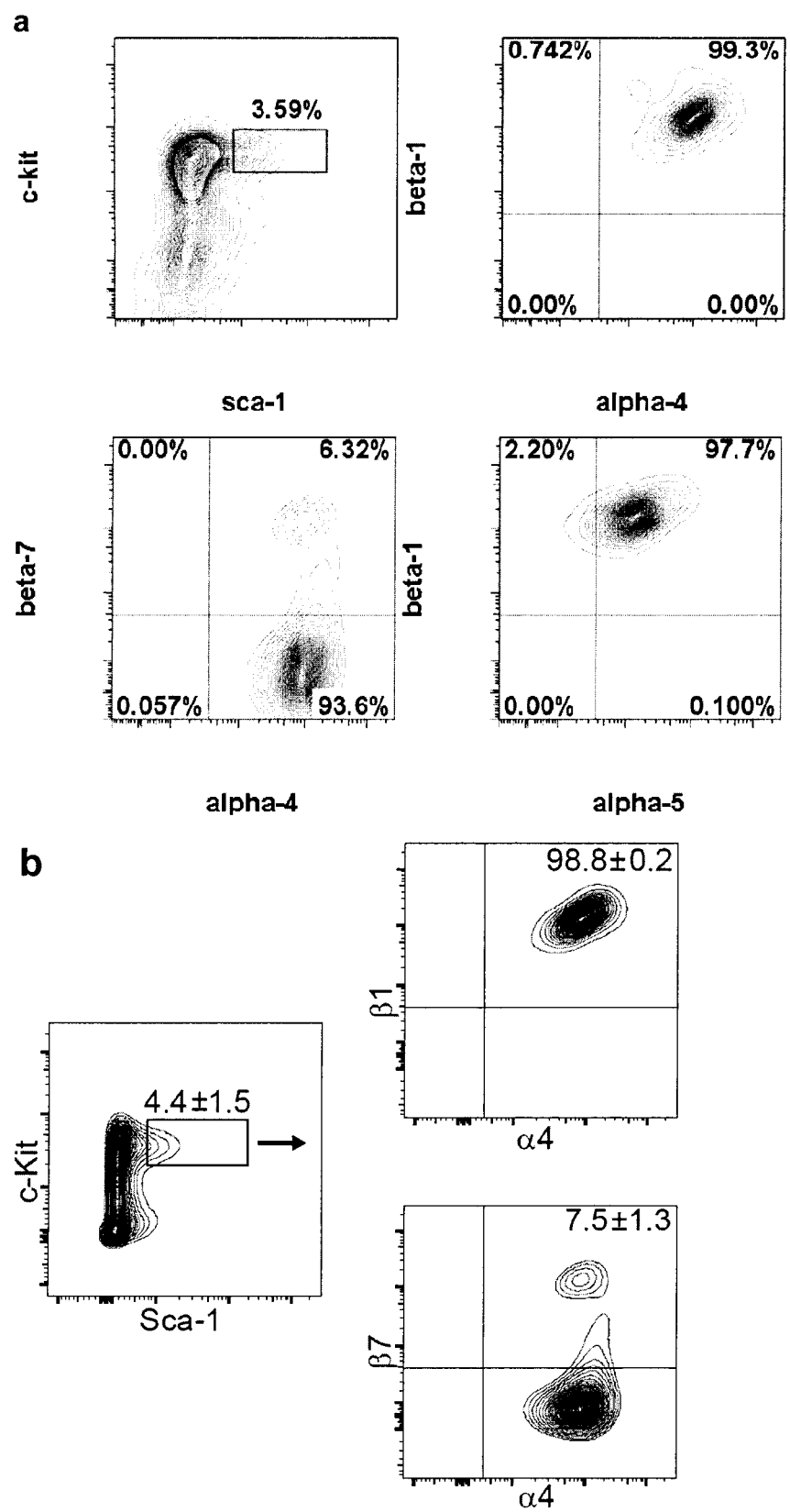
FIGS. 6a-n illustrate that the cellular matrix VCAM-1 enhances DN3 yield in engineered thymic niche.
FIG. 6b: Flow cytometry analysis of day 0 TER-119-depleted cells were first gated on Sca-1+ cKit+ cells (HSPC compartment) and subsequently the expression of $\alpha 4\beta 1$ and $\alpha 4\beta 7$ integrins was quantified (n=3).

Example 4: Cellular Matrix VCAM-1 Enhances DN3 Yield in the Defined T Cell Differentiation Assay As the next step in engineering our thymic niche, the incorporation of the extracellular matrix protein fibronectin or the thymic epithelial cell-presented matrix protein VCAM-1 was examined to determine whether DN3 yields in the defined T cell differentiation assay could be improved. Both proteins have been shown to play pleiotropic roles in progenitor T cell proliferation, survival, homing and specification[16,17]. As fibronectin and VCAM-1 are ligands for α4 and α5 integrins when paired with β1 or β7 integrins[17], the expression of these integrin receptors on the sorted sca1+ ckit+ HSPC compartment was first confirmed. Indeed, α4β1 and α5β1 were expressed at very high levels while α4β7 was expressed at low levels in HSPCs (FIG. 6a,b).

Figures 6C, 6D:
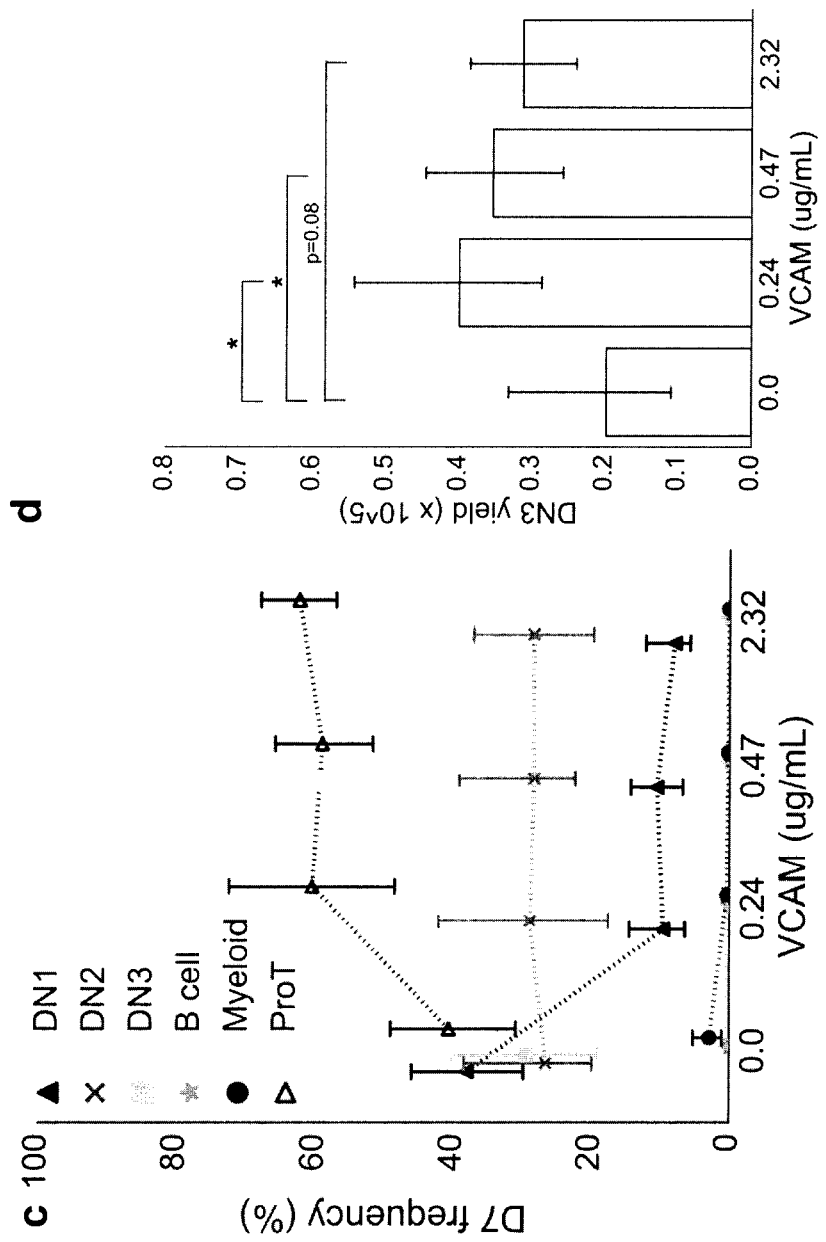
FIG. 6c: Graph depicting sorted Sca-1+cKit+ HSPCs that were cultured on 10 μg/mL DL4-Fc alone or 10 μg/mL DL4-Fc with increasing concentrations of VCAM-1 (0.24, 0.47 and 2.32 μg/mL); DN1, DN2, DN3, CD19+ B cell, CD11b+ myeloid and CD25+CD90+ proT cell frequencies were quantified on day 7 (n=3).
FIG. 6d: Graph depicting quantification on day 7 of total DN3 progenitor T cell yield on 10 μg/mL DL4-Fc alone or 10 μg/mL DL4-Fc with increasing concentrations of VCAM-1 (0.24, 0.47 and 2.32 μg/mL); data represent mean±95% Cl for n=3 biological replicates. *P<0.05; P<0.01; *P<0.001.
Figure 6E:
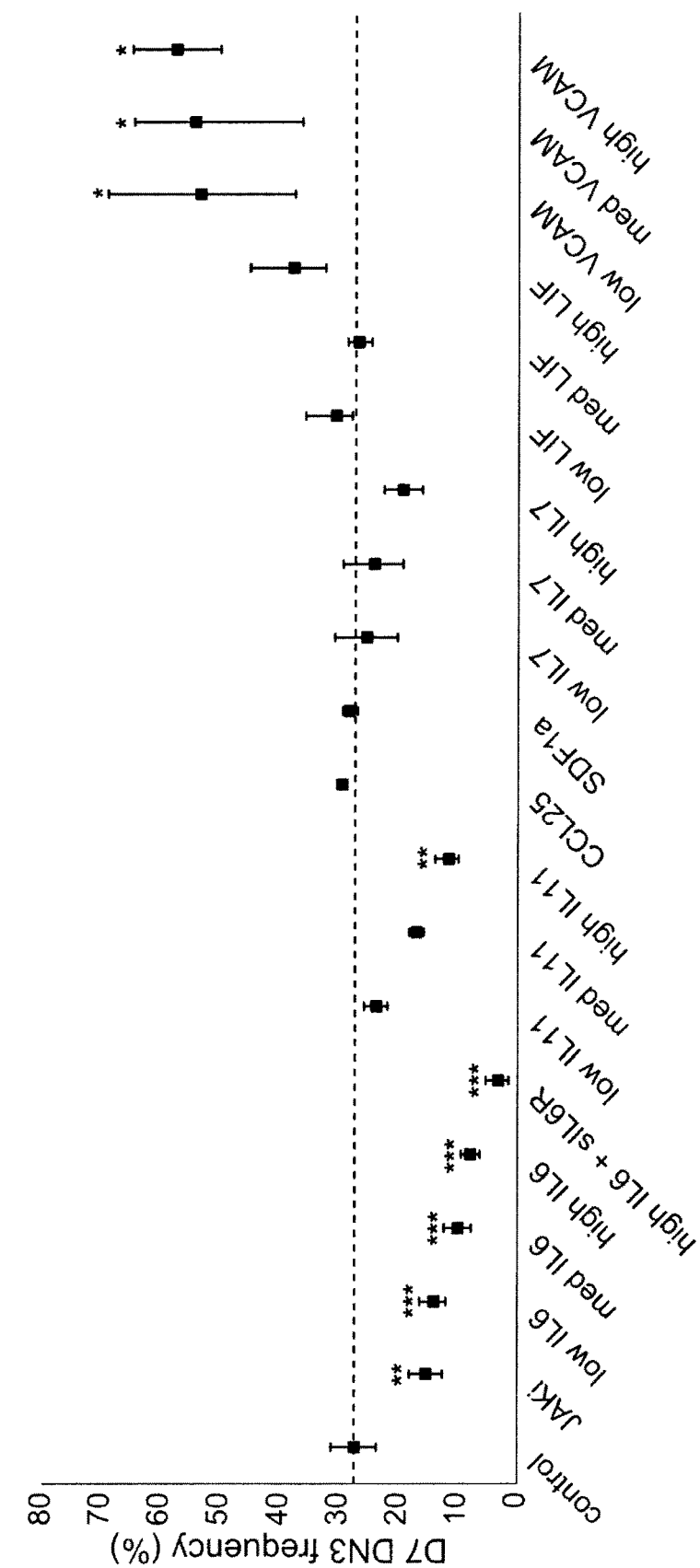
FIG. 6e: Graph depicting a screening study that was performed to assess the effect of different concentrations of several cytokines (IL-6, soluble IL-6R (sIL6R), IL-11, IL-7, leukemia inhibitory factor (LIF)), chemokines (CCL25, SDF1α) and matrix protein (VCAM-1) on T-lineage committed DN3 cell frequency on day 7 of culture (n=3); data represent mean±95% Cl for n=3 biological replicates. *P<0.05; P<0.01; *P<0.001.

Next, the effect of increasing immobilized concentrations of VCAM-1 was studied in the defined T cell differentiation assay. VCAM-1 significantly decreased the DN1 frequency while increasing CD25+CD90+ frequency in a dose-dependent manner (FIG. 6c-d). Specifically, increasing doses of VCAM-1 enhanced the frequency of DN3 cells while DN2, myeloid and B cell compartments remained unchanged (FIG. 6c). As inclusion of VCAM-1 did not affect the total yield of CD45+7AAD− cells (FIG. 7), VCAM-1 enhanced the purity and overall yield of DN3 cells in the defined T cell differentiation assay. In a screen of candidate cytokines, chemokines, and matrix proteins known to be important for thymocyte development in vivo[18,19,20,21], VCAM-1 had the most significant effect on enhancing T lineage committed DN3 cells (FIG. 6e).

Figures 6F, 6G:
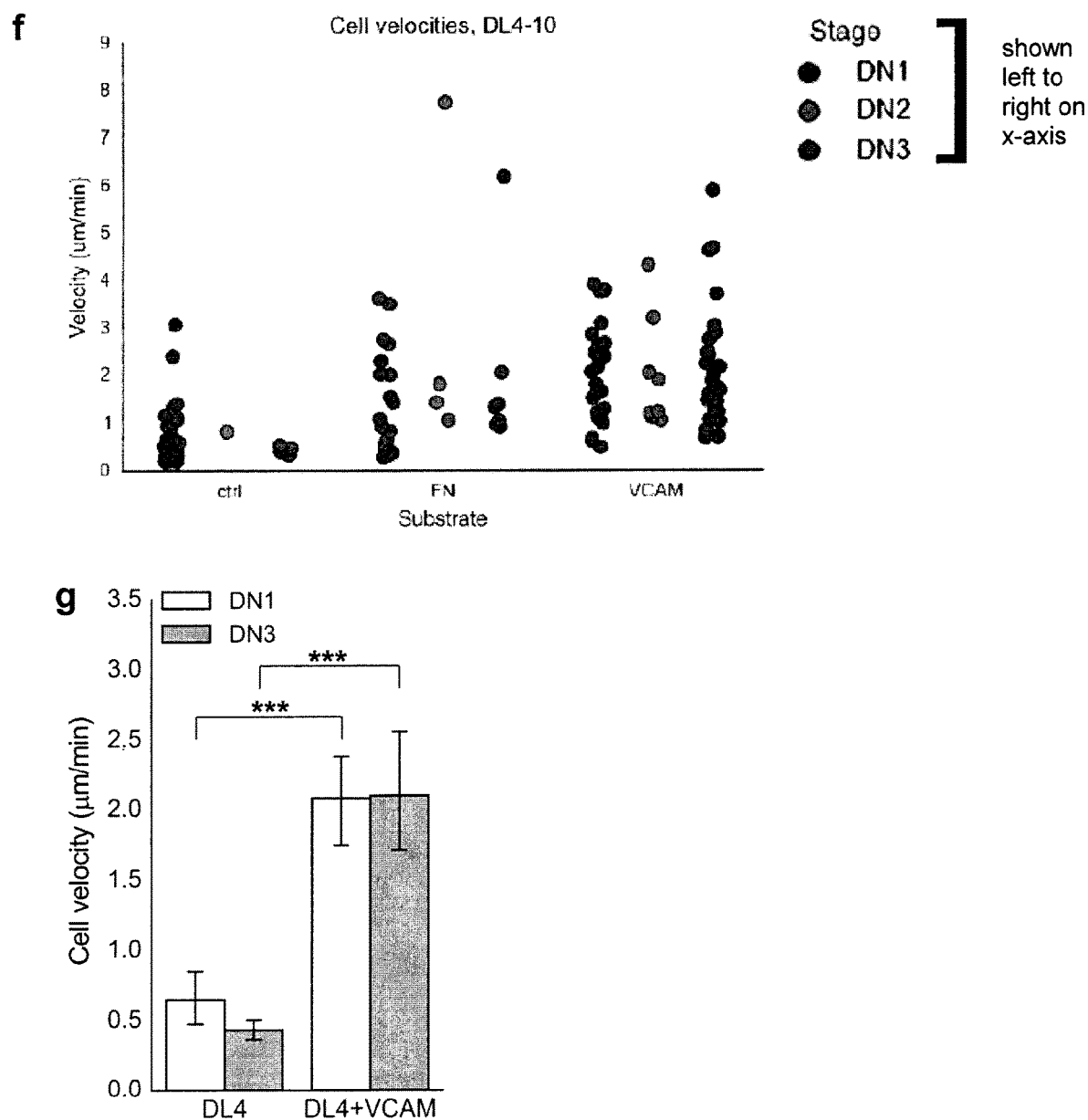
FIG. 6f: Graph depicting quantification of cell velocity (μm/min) of DN1, DN2 and DN3 cells on 10 μg/mL DL4-Fc alone, or DL4+fibronectin and DL4+VCAM-1 from days 5-7 of culture.
FIG. 6g: Graph depicting quantification of averaged cell velocity (μm/min) of DN1 and DN3 cells on 10 μg/mL DL4-Fc alone or DL4+VCAM-1 from days 6 to 7 of culture (n=3).
Figures 6H, 6I, 6J, 6K:
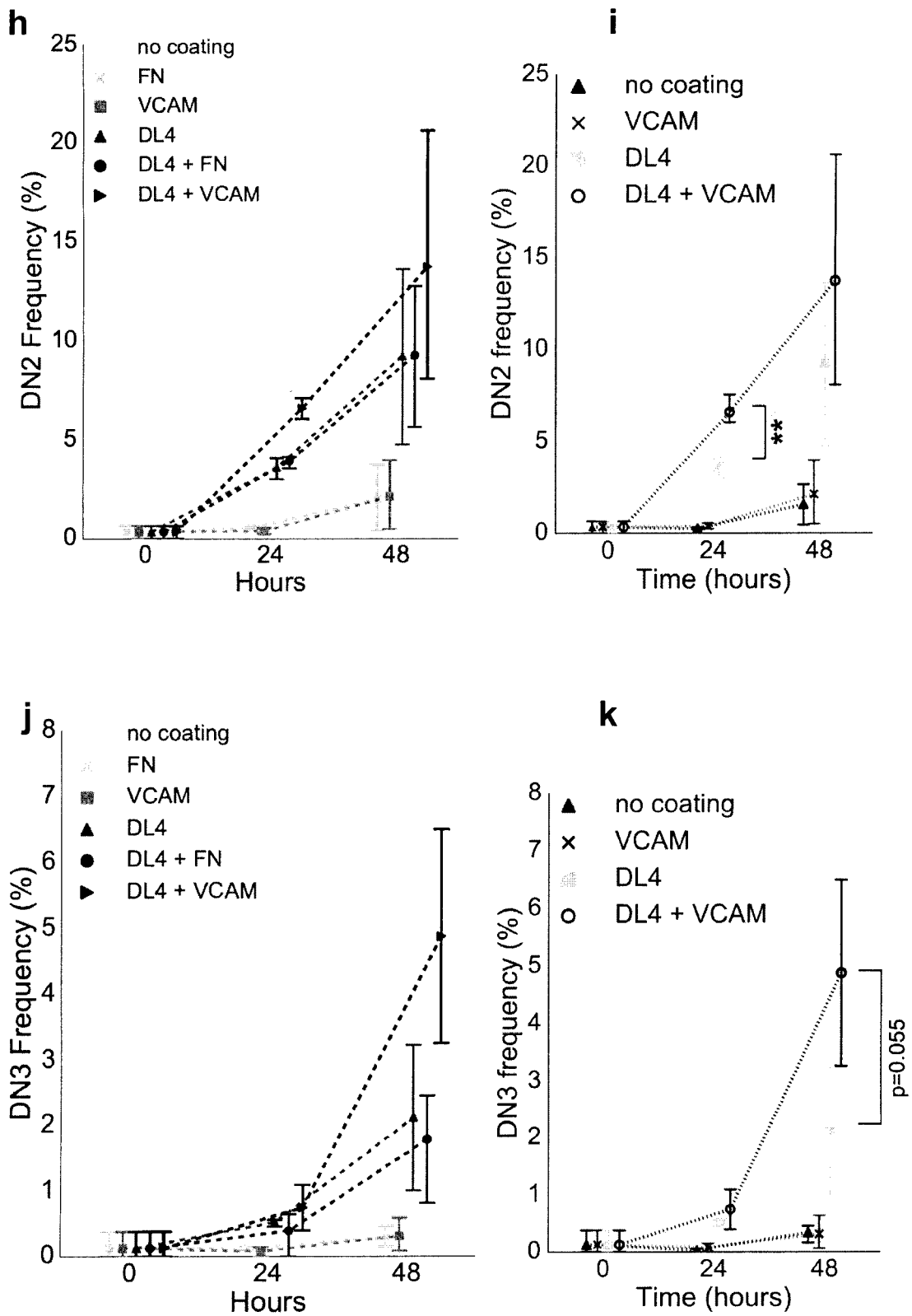
FIG. 6h: Graph depicting assessment of frequency of DN2 (CD25+CD44+) generation at 24 and 48 hours after initiation of culture of sorted HSPCs on no coating, fibronectin (FN), VCAM-1, DL4, DL4+FN and DL4+VCAM-1; DL4+VCAM-1 shows the quickest generation of DN2 cells as compared to all other coating conditions.
FIG. 6i: Graph depicting sorted Sca-1+cKit+ HSPCs that were seeded on no coating, 2.32 μg/mL VCAM-1, 10 μg/mL DL4, or DL4+VCAM-1; DN2 frequencies were quantified at 0, 24 and 48 hours of culture (n=4).
FIG. 6j: Graph depicting assessment of frequency of DN3 (CD25+CD44−) generation at 24 and 48 hours after initiation of culture of sorted HSPCs on no coating, FN, VCAM-1, DL4, DL4+FN and DL4+VCAM-1. DL4+VCAM-1 shows the quickest generation of DN3 cells as compared to all other coating conditions.
FIG. 6k: Graph depicting sorted Sca-1+cKit+ HSPCs that were seeded on no coating, 2.32 μg/mL VCAM-1, 10 μg/mL DL4, or DL4+VCAM-1. DN3 frequencies were quantified at 0, 24 and 48 hours of culture (n=4).
Figure 6L:
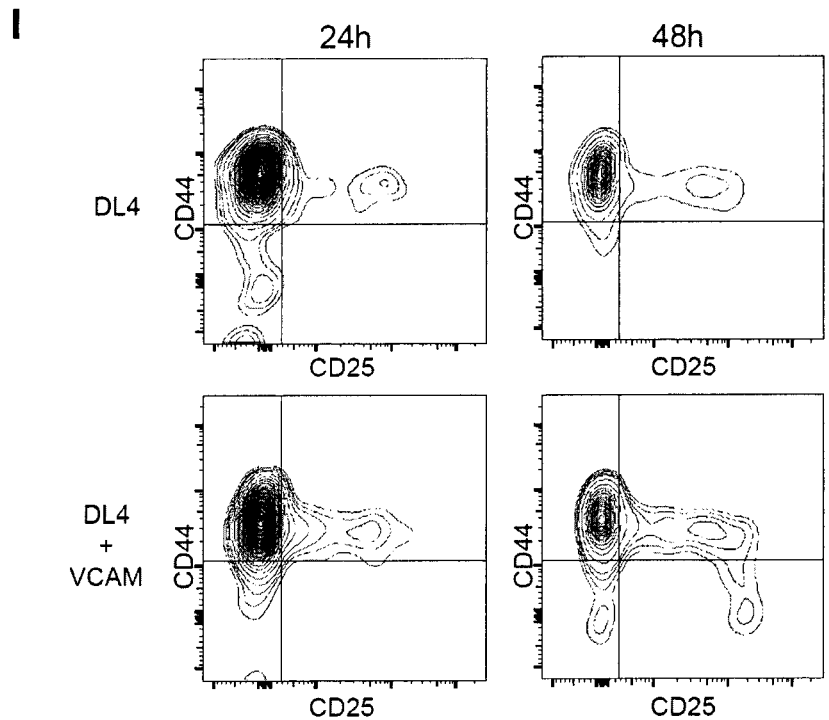
FIG. 6*l*: Representative flow plots of HSPCs 24 and 48 hours after culture on DL4 vs. DL4+VCAM-1 (n=4).
Figure 6M:
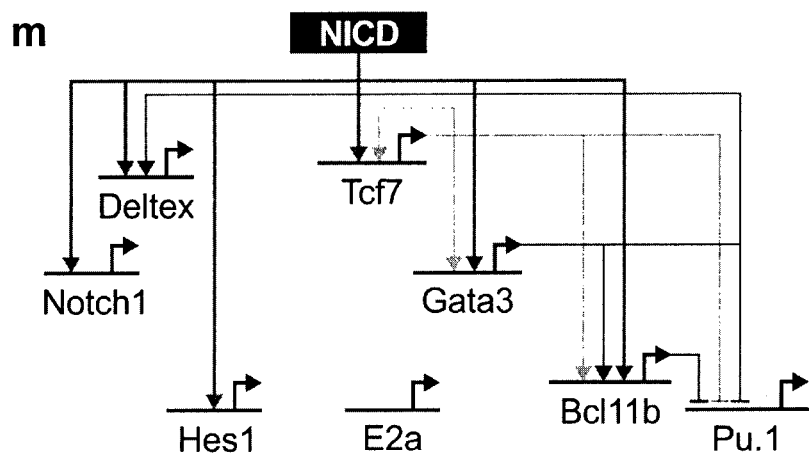
FIG. 6*m*: Illustration of Notch1 receptor intracellular domain (NICD) translocation to the nucleus and activation of the T-cell development gene network comprising several feedback network motifs.
Figure 6N:
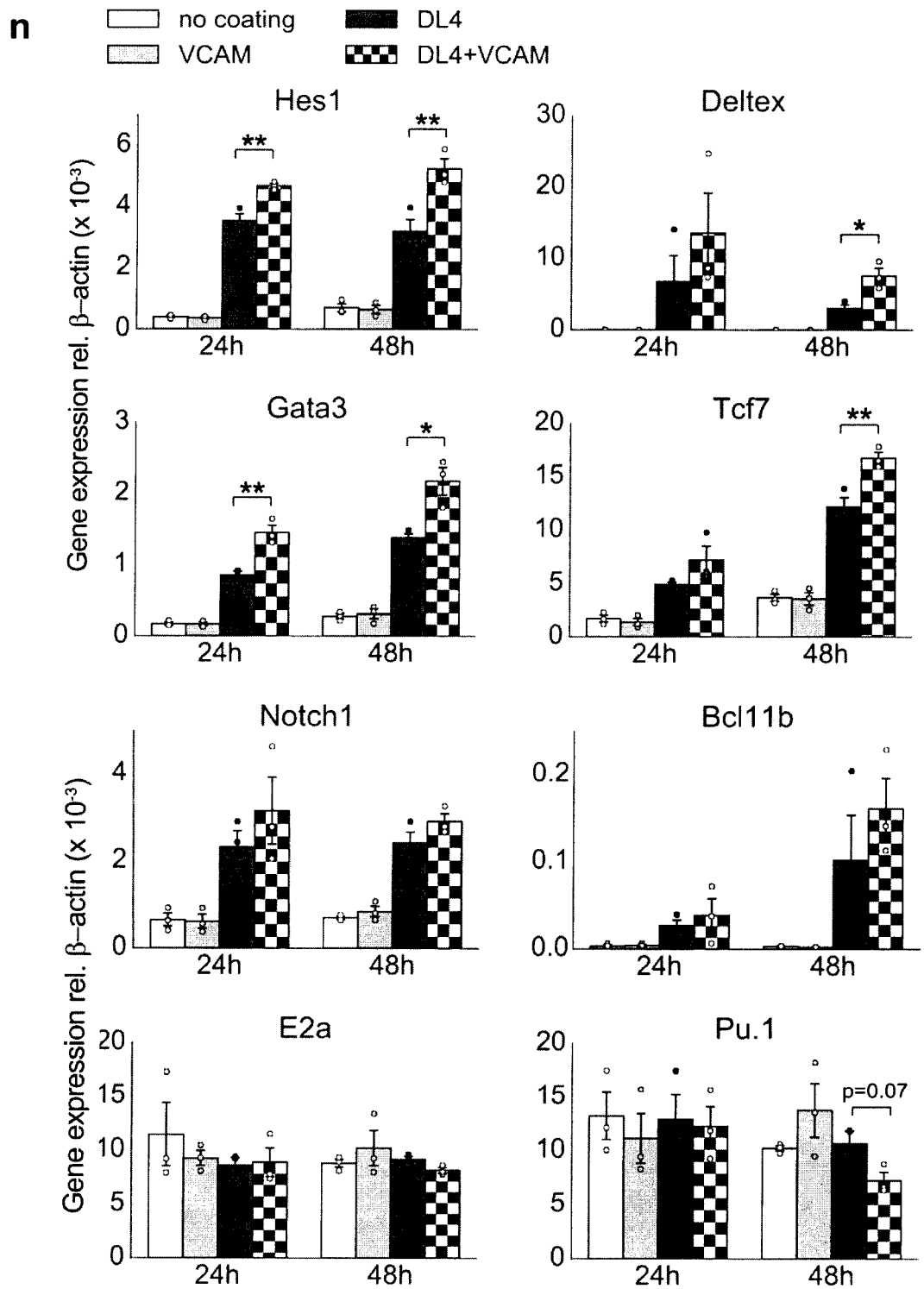

Next, the effect of VCAM-1 on the motility of DN T cells using live cell imaging was investigated, as it has been implicated as a stromal matrix for thymic migration in vivo[22]. The random migration patterns of single cells from day 5 to day 7 were manually tracked in the defined T cell differentiation assay and DN1, DN2 and DN3 phenotypes were discriminated using surface marker staining for CD25 and CD44 (data not shown). VCAM-1 was found to significantly increase the velocity of all three DN1-3 subtypes compared to the velocity of these subtypes cultured on DL4 alone (FIG. 6f, 6g). To investigate the mechanism of how VCAM-1 enhances DN3 production, surface marker expression and key Notch pathway genes that are upregulated in sorted HSPCs at 24 and 48 hours after interaction with DL4 and VCAM-1 were examined. Accelerated production of DN2 cells at 24 hours and DN3 cells at 48 hours was found on DL4 and VCAM-1 compared to any other coating conditions (FIG. 6h-6l). Key nodes in the T-cell development gene regulatory network were examined in sorted HSPCs within the first 48 hours of interaction with DL4 and VCAM-1 (FIG. 6m). A significant increase in downstream Notch pathway genes such as Hes1, Gata3, Tcf7 and Deltex was also found in the presence of DL4 and VCAM-1 compared to DL4 alone (FIG. 6n). Additionally, the myeloid gene PU.1 was downregulated more rapidly at 48 hours in the presence of DL4 and VCAM-1 than in DL4 alone (FIG. 6n). Lastly the Notch1 receptor gene expression and stem cell factor E2a remained unchanged in all coating conditions (FIG. 6n). Thus, VCAM-1 synergistically interacts with DL4 to increase DN3 T cell yield in the assay by enhancing Notch pathway gene activation and cell motility. Access to Notch ligand is thereby increased, enabling stronger activation of downstream Notch pathway genes that rapidly activate the T-cell development GRN and repress alternate lineage pathways.

Figures 8C, 8D, 8E:
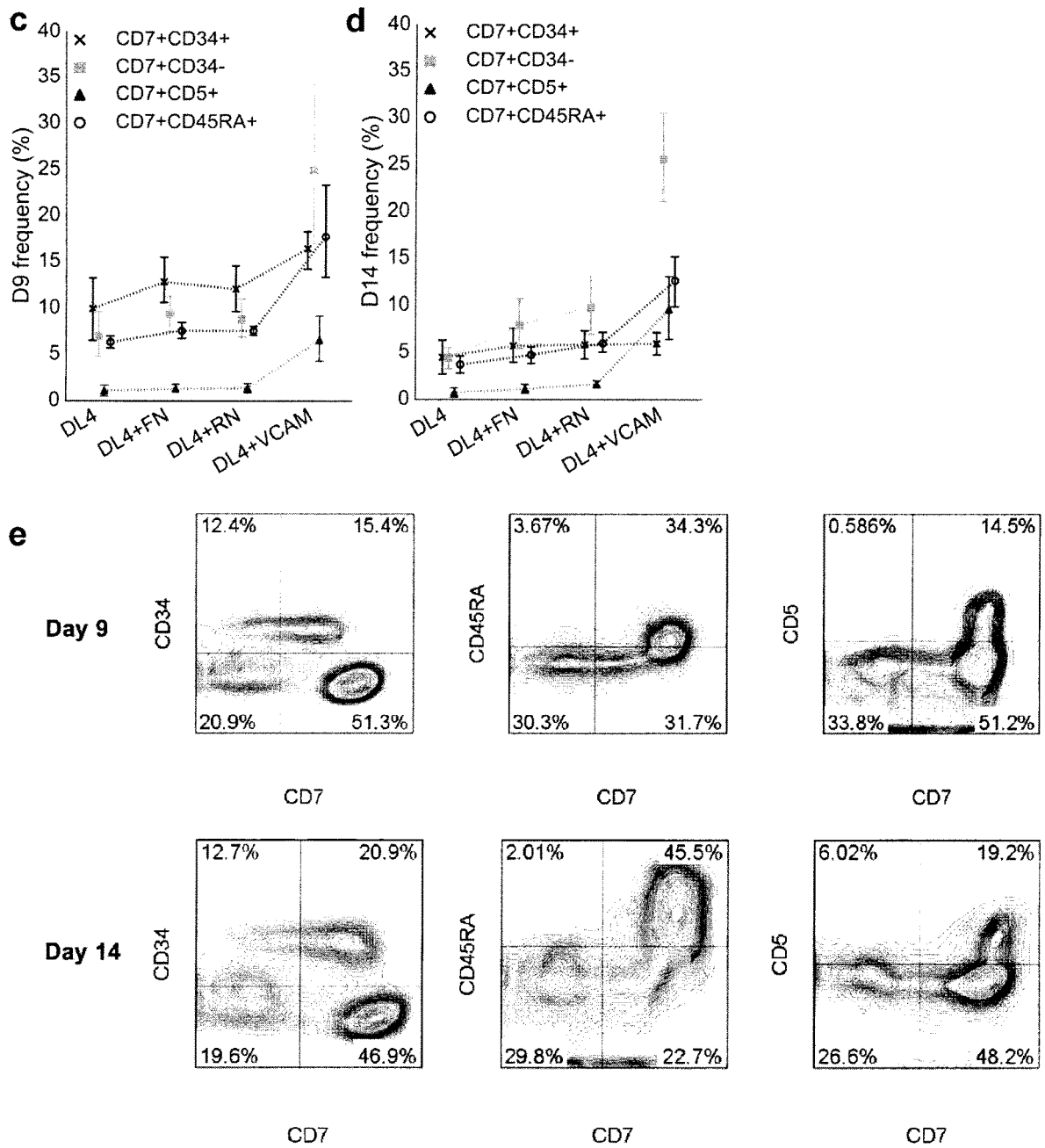
Figure 8F:
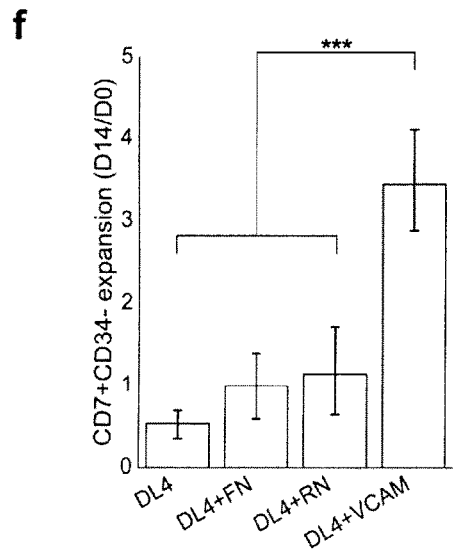
Figure 8G:
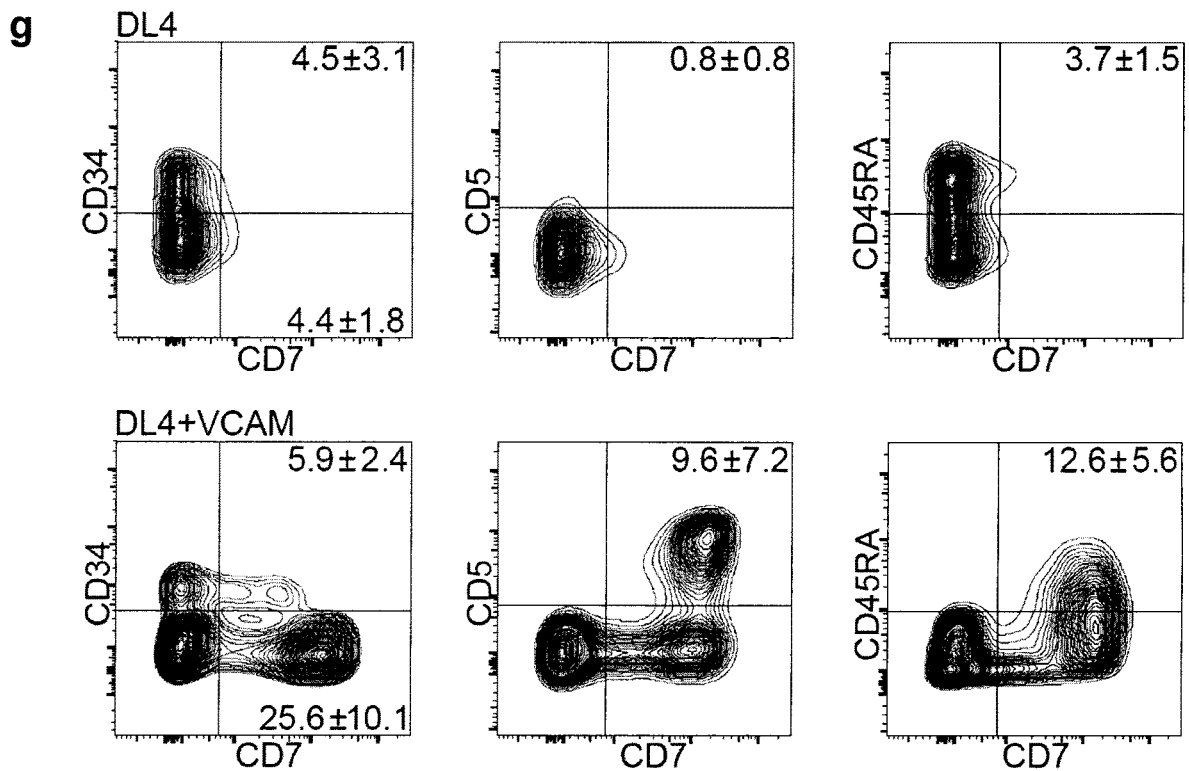

Example 5: Human CD34+ HSPCs can Generate Progenitor T Cells in the Engineered Thymic Niche The development of a defined T cell differentiation assay described to this point represents an engineered "thymic niche" that has been optimized to differentiate mouse HSPCs to DN3 committed T cells. The translation of the engineered thymic niche to the human system was confirmed by differentiating human umbilical cord blood-derived CD34+ HSPCs to progenitor T cells. The desired human equivalent of T lineage-committed murine DN3 T cells is CD7+CD5+CD45RA+co-expressing progenitor T cells that have been shown to engraft thymi of immunodeficient mice more rapidly than CD34+ HSPCs[1]. To date, only stromal co-culture systems or serum-based undefined medium have been used to produce progenitor T cells from CD34+ cells[23,24]. Prior to initiation of each culture, we verified the purity of the input HSPCs to be greater than 95% CD34+(FIG. 8a). α4β1 was expressed at very high levels (96.9±1.1%) while α4β7 was expressed at low levels (5.5±1.0%) in CD34+ HSPCs (FIG. 8b). While DL4 alone can generate CD7+CD34+ cells in serum-free IMDM+BIT medium that are reminiscent of the earliest intrathymic progenitor phenotype, it was found that DL4 on its own is insufficient to drive these progenitor cells to later stages of T cell development (FIG. 8c,d). Consequently, the incorporation of extracellular matrix proteins retronectin, fibronectin and VCAM-1 in combination with DL4 was tested to determine whether these proteins could induce progenitor T cells. Retronectin or fibronectin in conjunction with DL4 were found to be incapable of differentiating CD7+CD34+ progenitors further along the T cell lineage (FIG. 8d). In fact, similar to the observations in the mouse system, only DL4+VCAM-1 was able to generate later stage CD7+ progenitor T cell populations that lost expression of CD34 and co-expressed CD5 and CD45RA (FIG. 8d). Progenitor CD7+ T cells began upregulating expression of CD45RA+ and CD5+ as early as day 9 of the cultures and expression levels increase up to day 14 (FIG. 8d). Furthermore, DL4+VCAM-1 enabled increased expansion of CD7+CD34− maturing human progenitor T-cells compared to DL4 alone or DL4 with fibronectin or retronectin (FIG. 8f). Flow cytometry revealed that the later stages of T-cell development in the defined assay were more pronounced in the presence of DL4+VCAM-1 than DL4 alone (FIG. 8g).

Figure 8H:
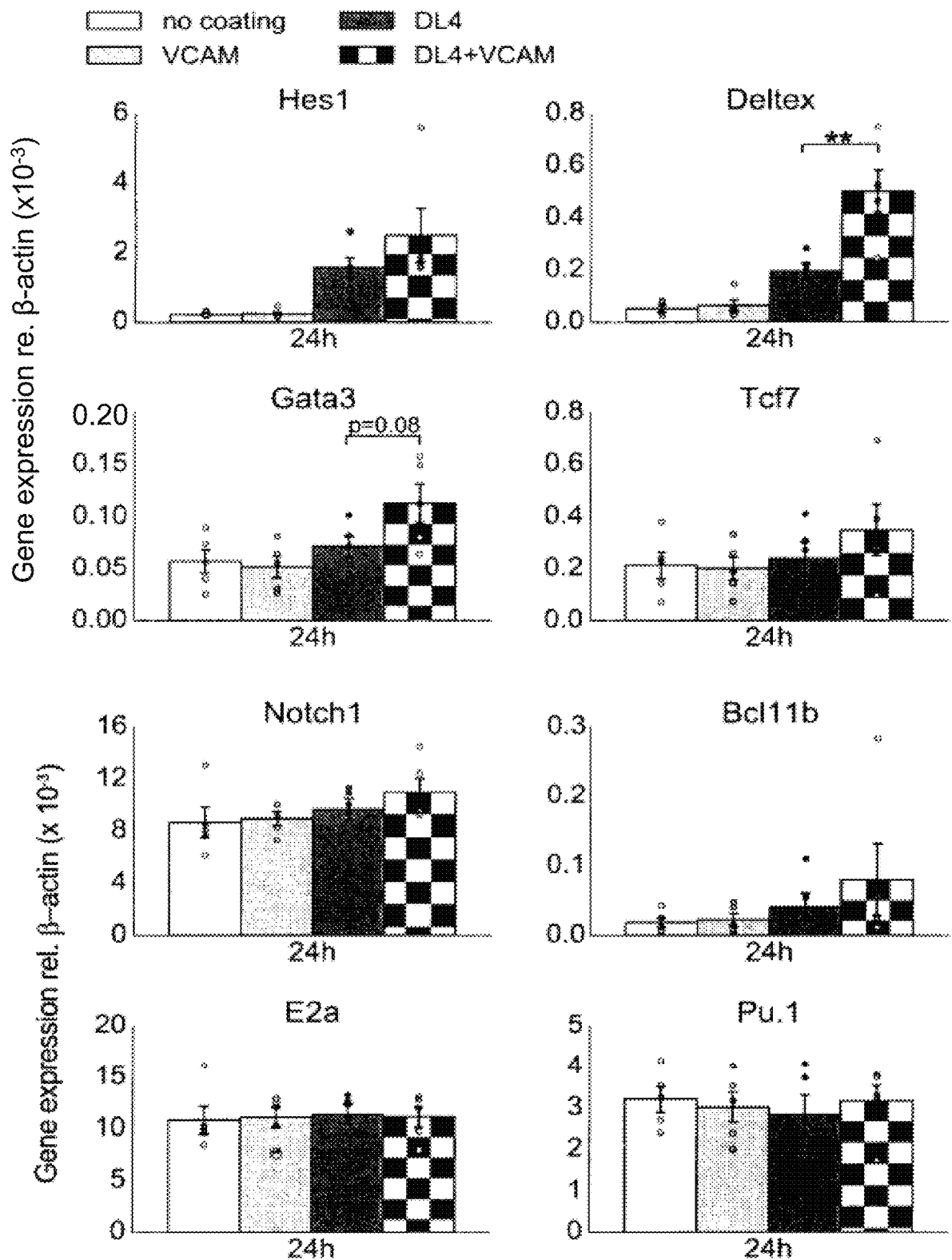

DL4 and VCAM-1 synergistically enhanced Notch target gene expression compared to DL4 alone (FIG. 8i-8j). The upregulation dynamics observed in human cells were different from those observed in mouse cells. Deltex and Gata3 were rapidly upregulated within 24 hours and showed sustained increases up to 96 hours. In contrast, Bcl11b required 96 hours of stimulation before significant enhancement relative to DL4 alone were observed (FIG. 8h).

Figures 9A, 9B, 9C:
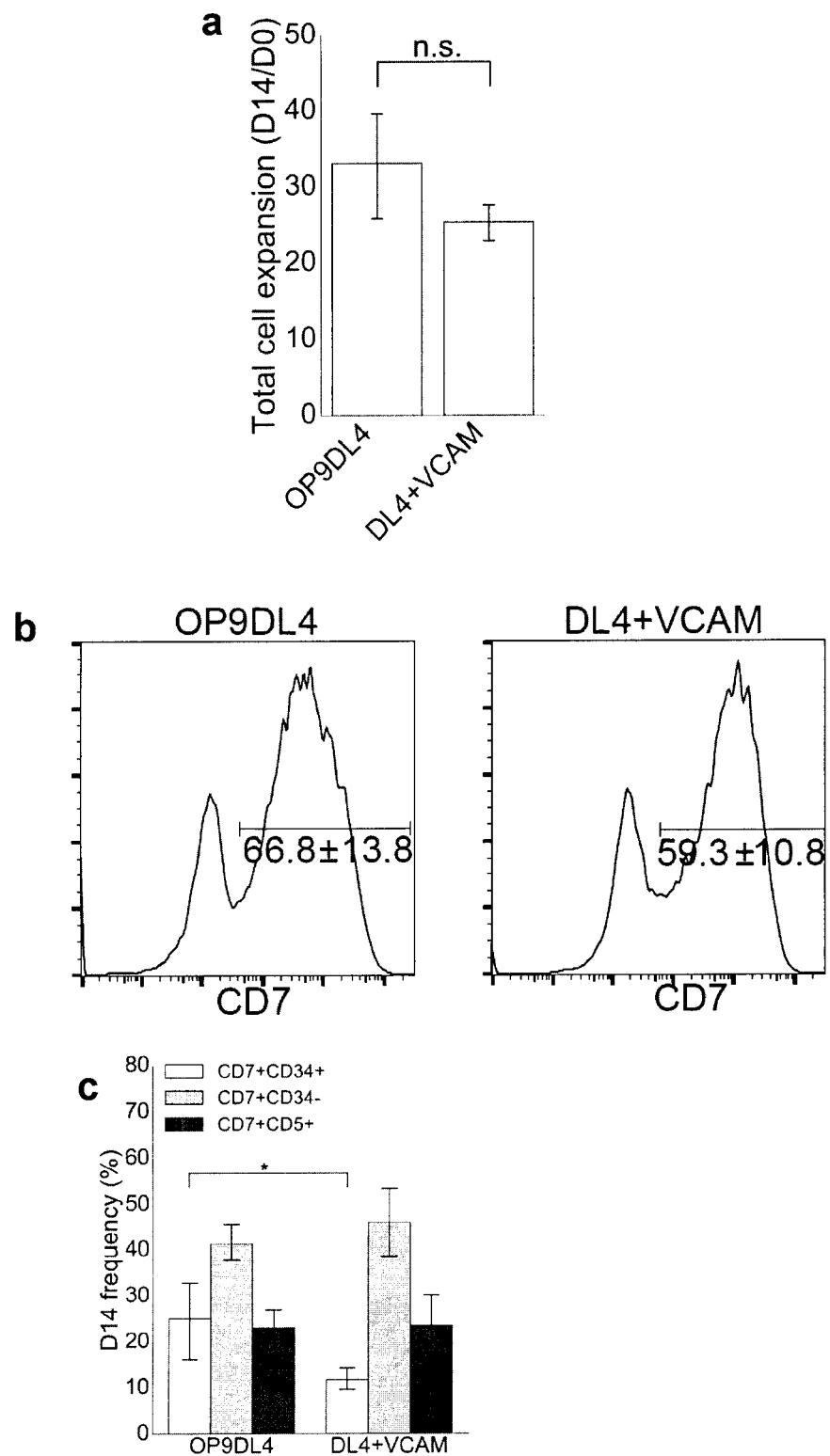
FIGS. 9*a-c* depict generation of human progenitor T cells on the engineered thymic niche and control OP9DL4 system.
Figures 10A, 10B, 10C, 10D:
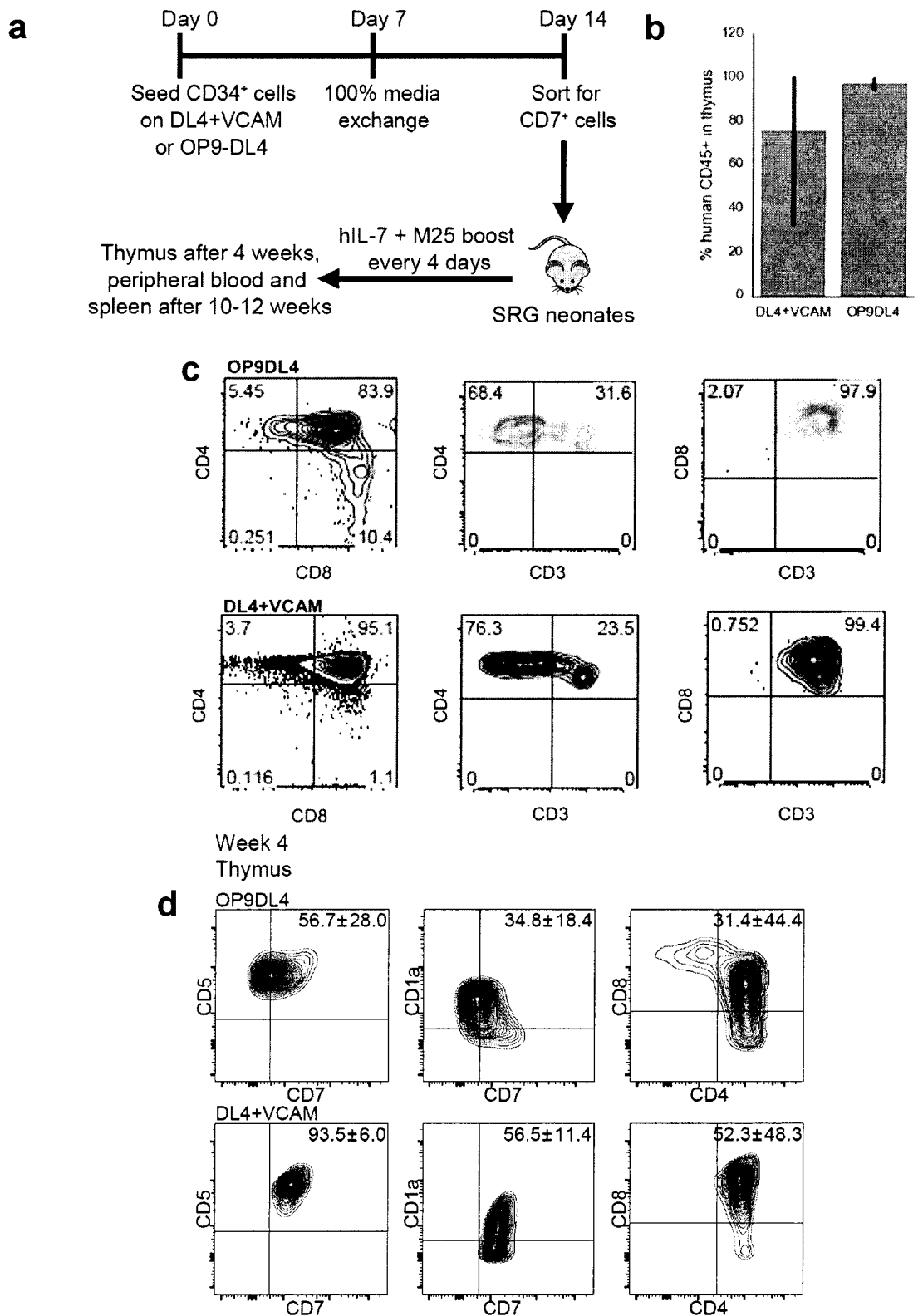
FIGS. 10*a-g* depict in vivo maturation of human progenitor T cells generated on the engineered thymic niche.
Figures 10E, 10F:
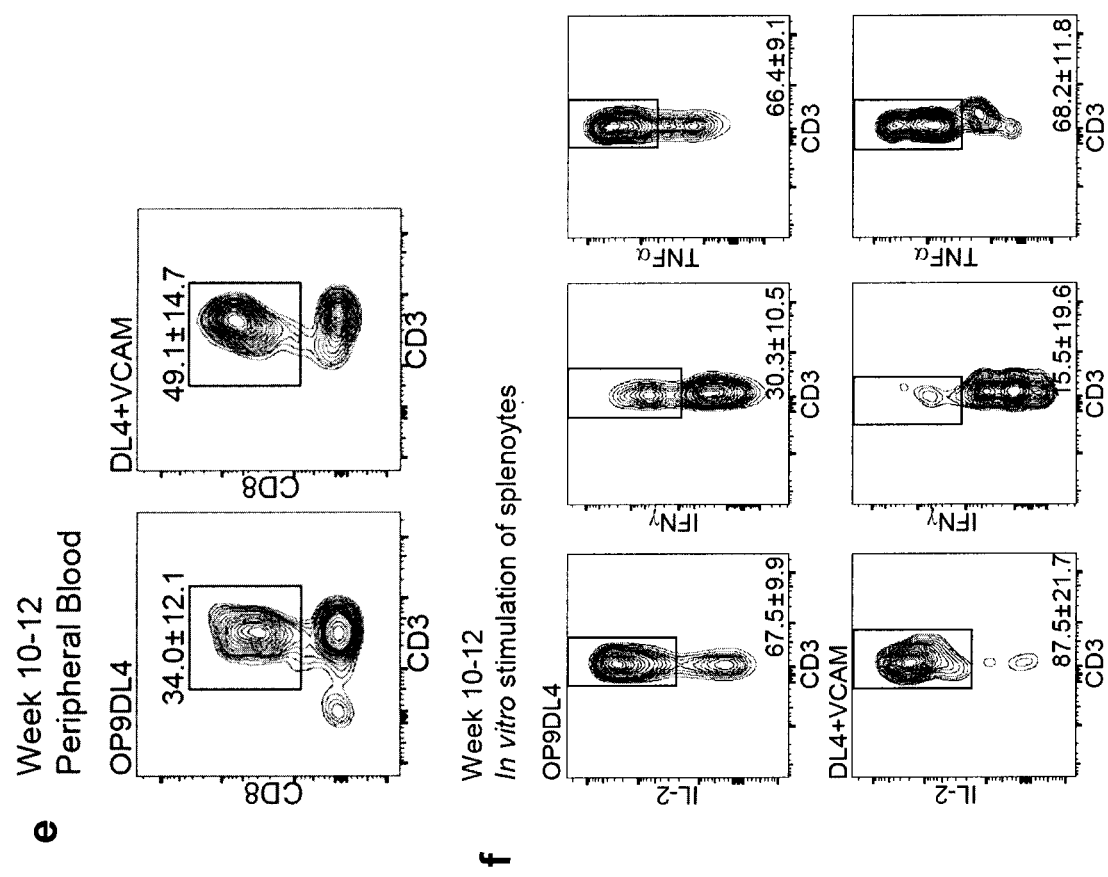
Figure 10G:
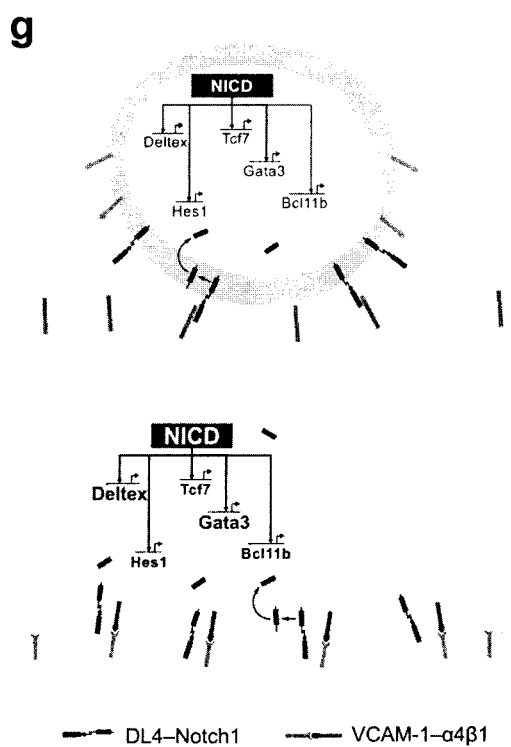

Next, a comparison of our engineered thymic niche with the gold standard OP9DL4 stromal co-culture assay was performed. OP9DL4 was found to enable similar total live cell expansion to the engineered thymic niche (FIG. 9a). Both systems gave rise to comparable CD7+ progenitor T cell populations that co-expressed CD5 (FIG. 9b-9c). However, differences were observed in the CD7+CD34+ primitive progenitor T compartment frequencies between the two systems (FIG. 9b, 9c). CD7+ progenitor T cells were sorted from both systems on day 14 of culture and injected intrahepatically into SRG neonatal mice to assess for in vivo engraftment potential (FIG. 10a). After four weeks, the thymi from these mice were harvested and high levels of engraftment of human CD45+ cells were found (FIG. 10b). Both systems generated similarly high DP T cell frequencies that co-expressed CD3 (FIG. 10c, 10d). After 10-12 weeks post-engraftment, mature circulating CD3+CD8+ T cells were detected in the peripheral blood indicating that DL4+VCAM-1-derived progenitor T-cells were capable of reconstituting the periphery of immunodeficient SRG mice (FIG. 10e). To confirm functional maturation, CD3+ T cells harvested from immunodeficient SRG mice after 10-12 weeks in vivo were stimulated with PMA and ionomycin in vitro. High levels of human IL-2, IFN-γ and TNF-α immunomodulatory cytokine secretion was observed (FIG. 10f). Hence, it was concluded that human CD7+ progenitor T cells produced in the engineered thymic niche are functional and capable of homing and engrafting thymi in vivo. Without being bound by theory, we predict that DL4 activates Notch-1 receptor on HSPCs which leads to translocation of NICD to the nucleus where it activates the Notch gene regulatory network (top; FIG. 10g). When DL4 is co-presented with VCAM-1 (bottom; FIG. 10g), α4 integrin receptors expressed on HSPCs engage with VCAM-1, which leads to higher activation of downstream Notch target genes, increased motility, and accelerated commitment to the T-cell fate.

Figure 11A:
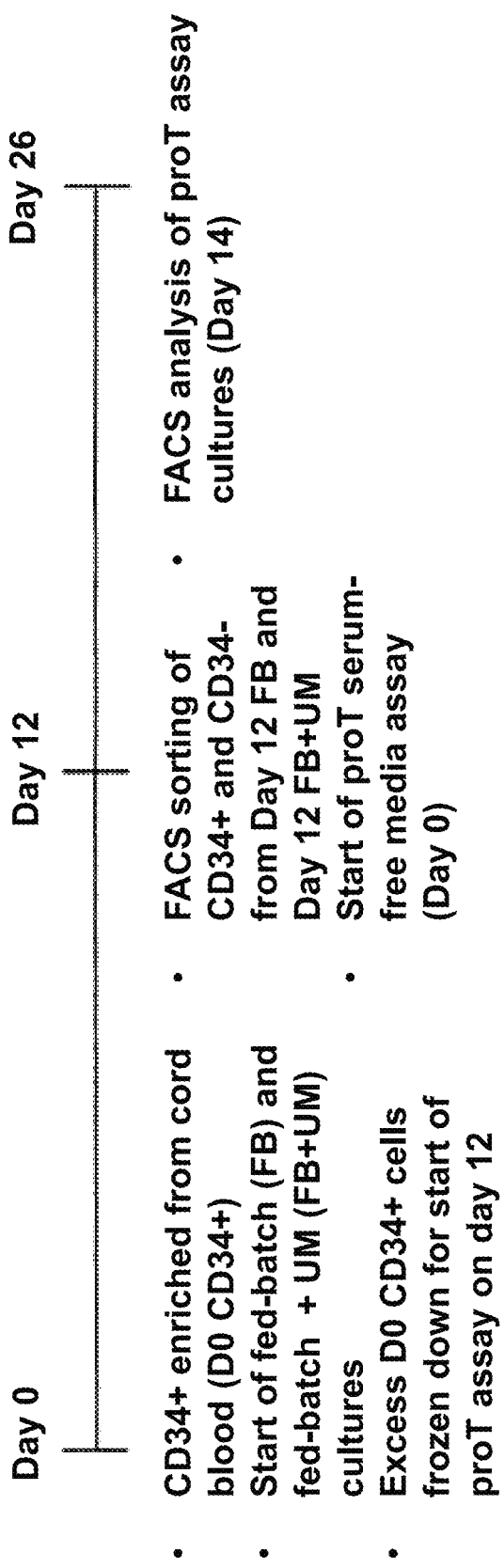
FIGS. 11*a-o* depict generation of progenitor T cells from fed-batch expanded CD34+ cord blood cells.

Example 6: Cultured CD34+ Cells can Generate Progenitor T Cells in the Engineered Thymic Niche Once it was established that human umbilical cord blood-derived CD34+ cells (or day 0 CD34+ cells) could generate functional progenitor T cells in the engineered thymic niche, the culture of CD34+ cells was tested to determine if these cells had T lymphoid potential that was equivalent to their day 0 CD34+ cell counterparts. Growing CD34+ cells in fed-batch bioreactor is one way of culturing CD34+ cells. Specifically, it has been previously demonstrated that fed-batch bioreactor technology can be used to yield a rapid (12-day) 11-fold increase of CD34+ HSPCs with self-renewing, multi-lineage repopulating ability. The generation of progenitor T cells from sorted day 12 CD34+ cells derived from fed-batch (FB) or fed-batch with UM-729 small molecule supplementation (FB+UM) as compared to their starting input population of day 0 CD34+ cells was tested (FIG. 11a). UM-729 small molecule supplementation in the fed-batch bioreactor system enhanced overall CD34+ yield and minimized CD34− yield after 12 days of expansion as compared to control FB cultures (FIG. 11b, 11c).

Figures 11B, 11C, 11D, 11E:
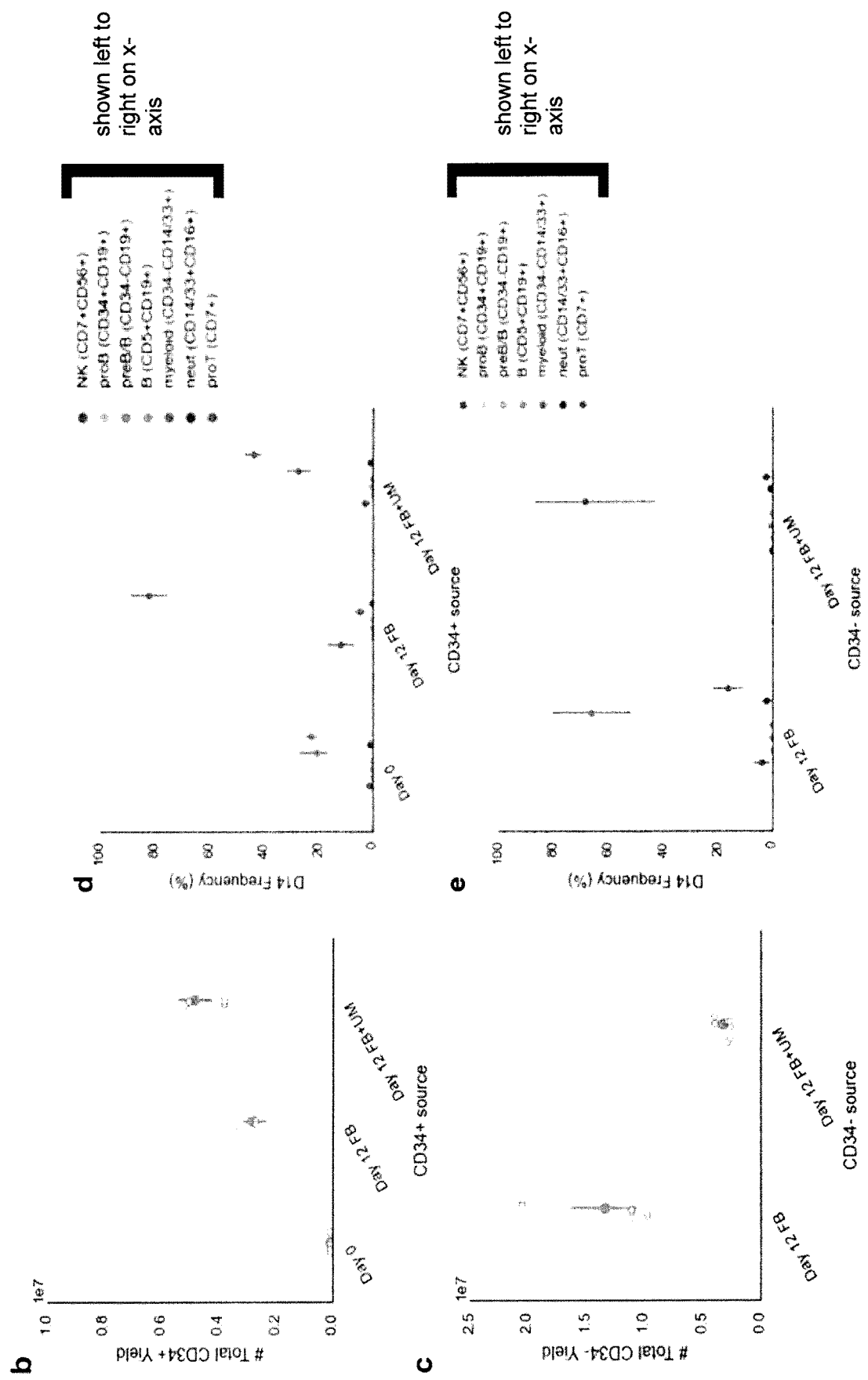
FIG. 11b: Graph depicting total yield of CD34+ cells obtained from 100,000 day 0 unexpanded CD34+ MACS-enriched cells, day 12 fed-batch (FB) and day 12 fed-batch+ UM729 (FB+UM) cultures.
FIG. 11c: Graph depicting total yield of CD34− cells obtained from day 12 FB and day 12 FB+UM cultures.
FIG. 11d: Graph depicting frequencies of lymphoid and myeloid populations obtained at day 26 of total culture or day 14 of the DL4+VCAM-1 assay from CD34+ cells derived from day 0 cord blood, day 12 FB and day 12 FB+UM cultures; the populations that were assessed include NK (CD7+CD56+), proB (CD34+CD19+), preB/B (CD34−CD19+), B (CD5+CD19+), myeloid (CD34−CD14/33+), neutrophils (CD14/33+CD16+) and proT (CD7+); day 12 FB-derived CD34+ cells without UM showed the highest frequencies of CD7+ proT cells and minimal skewing to the myeloid lineage.
FIG. 11e: Graph depicting frequencies of lymphoid and myeloid populations obtained at day 26 of total culture or day 14 of the DL4+VCAM-1 assay from CD34− cells derived from day 12 FB and day 12 FB+UM cultures; both cultures produced high frequencies of myeloid cells.
Figures 11F, 11G:
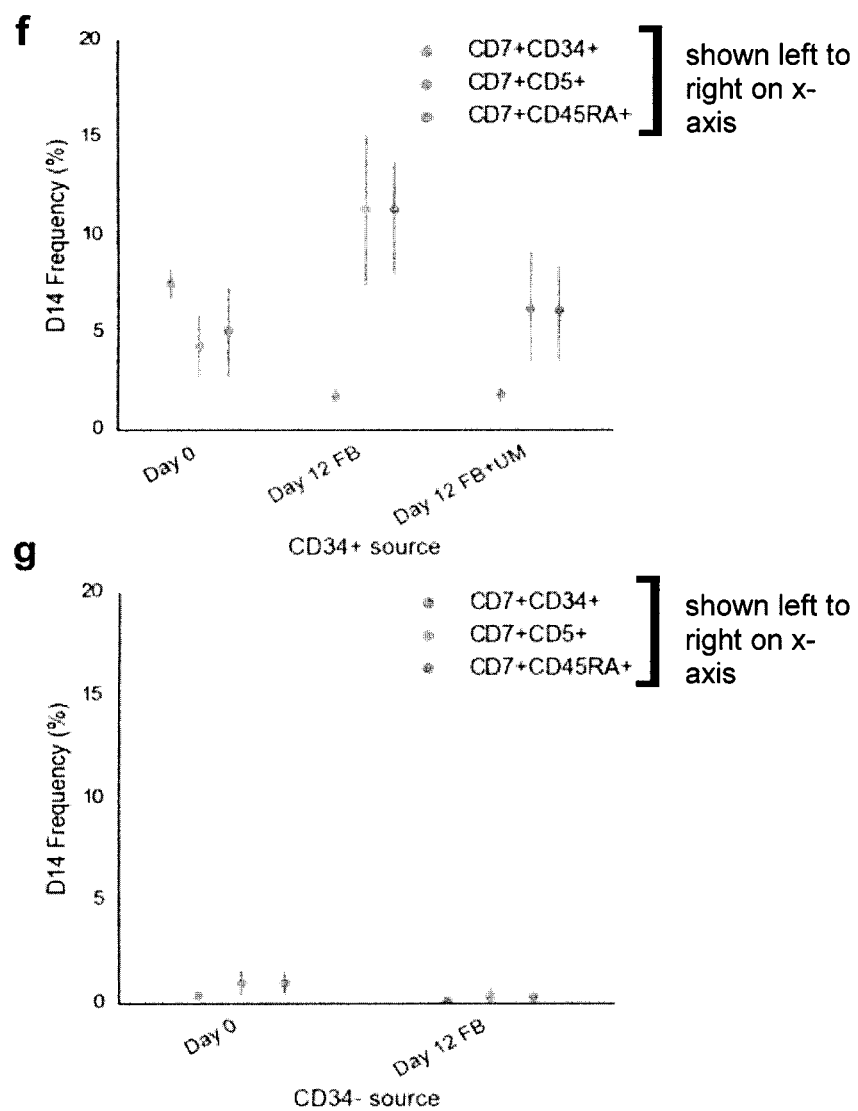
FIG. 11f: Graph depicting co-expression of progenitor T cell markers was assessed on CD7+ cells produced from CD34+ cells derived from day 0 cord blood, day 12 FB and day 12 FB+UM cultures; day 12 FB-derived CD34+ produced the highest frequencies of CD7+CD5+ and CD7+CD45RA+ proT cells while day 0 CD34+ produced the highest frequency of CD7+CD34+ primitive progenitor cells.
FIG. 11g: Graph depicting no co-expression of progenitor T cell markers was seen assessed on CD7-expressing cells produced from CD34− cells derived from day 0 or day 12 FB cultures.

Sorted CD34+ cells from FB culture generated the maximum frequency of CD7+ proT cells and CD7+CD56+NK cells after 14 days in the engineered thymic niche as compared to day 0 CD34+ cells and day 12 FB+UM-derived CD34+ cells (FIG. 11d). FB-derived CD34+ cells also showed minimal myeloid (CD34−CD14/CD33+) cell skewing while day 0 CD34+ and day 12 FB+UM CD34+ showed equivalent myeloid cell frequencies (FIG. 11d). All conditions did not generate proB cells (CD34+CD19+), preB/B cells (CD34−CD19+), B cells (CD5+CD19+) or neutrophils (CD14/CD33+CD16+) (FIG. 11d). Sorted CD34− cells from both FB and FB+UM culture generated primarily high frequencies of myeloid cells thus showing that T lymphoid potential was restricted to CD34+ cells (FIG. 11e). The proT lineage surface markers co-expressed on CD7+ cells were studied and it was found that while CD7+CD34+ primitive progenitors were highest in day 0 CD34+ cells, day 12 FB-derived CD34+ cells generated the highest CD5+ and CD45RA+co-expressing CD7+ proT cells (FIG. 11f). Although a small CD7+ cell population was generated from FB-derived CD34-cells (FIG. 11e), these cells did not co-express CD34, CD5 or CD45RA (FIG. 11g).

Figures 11H, 11I, 11J, 11K:
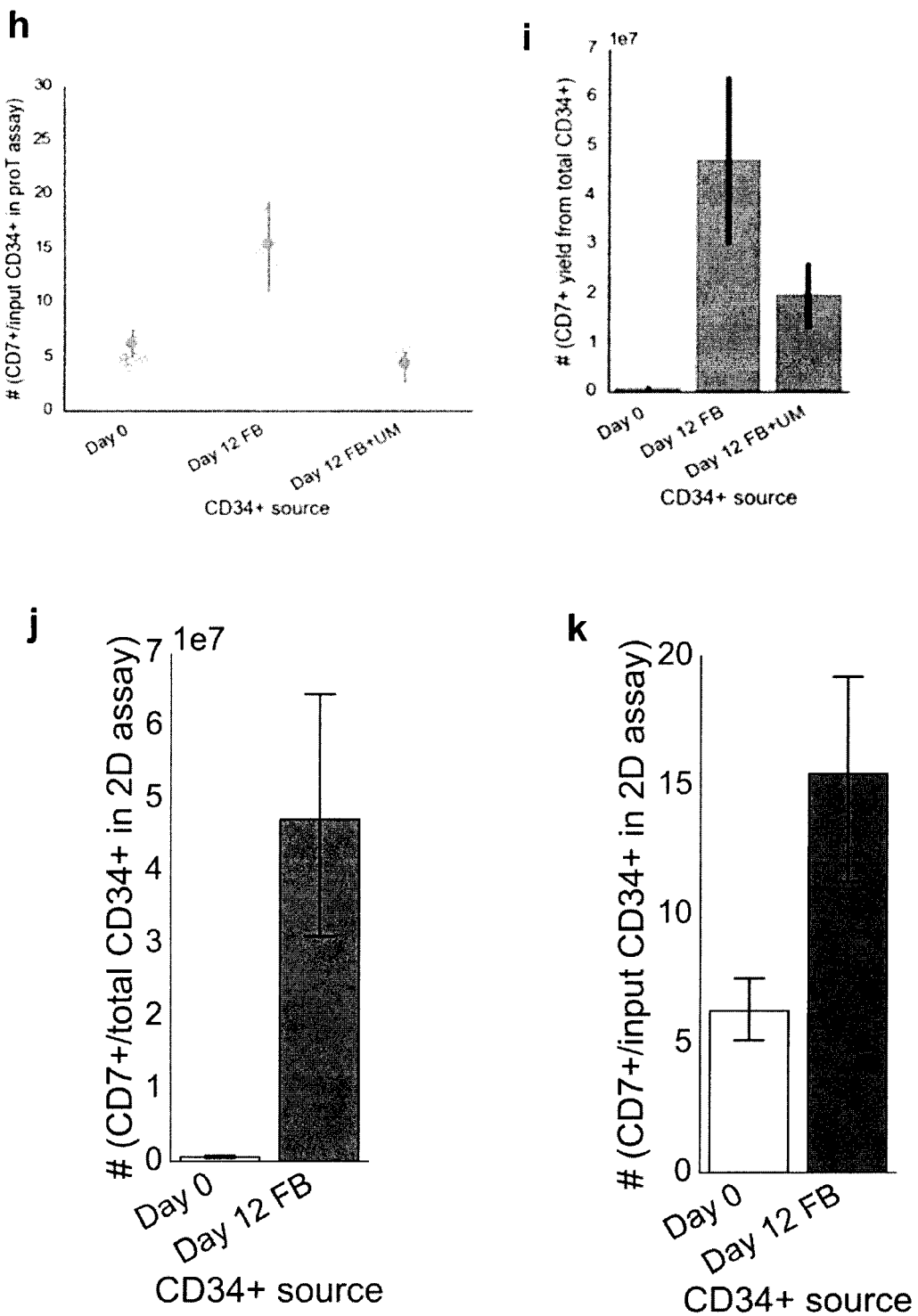
FIG. 11h: Graph depicting yield of CD7+ cells per input CD34+(from day 0 cord blood, day 12 FB and day 12 FB+UM) in the proT cell assay; day 12 FB showed the highest yield of CD7+ cells per input CD34+ in the proT assay (n=3).
FIG. 11i: Graph depicting yield of CD7+ cells from total number of CD34+ cells obtained from day 0 cord blood, day 12 FB and day 12 FB+UM cultures; day 12 FB again showed the highest yield of CD7+ cells from total number of CD34+ cells obtained from each culture method (n=3).
FIG. 11j: Graph depicting CD7+ proT-cell yield after 14 days on 2D DL4+VCAM-1 coated plates from total CD34+ cells harvested from day 0 cord blood or day 12 fed-batch expansion cultures (day 12 FB) (n=3).
FIG. 11k: Graph depicting CD7+ proT-cell yield after 14 days on 2D DL4+VCAM-1 coated plates per input CD34+ cell harvested from day 0 cord blood or day 12 fed-batch expansion cultures (day 12 FB) (n=3).
Figures 11L, 11M, 11N, 11O:
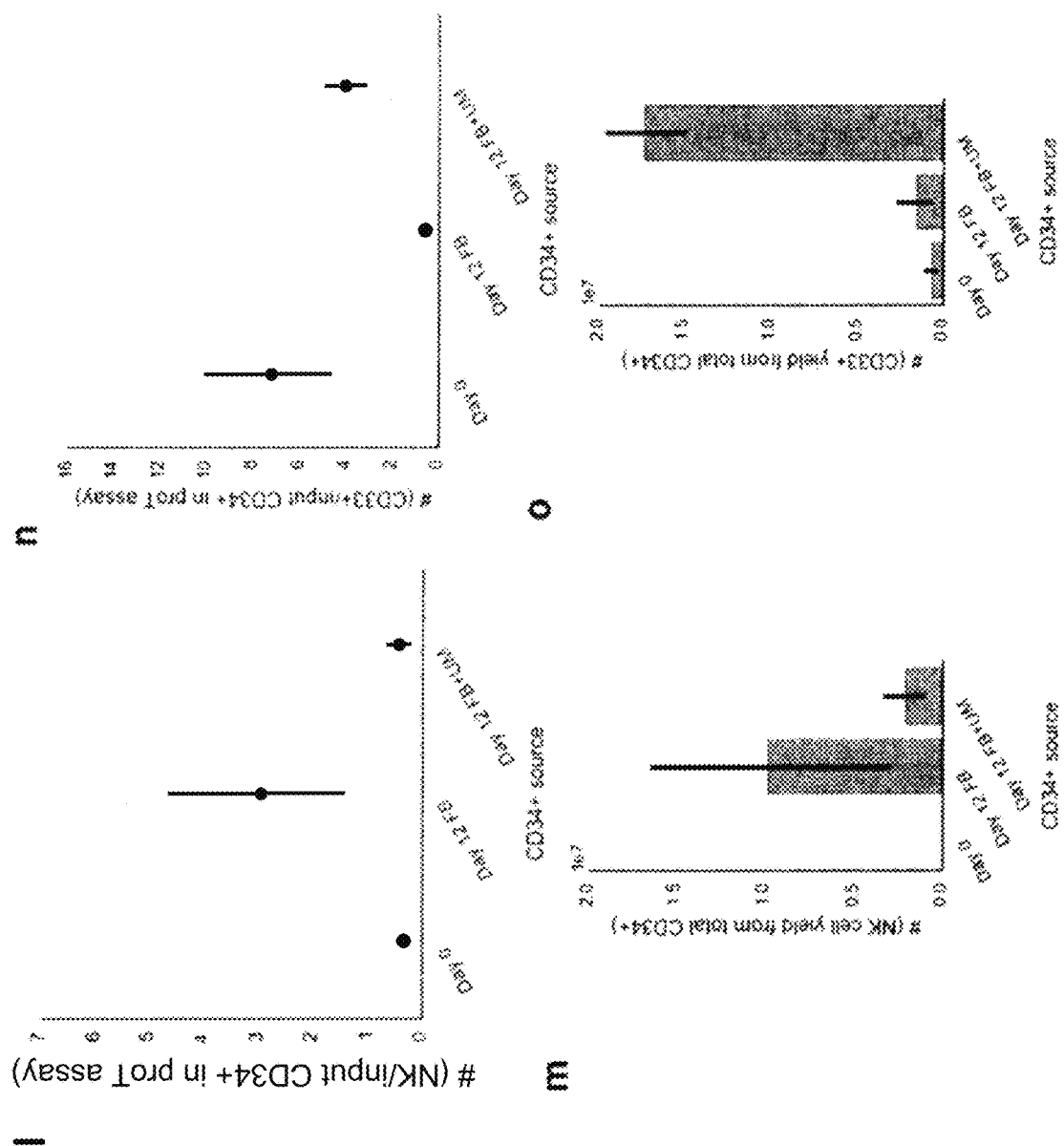
FIG. 11l: Graph depicting yield of CD7+CD56+NK cells per input CD34+(from day 0 cord blood, day 12 FB and day 12 FB+UM) in the proT cell assay; day 12 FB tended to have the highest yield of NK cells per input CD34+ in the proT assay (n=2).
FIG. 11m: Graph depicting yield of NK cells from total number of CD34+ cells obtained from day 0 cord blood, day 12 FB and day 12 FB+UM cultures; day 12 FB tended to have the highest yield of NK cells from total number of CD34+ cells obtained from each culture method (n=2).
FIG. 11n: Graph depicting yield of CD33+/CD14+ myeloid cells per input CD34+(from day 0 cord blood, day 12 FB and day 12 FB+UM) in the proT cell assay; day 12 FB+UM tended to have equivalent myeloid potential to day 0 cord blood per input CD34+ in the proT assay while day 12 FB showed suppressed myeloid skewing (n=2).

Next, the yield of CD7+ proT cells generated from CD34+ cells was quantified. Day 12 FB generated the highest yield of CD7+ cells per input CD34+ cell in the engineered thymic niche while day 0 CD34+ and day 12 FB+UM generated equivalent CD7+ yield per input CD34+ in the proT assay (FIG. 11h, 11k). If all CD34+ cells generated in the fed-batch cultures (FIG. 11b) were differentiated in the engineered thymic niche, day 12 FB would generate the maximum number of total CD7+ proT cells as compared to day 12 FB+UM-derived CD34+ or day 0 CD34+ cells (FIG. 11*l*, 11*j*). Similarly, day 12 FB-derived CD34+ cells generated the maximum number of NK cells per input CD34+ cells in the engineered thyme niche as well as total NK cell yield from total CD34+ cells generated in the FB culture system (FIG. 11*l*, 11*m*). In contrast, day 12 FB-derived CD34+ generate the least number of myeloid cells per input CD34+ cell in the engineered thymic niche (FIG. 11*n*). Day 12 FB+UM-derived CD34+ generated the highest yield of myeloid cells from total CD34+ cells as compared to day 0 CD34+ and day 12 FB-derived CD34+ cells (FIG. 11*o*). Thus, fed-batch bioreactor technology generated CD34+ cells that display lymphoid lineage bias with minimal myeloid lineage skewing, generated a higher yield of CD7+ proT cells and NK cells compared to input day 0 CD34+ cells. Addition of UM-729 to the fed-batch bioreactor system enhanced total generation of CD34+ cells that maintained a similar lympho-myeloid differentiation potential to input day 0 CD34+ cells.

Figure 12C:
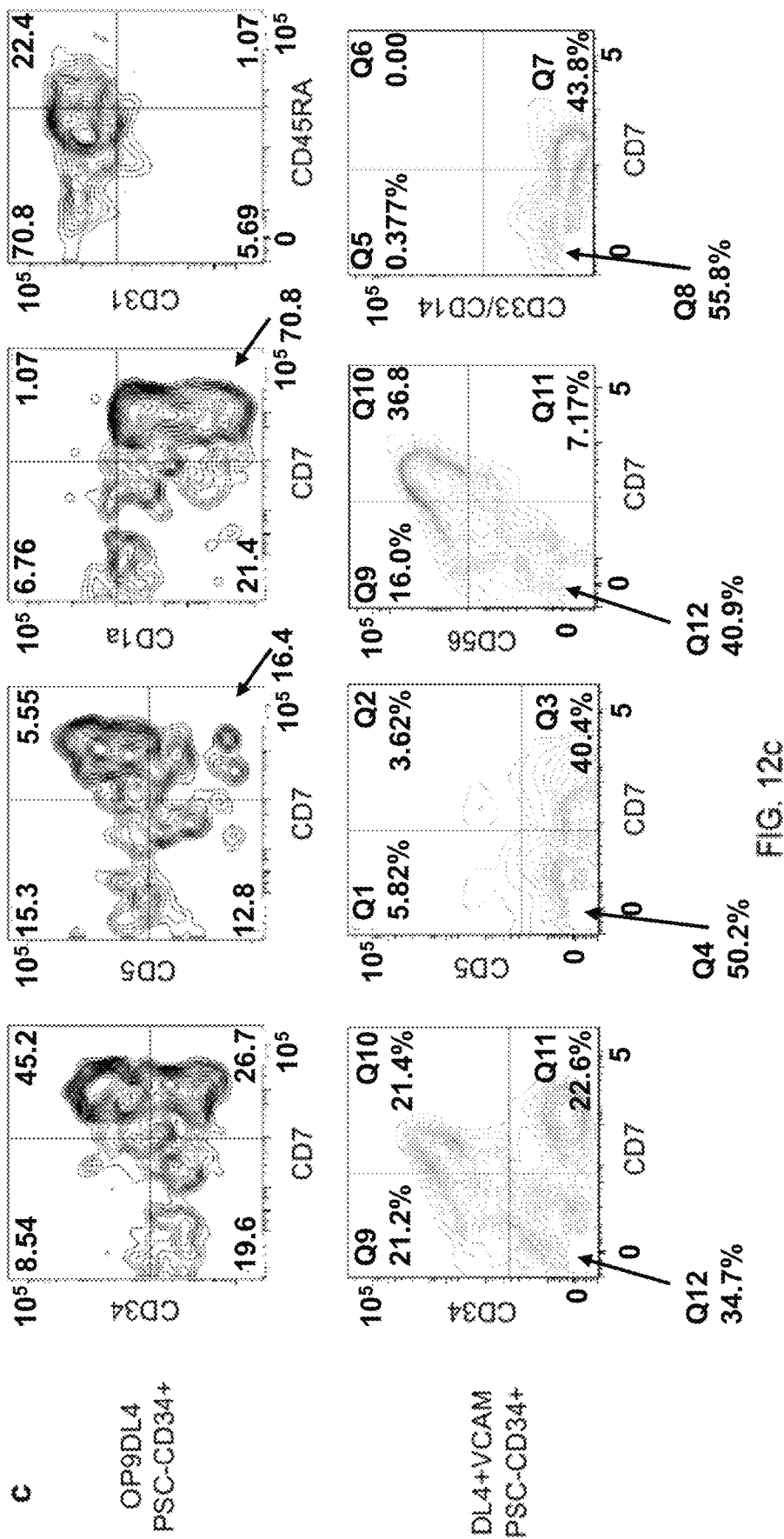
Figure 12D:
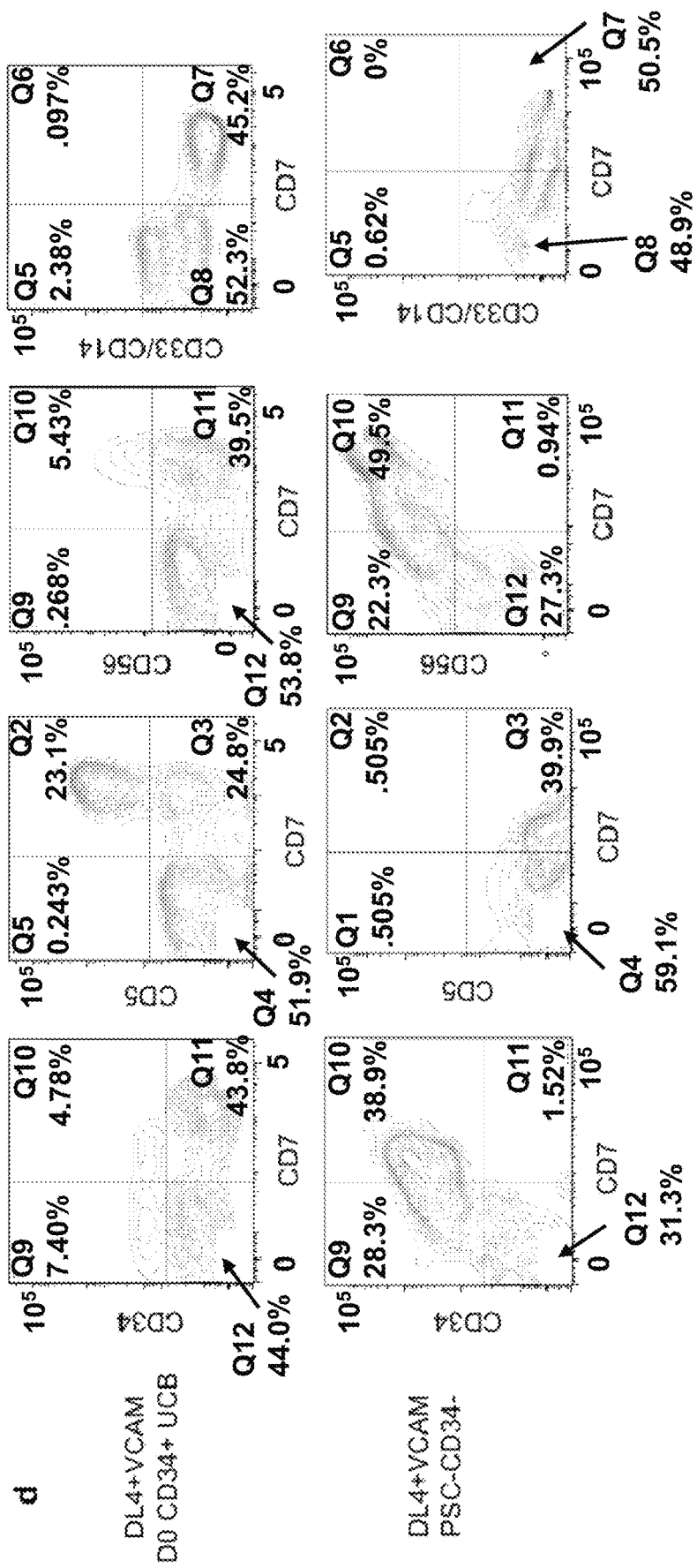
Figure 13A:
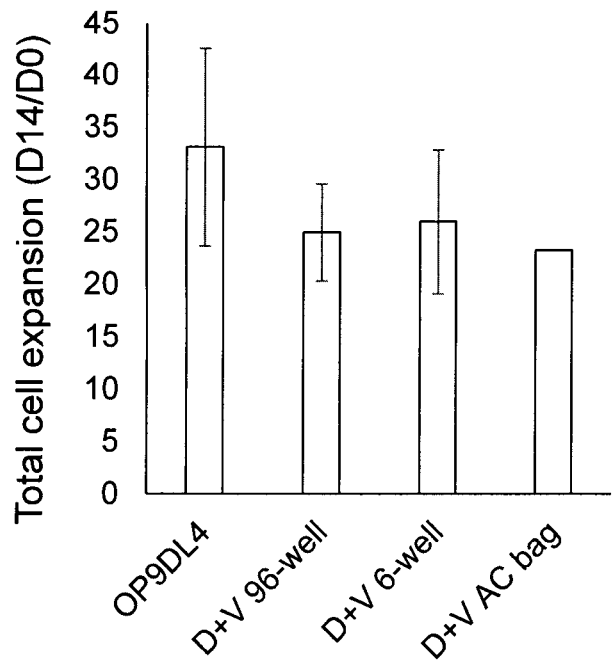
FIGS. 13a-c depict generation of human progenitor T cells in larger-scale culture formats.
Figure 13B:
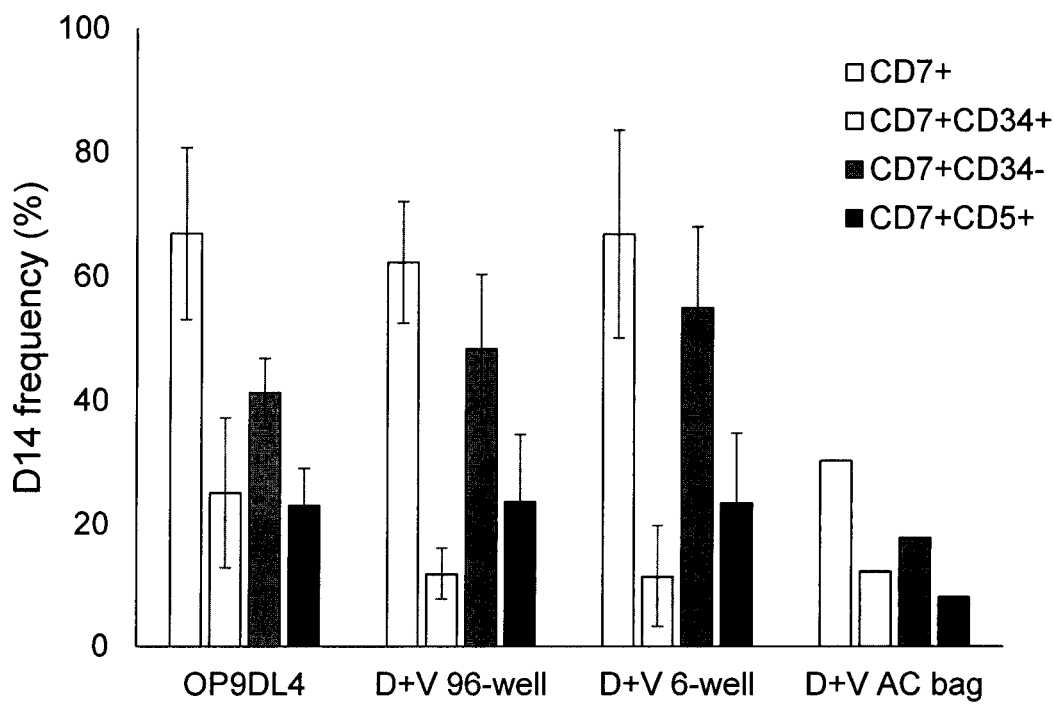
Figure 13C:
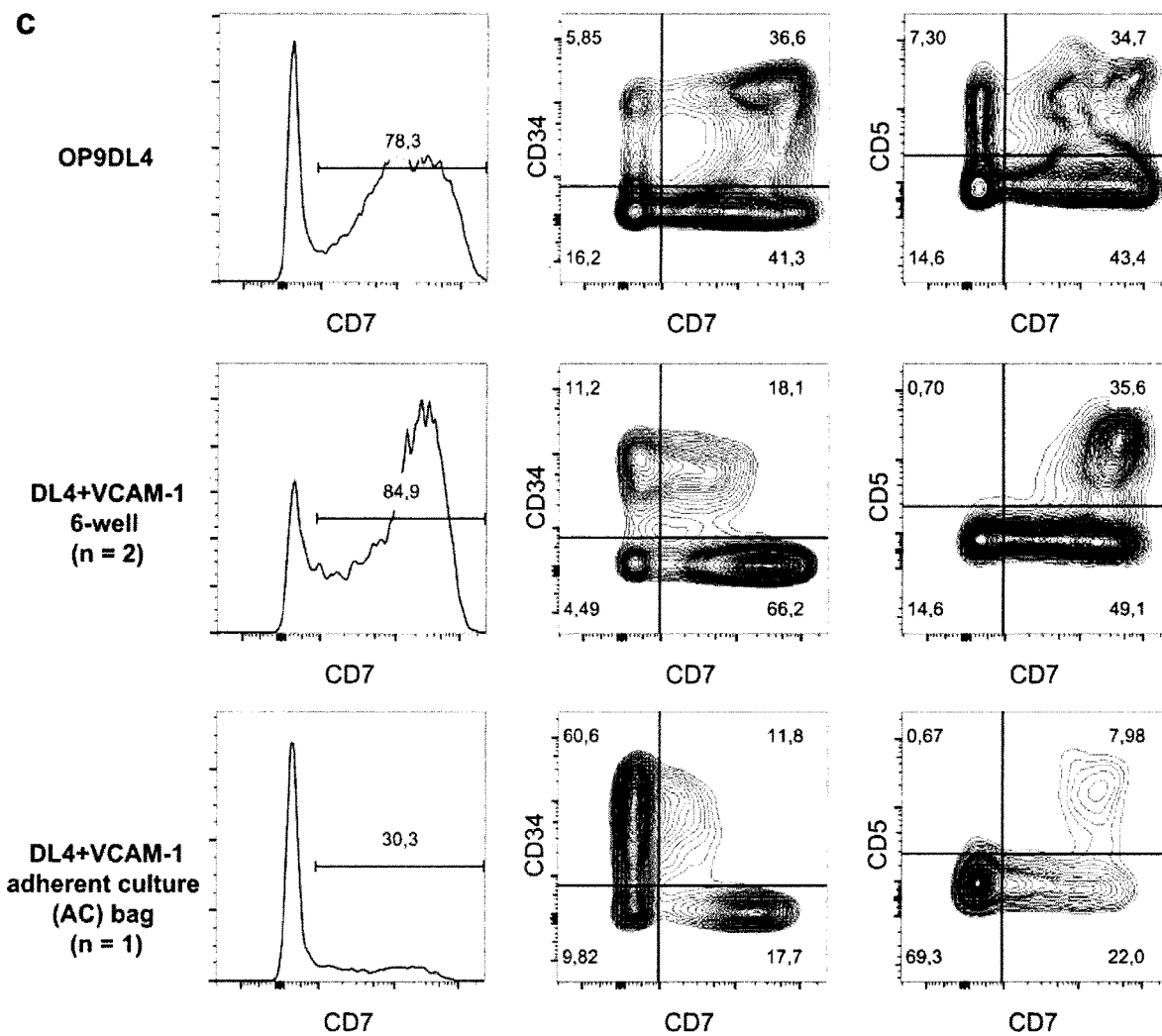

Example 7: Pluripotent Stem Cell (PSC)-Derived CD34+ Cells Generate CD7+ Cells in the Engineered Thymic Niche PSCs were differentiated for 6 days in a serum-free, defined aggregate size-based mesoderm differentiation protocol to generate CD34+ hemogenic endothelial cells that co-express CD43 and CD73 (FIG. 12*a*). Using magnetic-based cell enrichment, CD34+ population was selected and purity of the enriched cell population was assessed using flow cytometry (FIG. 12*b*). PSC-derived CD34+ cells were seeded in the gold standard OP9DL4 culture system or the DL4+VCAM-1 engineered thymic niche for two weeks. The OP9DL4 system generated cells from all stages of T cell development including CD7+CD34+, CD7+CD34− and CD7+CD5+(FIG. 12*c*). The engineered thymic niche produced CD7+CD34+, CD7+CD34−, a small fraction of CD7+CD5+ cells and showed no myeloid (CD33/CD14) lineage skewing (FIG. 12*c*). However, the CD7+ population also co-expressed high levels of CD56 indicating an NK lineage bias (FIG. 12*c*). The positive control used in this study was day 0 CD34+ cells from cord blood and negative control was PSC-derived CD34-cells that also generated a high frequency of CD7+CD34+ that co-express CD56 (FIG. 12*d*). Thus, current work seems to suggest that PSC-derived CD34+ and CD34− cells generate CD7+ cells that contain high NK lineage potential with minimal myeloid lineage bias.

Example 9: Scalable Progenitor T Cell Differentiation

Umbilical cord blood derived CD34+ cells were differentiated in parallel either in OP9DL4 stromal co-cultures compared with serum-free differentiation cultures in 96-well plates, 6-well plates, or adherent culture bioreactor bags coated with DL4+VCAM-1. The DL4+VCAM-1 coated surface area compared was kept roughly equivalent; half of a 96-well plate (15.4 cm$^2$) was compared with two wells in 6-well plate (19 cm$^2$) and 12 cm×2 cm bioreactor bag (24 cm$^2$). Total cell expansion after 14 days was found to be similar for all test conditions and ~25-fold expansion was observed from either 96-well, 6-well or bioreactor DL4+ VCAM-1 coated format (FIG. 15*a*). Frequencies of CD7+, CD7+CD34+, CD7+CD34− and CD7+CD5+ progenitor T-cells were analyzed after 14 days and were similar between all conditions for OP9DL4, 96-well and 6-well coated plates except for the most primitive CD7+CD34+ compartment (FIG. 15*b*, 15*c*). Thus, the DL4+VCAM-1 defined culture can be successfully scaled up to a 6-well format. However, the DL4+VCAM-1 coated adherent bioreactor bag produced fewer CD34−CD7+CD5+ progenitor T-cells (FIG. 15*b*, 15*c*) most likely due to being perfused with cytokine-containing medium on day 7 as opposed to 100% medium exchange conducted in the 96-well and 6-well plate formats.

Although the disclosure has been described with reference to certain specific embodiments, various modifications thereof will be apparent to those skilled in the art. Any examples provided herein are included solely for the purpose of illustrating the disclosure and are not intended to limit the disclosure in any way. Any drawings provided herein are solely for the purpose of illustrating various aspects of the disclosure and are not intended to be drawn to scale or to limit the disclosure in any way. The scope of the claims appended hereto should not be limited by the preferred embodiments set forth in the above description, but should be given the broadest interpretation consistent with the present specification as a whole. The disclosures of all prior art recited herein are incorporated herein by reference in their entirety.

DOCUMENTS CITED

1. Awong G, Herer E, Surh C D, Dick J E, La Motte-Mohs R N, Zúñiga-Pflücker J C. Characterization in vitro and engraftment potential in vivo of human progenitor T cells generated from hematopoietic stem cells. *Blood.* 2009; 114(5):972-982. doi:10.1182/blood-2008-10-187013.
2. La Motte-Mohs R N, Herer E, Zúñiga-Pflücker J C. Induction of T-cell development from human cord blood hematopoietic stem cells by Delta-like 1 in vitro. *Blood.* 2005; 105(4):1431-1439. doi: 10.1182/blood-2004-04-1293.
3. Ikawa T, Hirose S, Masuda K, et al. An essential developmental checkpoint for production of the T cell lineage. *Science.* 2010; 329(5987):93-96. doi:10.1126/science.1188995.
4. Taqvi S, Dixit L, Roy K. Biomaterial-based notch signaling for the differentiation of hematopoietic stem cells into T cells. *J Biomed Mater Res—Part A.* 2006; 79(3): 689-697. doi:10.1002/jbm.a.30916.
5. Roccio M, Gobaa S, Lutolf M P. High-throughput clonal analysis of neural stem cells in microarrayed artificial niches. *Integr Biol.* 2012; 4(4):391. doi:10.1039/c2ib00070a.
6. Mohtashami M, Shah D K, Nakase H, Kianizad K, Petrie H T, Zúñiga-Pflücker J C. Direct comparison of DII1- and DII4-mediated Notch activation levels shows differential lymphomyeloid lineage commitment outcomes. *J Immunol.* 2010; 185(2):867-876. doi:10.4049/jimmunol.1000782.
7. Milne C D, Zhang Y, Paige C J. Stromal Cells Attract B-Cell Progenitors to Promote B-Cell-B-Cell Contact and Maturation. *Scand J Immunol.* 2005; 62(s1):67-72. doi: 10.1111/j.1365-3083.2005.01612.x.
8. Varnum-Finney B, Wu L, Yu M, et al. Immobilization of Notch ligand, Delta-1, is required for induction of notch signaling. *J Cell Sci.* 2000; 113 Pt 23:4313-4318.
9. Holmes R, Zúñiga-Pflücker J C. The OP9-DL1 system: Generation of T-lymphocytes from embryonic or hematopoietic stem cells in vitro. Cold Spring Harb Protoc. 2009; 4(2):1-13. doi:10.1101/pdb.prot5156.

10. Kirouac D C, Madlambayan G J, Yu M, Sykes E A, Ito C, Zandstra P W. Cell-cell interaction networks regulate blood stem and progenitor cell fate. *Mol Syst Biol.* 2009; 5:293. doi: 10.1038/msb.2009.49.
11. Csaszar E, Gavigan G, Ungrin M, et al. An automated system for delivery of an unstable transcription factor to hematopoietic stem cell cultures. *Biotechnol Bioeng.* 2009; 103(2):402-412. doi: 10.1002/bit.22297.
12. Csaszar E, Kirouac D C, Yu M, et al. Rapid expansion of human hematopoietic stem cells by automated control of inhibitory feedback signaling. *Cell Stem Cell.* 2012; 10(2):218-229. doi:10.1016/j.stem.2012.01.003.
13. Purpura K A, Bratt-Ieal A M, Hammersmith K A, Mcdevitt T C, Zandstra P W. Biomaterials Systematic engineering of 3D pluripotent stem cell niches to guide blood development. *Biomaterials.* 2011:1-10. doi: 10.1016/j.biomaterials.2011.10.051.
14. Besseyrias V, Fiorini E, Strobl L J, et al. Hierarchy of Notch-Delta interactions promoting T cell lineage commitment and maturation. *J Exp Med.* 2007; 204(2):331-343. doi:10.1084/jem.20061442.
15. Andrawes M B, Xu X, Liu H, et al. Intrinsic Selectivity of Notch 1 for Delta-like 4 Over Delta-like 1. *J Biol Chem.* 2013; 288(35):25477-25489. doi: 10.1074/jbc.M113.454850.
16. Salomon D, Crisa L, Mojcik C, Ishii J, Klier G, Shevach E. Vascular cell adhesion molecule-1 is expressed by cortical thymic epithelial cells and mediates thymocyte adhesion. Implications for the function of alpha4beta1 (VLA4) integrin in T-cell development. *Blood.* 1997; 89(7):2461-2471.
17. Prockop S E, Palencia S, Ryan C M, Gordon K, Gray D, Petrie H T. Stromal cells provide the matrix for migration of early lymphoid progenitors through the thymic cortex. *J Immunol.* 2002; 169:4354-4361. doi: 10.4049/jimmunol. 169.8.4354.
18. Calderón L, Boehm T. Synergistic, context-dependent, and hierarchical functions of epithelial components in thymic microenvironments. *Cell.* 2012; 149(1):159-172. doi:10.1016/j.cell.2012.01.049.
19. Csaszar E, Wang W, Usenko T, et al. Blood stem cell fate regulation by Delta-1-mediated rewiring of IL-6 paracrine signaling. *Blood.* 2014; 123(5):650-658. doi: 10.1182/blood-2013-08-520445.
20. Hong C, Luckey M A, Park J H. Intrathymic IL-7: The where, when, and why of IL-7 signaling during T cell development. *Semin Immunol.* 2012; 24(3):151-158. doi: 10.1016/j.smim.2012.02.002.
21. Frasca D, Pioli C, Guidi F, et al. IL-11 synergizes with IL-3 in promoting the recovery of the immune system after irradiation. *Int Immunol.* 1996; 8(11):1651-1657. doi:10.1093/intimm/8.11.1651.
22. Petrie H T, Zúñiga-Pflücker J C. Zoned out: functional mapping of stromal signaling microenvironments in the thymus. *Annu Rev Immunol.* 2007; 25:649-679. doi: 10.1146/annurev.immunol.23.021704.115715.
23. Reimann C, Six E, Dal-Cortivo L, et al. Human T-lymphoid progenitors generated in a feeder-cell-free Delta-like-4 culture system promote T-cell reconstitution in NOD/SCID/γc(−/−) mice. *Stem Cells.* 2012; 30(8):1771-1780. doi:10.1002/stem.1145.
24. Awong G, Singh J, Mohtashami M, et al. Human proT-cells generated in vitro facilitate hematopoietic stem cell-derived T-lymphopoiesis in vivo and restore thymic architecture. *Blood.* 2013; 122(26):4210-4219. doi: 10.1182/blood-2012-12-472803.

We claim:

1. A method of generating progenitor T cells from stem and/or progenitor cells, the method comprising:

culturing a cell population comprising stem and/or progenitor cells in the presence of at least a portion of Notch ligand Delta-like-4 (DL4) and at least a portion of vascular adhesion molecule 1 (VCAM-1) under serum-free conditions in the absence of stromal or feeder cells, wherein said culturing step increases the yield of progenitor T cells in said cell population as compared to progenitor T-cells cultured under serum-free conditions in the absence of stromal or feeder cells and not cultured in the presence of at least a portion of DL4 and at least a portion of VCAM-1, and wherein said portion of DL4 comprises at least a signaling peptide of DL4, and wherein said portion of VCAM-1 comprises at least a signaling peptide of VCAM-1 and wherein the stem and/or progenitor stem cells are pluripotent stem cells or hematopoietic stem and progenitor cells.

2. The method of claim 1, wherein the culturing step further comprises generating derivatives of the generated progenitor T cells.

3. The method of claim 1, wherein the portion of DL4 comprises the extracellular domain of DL4, and/or wherein the portion of VCAM-1 comprises the Phe25 to Glu698 of SEQ ID NO: 4 fused with the Fe region of human IgG 1.

4. The method of claim 1, wherein at least one of the portion of DL4, or the portion of VCAM-1 is adsorbed or immobilized to a substrate.

5. The method of claim 1, wherein the portion of DL4 is provided in a concentration in the range of 7.5 to 20 µg/mL.

6. The method of claim 1, wherein the culturing of the cell population comprises exposing the cell population to a hematopoietic differentiation medium comprising SCF, FLT3L and IL-7.

7. The method of claim 1, wherein the cell population comprising stem and/or progenitor cells is a human cell population.

8. The method of claim 1, wherein the at least a portion of DL4 is the full-length DL4 polypeptide and/or the at least a portion of VCAM-1 is the full length VCAM-1 polypeptide.

9. The method of claim 6, wherein the hematopoietic differentiation medium further comprises thrombopoietin.

* * * * *

SEQUENCE LISTING

```
<160> NUMBER OF SEQ ID NOS: 41

<210> SEQ ID NO 1
<211> LENGTH: 685
<212> TYPE: PRT
<213> ORGANISM: Homo sapiens

<400> SEQUENCE: 1

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140
```

```
Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
```

```
                    565                 570                 575

Asp Asn Leu Ile Pro Ala Ala Gln Leu Lys Asn Thr Asn Gln Lys Lys
                580                 585                 590

Glu Leu Glu Val Asp Cys Gly Leu Asp Lys Ser Asn Cys Gly Lys Gln
            595                 600                 605

Gln Asn His Thr Leu Asp Tyr Asn Leu Ala Pro Gly Pro Leu Gly Arg
        610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685

<210> SEQ ID NO 2
<211> LENGTH: 6
<212> TYPE: PRT
<213> ORGANISM: Homo sapiens

<400> SEQUENCE: 2

Gln Ile Asp Ser Pro Leu
1               5

<210> SEQ ID NO 3
<211> LENGTH: 8
<212> TYPE: PRT
<213> ORGANISM: Homo sapiens

<400> SEQUENCE: 3

Thr Gln Ile Asp Ser Pro Leu Asn
1               5

<210> SEQ ID NO 4
<211> LENGTH: 739
<212> TYPE: PRT
<213> ORGANISM: Mus musculus

<400> SEQUENCE: 4

Met Pro Val Lys Met Val Ala Val Leu Gly Ala Ser Thr Val Leu Trp
1               5                   10                  15

Ile Leu Phe Ala Val Ser Gln Ala Phe Lys Ile Glu Ile Ser Pro Glu
            20                  25                  30

Tyr Lys Thr Ile Ala Gln Ile Gly Asp Ser Met Ala Leu Thr Cys Ser
        35                  40                  45

Thr Thr Gly Cys Glu Ser Pro Leu Phe Ser Trp Arg Thr Gln Ile Asp
    50                  55                  60

Ser Pro Leu Asn Ala Lys Val Arg Thr Glu Gly Ser Lys Ser Val Leu
65                  70                  75                  80

Thr Met Glu Pro Val Ser Phe Glu Asn Glu His Ser Tyr Leu Cys Thr
                85                  90                  95

Ala Thr Cys Gly Ser Gly Lys Leu Glu Arg Ser Ile His Val Asp Ile
            100                 105                 110

Tyr Ser Phe Pro Lys Asp Pro Glu Ile Gln Phe Ser Gly Pro Leu Glu
        115                 120                 125

Val Gly Lys Pro Val Thr Val Lys Cys Leu Ala Pro Asp Ile Tyr Pro
    130                 135                 140
```

```
Val Tyr Arg Leu Glu Ile Asp Leu Phe Lys Gly Asp Gln Leu Met Asn
145                 150                 155                 160

Arg Gln Glu Phe Ser Ser Glu Met Thr Lys Ser Leu Glu Thr Lys
            165                 170                 175

Ser Leu Glu Val Thr Phe Thr Pro Val Ile Glu Asp Ile Gly Lys Ala
            180                 185                 190

Leu Val Cys Arg Ala Lys Leu His Ile Asp Gln Ile Asp Ser Thr Leu
            195                 200                 205

Lys Glu Arg Glu Thr Val Lys Glu Leu Gln Val Tyr Ile Ser Pro Arg
            210                 215                 220

Asn Thr Thr Ile Ser Val His Pro Ser Thr Arg Leu Gln Glu Gly Gly
225                 230                 235                 240

Ala Val Thr Met Thr Cys Ser Ser Glu Gly Leu Pro Ala Pro Glu Ile
            245                 250                 255

Phe Trp Gly Arg Lys Leu Asp Asn Glu Val Leu Gln Leu Leu Ser Gly
            260                 265                 270

Asn Ala Thr Leu Thr Leu Ile Ala Met Arg Met Glu Asp Ser Gly Val
            275                 280                 285

Tyr Val Cys Glu Gly Val Asn Leu Ile Gly Arg Asp Lys Ala Glu Val
            290                 295                 300

Glu Leu Val Val Gln Glu Lys Pro Phe Ile Val Asp Ile Ser Pro Gly
305                 310                 315                 320

Ser Gln Val Ala Ala Gln Val Gly Asp Ser Val Val Leu Thr Cys Ala
            325                 330                 335

Ala Ile Gly Cys Asp Ser Pro Ser Phe Ser Trp Arg Thr Gln Thr Asp
            340                 345                 350

Ser Pro Leu Asn Gly Val Val Arg Asn Glu Gly Ala Lys Ser Thr Leu
            355                 360                 365

Val Leu Ser Ser Val Gly Phe Glu Asp Glu His Ser Tyr Leu Cys Ala
            370                 375                 380

Val Thr Cys Leu Gln Arg Thr Leu Glu Lys Arg Thr Gln Val Glu Val
385                 390                 395                 400

Tyr Ser Phe Pro Glu Asp Pro Val Ile Lys Met Ser Gly Pro Leu Val
            405                 410                 415

His Gly Arg Pro Val Thr Val Asn Cys Thr Val Pro Asn Val Tyr Pro
            420                 425                 430

Phe Asp His Leu Glu Ile Glu Leu Leu Lys Gly Glu Thr Thr Leu Met
            435                 440                 445

Lys Lys Tyr Phe Leu Glu Glu Met Gly Ile Lys Ser Leu Glu Thr Lys
            450                 455                 460

Ile Leu Glu Thr Thr Phe Ile Pro Thr Ile Glu Asp Thr Gly Lys Ser
465                 470                 475                 480

Leu Val Cys Leu Ala Arg Leu His Ser Gly Glu Met Glu Ser Glu Pro
            485                 490                 495

Lys Gln Arg Gln Ser Val Gln Pro Leu Tyr Val Asn Val Ala Pro Lys
            500                 505                 510

Glu Thr Thr Ile Trp Val Ser Pro Ser Pro Ile Leu Glu Glu Gly Ser
            515                 520                 525

Pro Val Asn Leu Thr Cys Ser Ser Asp Gly Ile Pro Ala Pro Lys Ile
            530                 535                 540

Leu Trp Ser Arg Gln Leu Asn Asn Gly Glu Leu Gln Pro Leu Ser Glu
545                 550                 555                 560
```

```
Asn Thr Thr Leu Thr Phe Met Ser Thr Lys Arg Asp Asp Ser Gly Ile
                565                 570                 575

Tyr Val Cys Glu Gly Ile Asn Glu Ala Gly Ile Ser Arg Lys Ser Val
            580                 585                 590

Glu Leu Ile Ile Gln Val Ser Pro Lys Asp Ile Gln Leu Thr Val Phe
        595                 600                 605

Pro Ser Lys Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Lys
625                 630                 635                 640

Thr Gly Asp Met Val Leu Lys Ser Val Asp Gly Ser Tyr Thr Ile Arg
                645                 650                 655

Gln Ala Gln Leu Gln Asp Ala Gly Ile Tyr Glu Cys Glu Ser Lys Thr
            660                 665                 670

Glu Val Gly Ser Gln Leu Arg Ser Leu Thr Leu Asp Val Lys Gly Lys
        675                 680                 685

Glu His Asn Lys Asp Tyr Phe Ser Pro Glu Leu Leu Ala Leu Tyr Cys
    690                 695                 700

Ala Ser Ser Leu Val Ile Pro Ala Ile Gly Met Ile Val Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 5
<211> LENGTH: 739
<212> TYPE: PRT
<213> ORGANISM: Homo sapiens

<400> SEQUENCE: 5

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190
```

-continued

```
Leu Val Cys Arg Ala Lys Leu His Ile Asp Glu Met Asp Ser Val Pro
            195                 200                 205

Thr Val Arg Gln Ala Val Lys Glu Leu Gln Val Tyr Ile Ser Pro Lys
210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
                275                 280                 285

Tyr Val Cys Glu Gly Val Asn Leu Ile Gly Lys Asn Arg Lys Glu Val
290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
                355                 360                 365

Thr Leu Ser Pro Val Ser Phe Glu Asn Glu His Ser Tyr Leu Cys Thr
370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
                420                 425                 430

Leu Asp Arg Leu Glu Ile Glu Leu Leu Lys Gly Glu Thr Ile Leu Glu
            435                 440                 445

Asn Ile Glu Phe Leu Glu Asp Thr Asp Met Lys Ser Leu Glu Asn Lys
450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
            515                 520                 525

Ser Val Asn Met Thr Cys Leu Ser Gln Gly Phe Pro Ala Pro Lys Ile
530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
            595                 600                 605

Pro Ser Glu Ser Val Lys Glu Gly Asp Thr Val Ile Ile Ser Cys Thr
```

```
                610             615             620
Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
                660                 665                 670

Lys Val Gly Ser Gln Leu Arg Ser Leu Thr Leu Asp Val Gln Gly Arg
            675                 680                 685

Glu Asn Asn Lys Asp Tyr Phe Ser Pro Glu Leu Leu Val Leu Tyr Phe
        690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 6
<211> LENGTH: 22
<212> TYPE: DNA
<213> ORGANISM: Artificial Sequence
<220> FEATURE:
<223> OTHER INFORMATION: synthetic primer

<400> SEQUENCE: 6
gaaatcgtgc gtgacatcaa ag                                          22

<210> SEQ ID NO 7
<211> LENGTH: 22
<212> TYPE: DNA
<213> ORGANISM: Artificial Sequence
<220> FEATURE:
<223> OTHER INFORMATION: synthetic primer

<400> SEQUENCE: 7
tgtagtttca tggatgccac ag                                          22

<210> SEQ ID NO 8
<211> LENGTH: 19
<212> TYPE: DNA
<213> ORGANISM: Artificial Sequence
<220> FEATURE:
<223> OTHER INFORMATION: synthetic primer

<400> SEQUENCE: 8
gggcgatgcc agaatagat                                              19

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
ggtagcctcc acatggtcag                                             20

<210> SEQ ID NO 10
<211> LENGTH: 20
<212> TYPE: DNA
<213> ORGANISM: Artificial Sequence
<220> FEATURE:
```

<223> OTHER INFORMATION: synthetic primer

<400> SEQUENCE: 10
gaggatgtgg ttcggaggta                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
ccctcatagc cagatgctgt                                              20

<210> SEQ ID NO 12
<211> LENGTH: 21
<212> TYPE: DNA
<213> ORGANISM: Artificial Sequence
<220> FEATURE:
<223> OTHER INFORMATION: synthetic primer

<400> SEQUENCE: 12
tttgacccta gccggacata c                                            21

<210> SEQ ID NO 13
<211> LENGTH: 19
<212> TYPE: DNA
<213> ORGANISM: Artificial Sequence
<220> FEATURE:
<223> OTHER INFORMATION: synthetic primer

<400> SEQUENCE: 13
gcataggcat tccgctcac                                               19

<210> SEQ ID NO 14
<211> LENGTH: 21
<212> TYPE: DNA
<213> ORGANISM: Artificial Sequence
<220> FEATURE:
<223> OTHER INFORMATION: synthetic primer

<400> SEQUENCE: 14
ctcggccatt cgtacatgga a                                            21

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
ggatacctct gcaccgtagc                                              20

<210> SEQ ID NO 16
<211> LENGTH: 21
<212> TYPE: DNA
<213> ORGANISM: Artificial Sequence
<220> FEATURE:
<223> OTHER INFORMATION: synthetic primer

<400> SEQUENCE: 16
tcaacacgac accggacaaa c                                            21

```
<210> SEQ ID NO 17
<211> LENGTH: 21
<212> TYPE: DNA
<213> ORGANISM: Artificial Sequence
<220> FEATURE:
<223> OTHER INFORMATION: synthetic primer

<400> SEQUENCE: 17
atgccgggag ctatctttct t                                          21

<210> SEQ ID NO 18
<211> LENGTH: 19
<212> TYPE: DNA
<213> ORGANISM: Artificial Sequence
<220> FEATURE:
<223> OTHER INFORMATION: synthetic primer

<400> SEQUENCE: 18
cccttgctct gcctaacgc                                             19

<210> SEQ ID NO 19
<211> LENGTH: 19
<212> TYPE: DNA
<213> ORGANISM: Artificial Sequence
<220> FEATURE:
<223> OTHER INFORMATION: synthetic primer

<400> SEQUENCE: 19
ggagtcctgg catcgttgg                                             19

<210> SEQ ID NO 20
<211> LENGTH: 22
<212> TYPE: DNA
<213> ORGANISM: Artificial Sequence
<220> FEATURE:
<223> OTHER INFORMATION: synthetic primer

<400> SEQUENCE: 20
atgttacagg cgtgcaaaat gg                                         22

<210> SEQ ID NO 21
<211> LENGTH: 21
<212> TYPE: DNA
<213> ORGANISM: Artificial Sequence
<220> FEATURE:
<223> OTHER INFORMATION: synthetic primer

<400> SEQUENCE: 21
tgatcgctat ggctttctcc a                                          21

<210> SEQ ID NO 22
<211> LENGTH: 22
<212> TYPE: DNA
<213> ORGANISM: Artificial Sequence
<220> FEATURE:
<223> OTHER INFORMATION: synthetic primer

<400> SEQUENCE: 22
agctttctcc actctacgaa ca                                         22

<210> SEQ ID NO 23
<211> LENGTH: 21
<212> TYPE: DNA
<213> ORGANISM: Artificial Sequence
<220> FEATURE:
<223> OTHER INFORMATION: synthetic primer
```

<400> SEQUENCE: 23
aatccagaga gatcgggggt c					21

<210> SEQ ID NO 24
<211> LENGTH: 21
<212> TYPE: DNA
<213> ORGANISM: Artificial Sequence
<220> FEATURE:
<223> OTHER INFORMATION: synthetic primer

<400> SEQUENCE: 24
catgtacgtt gctatccagg c					21

<210> SEQ ID NO 25
<211> LENGTH: 21
<212> TYPE: DNA
<213> ORGANISM: Artificial Sequence
<220> FEATURE:
<223> OTHER INFORMATION: synthetic primer

<400> SEQUENCE: 25
ctccttaatg tcacgcacga t					21

<210> SEQ ID NO 26
<211> LENGTH: 21
<212> TYPE: DNA
<213> ORGANISM: Artificial Sequence
<220> FEATURE:
<223> OTHER INFORMATION: synthetic primer

<400> SEQUENCE: 26
tccagctaca tttgcacaac a					21

<210> SEQ ID NO 27
<211> LENGTH: 20
<212> TYPE: DNA
<213> ORGANISM: Artificial Sequence
<220> FEATURE:
<223> OTHER INFORMATION: synthetic primer

<400> SEQUENCE: 27
gctccaggta gatgcggaag					20

<210> SEQ ID NO 28
<211> LENGTH: 20
<212> TYPE: DNA
<213> ORGANISM: Artificial Sequence
<220> FEATURE:
<223> OTHER INFORMATION: synthetic primer

<400> SEQUENCE: 28
atcggagaag gctctacagg					20

<210> SEQ ID NO 29
<211> LENGTH: 21
<212> TYPE: DNA
<213> ORGANISM: Artificial Sequence
<220> FEATURE:
<223> OTHER INFORMATION: synthetic primer

<400> SEQUENCE: 29
cgtctggcct cctttctaac t					21

<210> SEQ ID NO 30
<211> LENGTH: 20

```
<212> TYPE: DNA
<213> ORGANISM: Artificial Sequence
<220> FEATURE:
<223> OTHER INFORMATION: synthetic primer

<400> SEQUENCE: 30
ccgactccta cagtgggcta                                                    20

<210> SEQ ID NO 31
<211> LENGTH: 19
<212> TYPE: DNA
<213> ORGANISM: Artificial Sequence
<220> FEATURE:
<223> OTHER INFORMATION: synthetic primer

<400> SEQUENCE: 31
cgctgacgtg ttctcctcg                                                     19

<210> SEQ ID NO 32
<211> LENGTH: 20
<212> TYPE: DNA
<213> ORGANISM: Artificial Sequence
<220> FEATURE:
<223> OTHER INFORMATION: synthetic primer

<400> SEQUENCE: 32
gttggcctaa ggtggttgtg                                                    20

<210> SEQ ID NO 33
<211> LENGTH: 20
<212> TYPE: DNA
<213> ORGANISM: Artificial Sequence
<220> FEATURE:
<223> OTHER INFORMATION: synthetic primer

<400> SEQUENCE: 33
acaggctgca ggaataggga                                                    20

<210> SEQ ID NO 34
<211> LENGTH: 20
<212> TYPE: DNA
<213> ORGANISM: Artificial Sequence
<220> FEATURE:
<223> OTHER INFORMATION: synthetic primer

<400> SEQUENCE: 34
cctgtcatcc ccgtctacac                                                    20

<210> SEQ ID NO 35
<211> LENGTH: 19
<212> TYPE: DNA
<213> ORGANISM: Artificial Sequence
<220> FEATURE:
<223> OTHER INFORMATION: synthetic primer

<400> SEQUENCE: 35
cacatggagt ccgccgtaa                                                     19

<210> SEQ ID NO 36
<211> LENGTH: 19
<212> TYPE: DNA
<213> ORGANISM: Artificial Sequence
<220> FEATURE:
<223> OTHER INFORMATION: synthetic primer

<400> SEQUENCE: 36
```

-continued

```
gaggcgtggc agactatgc                                          19

<210> SEQ ID NO 37
<211> LENGTH: 20
<212> TYPE: DNA
<213> ORGANISM: Artificial Sequence
<220> FEATURE:
<223> OTHER INFORMATION: synthetic primer

<400> SEQUENCE: 37
cttgtactcc gtcagcgtga                                         20

<210> SEQ ID NO 38
<211> LENGTH: 20
<212> TYPE: DNA
<213> ORGANISM: Artificial Sequence
<220> FEATURE:
<223> OTHER INFORMATION: synthetic primer

<400> SEQUENCE: 38
tgcaatgtca agggaggggg                                         20

<210> SEQ ID NO 39
<211> LENGTH: 21
<212> TYPE: DNA
<213> ORGANISM: Artificial Sequence
<220> FEATURE:
<223> OTHER INFORMATION: synthetic primer

<400> SEQUENCE: 39 aaaccttcc attttgcacg c                                        21

<210> SEQ ID NO 40
<211> LENGTH: 21
<212> TYPE: DNA
<213> ORGANISM: Artificial Sequence
<220> FEATURE:
<223> OTHER INFORMATION: synthetic primer

<400> SEQUENCE: 40
tgcacatgca gctataccca g                                       21

<210> SEQ ID NO 41
<211> LENGTH: 22
<212> TYPE: DNA
<213> ORGANISM: Artificial Sequence
<220> FEATURE:
<223> OTHER INFORMATION: synthetic primer

<400> SEQUENCE: 41
tggtggattc ttggtgcttt tc                                      22
```